(12) United States Patent
Neumann et al.

(10) Patent No.: US 8,628,751 B2
(45) Date of Patent: Jan. 14, 2014

(54) PYRAZINE DERIVATIVES FOR OPTICAL IMAGING AND THERAPY

(75) Inventors: William L. Neumann, St. Louis, MO (US); John N. Freskos, Clayton, MO (US)

(73) Assignee: Medi Beacon Development, LLC, St. Louis, MO (US)

( * ) Notice: Subject to any disclaimer, the term of this patent is extended or adjusted under 35 U.S.C. 154(b) by 127 days.

(21) Appl. No.: 13/263,999

(22) PCT Filed: Apr. 15, 2010

(86) PCT No.: PCT/US2010/031203
§ 371 (c)(1),
(2), (4) Date: Oct. 12, 2011

(87) PCT Pub. No.: WO2010/121003
PCT Pub. Date: Oct. 21, 2010

(65) Prior Publication Data
US 2012/0027682 A1    Feb. 2, 2012

Related U.S. Application Data

(60) Provisional application No. 61/169,800, filed on Apr. 16, 2009.

(51) Int. Cl.
*A61K 49/00* (2006.01)
*A61K 31/4965* (2006.01)

(52) U.S. Cl.
USPC ............... 424/9.1; 424/9.2; 424/9.3; 424/9.4; 514/156; 514/157; 514/255.05; 514/255.06

(58) Field of Classification Search
USPC .......... 424/9.1–94; 514/79, 156, 157, 255.05, 514/255.06
See application file for complete search history.

(56) References Cited

U.S. PATENT DOCUMENTS

| | | | |
|---|---|---|---|
| 5,672,333 | A | 9/1997 | Rajagopalan et al. |
| 6,258,378 | B1 | 7/2001 | Schneider et al. |
| 6,406,713 | B1 | 6/2002 | Janoff et al. |
| 7,128,896 | B2 | 10/2006 | Achilefu et al. |
| 7,201,892 | B2 | 4/2007 | Achilefu et al. |

FOREIGN PATENT DOCUMENTS

| | | |
|---|---|---|
| WO | 2006/071759 | 7/2006 |
| WO | 2007/149478 | 12/2007 |
| WO | 2009/018405 | 2/2009 |

OTHER PUBLICATIONS

Ansorge et al., "An upstream CRE-E box element is essential for gastrin-dependent activation of teh cyclooxygenase-2 gene in human colon cancer cells". Regulatory Peptides 2007 144 (1-3), 25-33.

Chan et al., "Aspirin and the risk of colorectal cancer in relation to the expression of COX-2", New England Journal of Medicine, 2007, 356(21), 2131-2142.
Tsuji et al., "Involvement of cyclooxygenase-2 in colorectal carcinogenesis". Recent advances in Gastrointestinal Carcinogenesis, 2006, 125-143.
Duque et al., "Up-regulation of cyclooxygenase-2 by interleukin-1beta in colon carcinoma cells". Cellular Signalling, 2006, 18(8), 1262-1269.
Tong et al., "Cyclooxygenase-2 Regulation in Colon Cancer Cells", Journal of Biological Chemistry, 2005, 280(16), 15503-15509.
Ghosh et al., "Regulation of Cox-2 by cyclic AMP response element binding protein in prostate cancer: potential role for nexrutine", Neoplasia (Ann Arbor, MI, United States), 2007, 9(11), 893-899.
de Maat et al, "Epigenetic silencing of cyclooxygenase-2 affects clinical outcome in gastric cancer", Journal of Clinical Oncology, 2007, 25(31), 4887-4894.
Xing et al. "Changes of COX-2 and VEGF expressions in esophageal precancerous and cancerous lesions from the patients at high incidence area in Henan province", Life Science Journal, 2007, 4(2), 11-14.
Wang et al., "Detection of COX-2, VEGF, and MVD in uterine endometrial carcinoma tissue", Zhengzhou Daxue Xuebao, Yixueban, 2006, 41(5), 952-954.
Stoeltzing et al., "Regulation of cyclooxygenase-2 (COX-2) expression in human pancreatic carcinoma cells by the insulin-like growth factor-1 receptor (IGF-IR) system", Cancer letters (Amsterdam, Netherlands), 2007, 258(2), 291-300.
Guo et al. "Mechanism and effect of selective COX-2 inhibitor nimesulide on the chemotherapy sensitiveness in breasr cancer cell lines", Zhonghua Zhongliu Fangzhi Zazhi, 2006, 13(16), 1214-1218.
Saldivar et al. "COX-2 overexpression as a blomarker of early cervical carcinogenesis: A pilot study" Gynecologic Oncology, 2007, 107(1, Suppl. 1), 5155-5162.
Bergmann et al., "Expansion of Human T Regulatory Type 1 Cells in the Microenvironment of Cyclooxygenase 2 Overexpressing Head and Neck Squamous Cell Carcinoma", Cancer Research, 2007, 67(18), 8865-8873.
Xu et al, "Effect of tanshinone II A on COX-2 expression in hepatocellular carcinoma cell line SMMC-7221", Shihie Huaren Xiaohua Zazhi, 2006, 14(14), 1352-1356.
Rundhaug et al, "A role for cyclooxygenase-2 in ultraviolet light-induced skin carcinogenesis", Molecular Carcinogenesis, 2007, 46(8), 692-698.
Kiguclii et al, "Therapeutic effect of CS-706, a specific cyclooxygenase-2 inhibitor, on gallbladder carcinomain BK5.ErbB-2 mice", Molecular Cancer Therapeutics, 2007, 6(6), 1709-1717.
Grozio et al., "Nicotine, lung and cancer", Anti-Cancer Agents in Medicinal Chemistry, 2007, 7(4), 461-466.

(Continued)

*Primary Examiner* — Michael G Hartley
*Assistant Examiner* — Jagadishwar Samala
(74) *Attorney, Agent, or Firm* — Dennis A. Bennett; Gale W. Starkey

(57) ABSTRACT

The invention provides compounds, including compositions, preparations and formulations, and methods of using and making such compounds. Compounds of the present invention include pyrazine derivatives having a pyrazine core and a plurality of substituents. In some embodiments, pyrazine derivatives of the invention are pyrazine core compounds having one or more electron donating groups and one or more electron withdrawing groups optionally functionalized to provide useful optical, biological, pharmacokinetic and/or physical properties.

13 Claims, 1 Drawing Sheet

(56) References Cited

OTHER PUBLICATIONS

Cao et al., "Insulin-like growth factor-I induces cyclooxygenase-2 expression via PI3K, MAPK and PKC signaling pathways in human ovarian cancer cells", Cellular Signalling, 2007, 19(7), 1542-1553.

Lai et al., "Inhibitory effect of citrus 5-hydroxy-3,6,7,8,3',4'-hexamethoxyflavone on 12-O-tetradecanoylphorbol 13-acetate-induced skin inflammation and tumor promotion in mice", Carcinogenesis, 2007, 28(12), 2581-2588.

Chen et al, "Effects of COX-2 Inhibitor on growth of human gastric cells and its relation to hepatocyte growth factor", Cancer letters (Amsterdam, Netherlands), 2006, 239(2), 263-270.

Issa et al, "Green tea selectively targets initial stages of intestinal carninogenesis in the AOM-ApcMin mouse model", Carcinogenesis, 2007, 28(9), 1978-1984.

Eisinger et al., "Retinoic Acid Inhibits-Catenin through Suppression of Cox-2: A role for truncated adenomatous polyposis coli", Journal of Biological Chemistry, 2007, 282(40), 29394-29400.

Corona et al, "Inhibition of p38/CREB phosphorylation and COX-2 expression by olive oil polyphenols underlies their anti-proliferative effects", Biochemical and Biophysical Research Communications, 2007, 362(3), 606-611.

Sane Yasushi et al, "Colon polyp and COX-2 inhibitor", Gan Bunshi Hyoteki Chiryc, 2007, 5(2), 141-145.

Anti-EGFR and ErbB-2 antibodies attenuate cyclooxygenase-2 expression and cooperatively inhibit survival of human colon cancer cells, Cancer Letters (Amersterdam Netherlands), 2007, 251(2), 237-246.

Jimeno et al, "Assessment of celecoxib pharmacodynamics in pancreatic cancer", Molecular Cancer Therapeutics, 2006, 5(12), 3240-3247.

Fu et al, "COX-2 inhibitors suppress activation of NF-k B in gastric cancer", Jiangxi Yixueyuan Xuebao, 2006, 46(4), 16-20.

Kem et al, "Cyclooxygenase-2 Inhibition Induces Apoptosis Singaling via Death Receptors and Mitochondria in Hepatocellular Carcinoma", Cancer Research, 2006, 66(14), 7059.

Krysan et al, "The potential and rationale for COX-2 inhibitors in lung cancer", Anti-Cancer Agents in Medicinal Chemistry, 2006, 6(3), 209-220.

Irie et al, Combination therapy of anticancer drugs and cyclooxygenase-2 (COX-2) inhibitors, Shokakika, 2006, 42(2), 168-172.

Szabo et al., "New Celecoxib Derivatives as Anti-inflammatory Agents", Journal of Medicinal Chemistry, 2008, 51, pp. 142-147.

Singh et al. "Synthesis and biological evaluation of 2,3-diarylpyrazines and quinoxalines as selective COX-2 inhibitors", Bioorganic and Medicinal Chemistry, vol. 12, No. 4, (2004), pp. 1881-1893.

Benaron et al. "Optical Time-of-Flight and Absorbance Imaging of Biologic Media", Science, 1993, 259, pp. 1463-1466.

Tearney et al., "In vivo Endoscopic Optical Biopsy with Optical Coherence Tomography", Science, 1997, 276, pp. 2037-2039.

Tromberg at al., "Non-invasive measurements of breast tissue optical properties using frequency-domain photon migration", Phil. Trans. Royal Society London B, 1997, 352, pp. 661-668.

Fantini et al, "Assessment ofthe size, position, and optical properties of breast tumors in vivo by noninvasive optical methods", Applied Optics, 1998, 37, pp. 1982-1989.

Pelegrin et al, "Photoimmunodiagnosis with anitbody-fluorescein conjugates: in vitro and in vivo preclinical studies", J. Cell Pharmacol., 1992, 3, pp. 141-145.

Zheng Huang, "A Review of Progress in Clinical Photodynamic Therapy", Technol. Cancer Res Treat. 2005, Jun.; 4 (3): 283-293.

Brown at al., "The present and future role of photodynamic therapy in cancer treatment", Lancet Oncol. 2004, 5, pp. 497-508.

Triesscheijn et al., "Photodynamic Therapy in Oncology", The Oncologist, 2006, 11: 1034-1044.

Dougherty et al. "Photodynamic Therapy", J. Natl. Cancer Inst., 1998, 90: oo. 899-905.

A. Giannis et al. "Peptidomimetics for Receptor Ligands—Discovery, Development, and Medical Perspectives", Angew. Chem. Int. Ed. Engl., vol. 32, 1993, pp. 1244-1267.

Patch et al., "Versatile Oligo (N-Substituted) Glycines: The Many Roles of Peptoids in Drug Discovery", Pseudo-Peptides in Drug Discovery 2004, 1-31.

Winter et al., "Carrageenin-Induced Edema in Hind Paw of the Rat as an Assay for Antiinflammatory Drugs", Proc. Soc. Exp. Biol. Med., III, 544 (1962).

Hargreaves et al. "A new and sensitive method for measuring thermal nociception in cutaneous hyperalgesia", Pain, 32, 77 (1988).

Cochrane et al. "Etoricoxib", Drugs (2002), 62: 2637-2651.

Spiegel et al. "Use of Nonaqueous Solvents in Parental Products", J. Pharma Sciences, vol. 52, No. 10, pp. 917-927. (1963).

Bundgaard et al. (1988) "Glycolamide Esters as Biolabile Prodrugs of Carboxylic Acid Agents", Journal of Pharmaceutical Sciences, vol. 77, No. 4, p. 285.

Shirai et al, "Synthesis of fluorescent proeprties of 2,5-diamino-3,6-dicyanopyrazine dyes", Dyes and Pigments 1998, 39(1), 49-68.

J.G. Nairn, (1985), "Solutions, Emulsions, Suspension, and Extractives", Remington's Pharmaceutical Scinece, pp. 1492-1517.

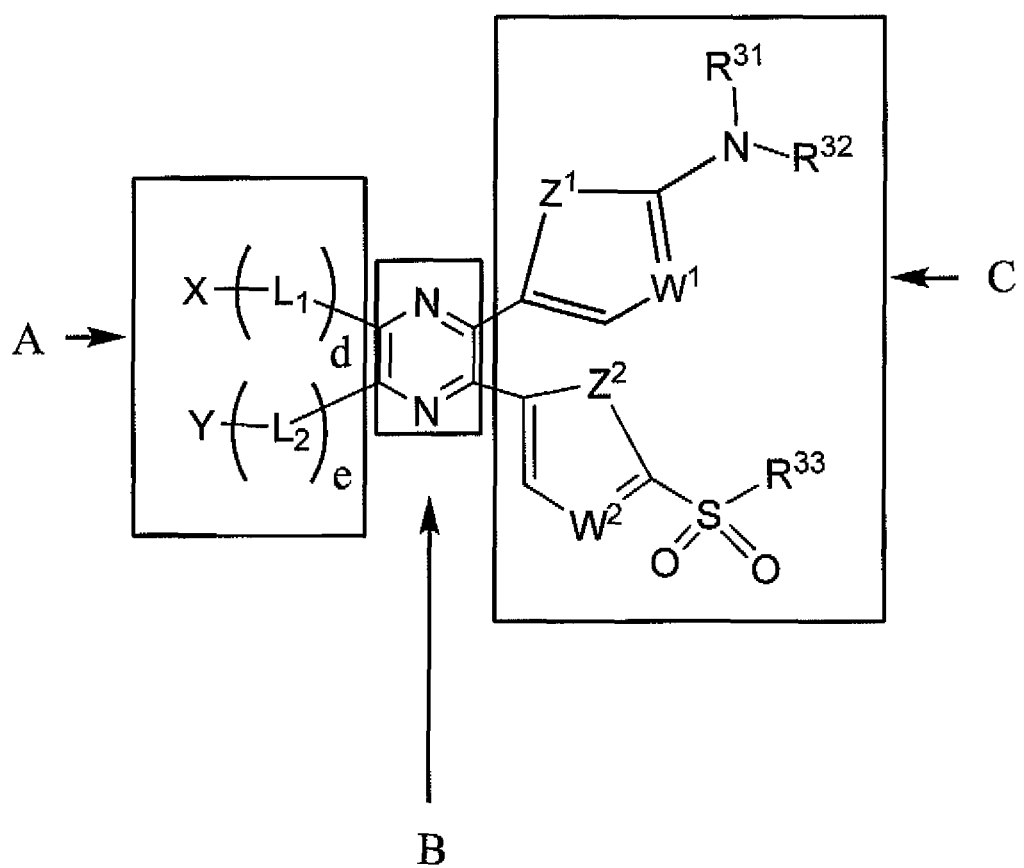

PYRAZINE DERIVATIVES FOR OPTICAL IMAGING AND THERAPY

CROSS REFERENCE TO RELATED APPLICATIONS

This application is a national stage application of PCT/US2010/031203, filed Apr. 15, 2010, which claims the benefit of U.S. Provisional Application No. 61/169,800 filed Apr. 16, 2009.

BACKGROUND

Optical agents currently play a central role in a large number of in vivo, in vitro and ex vivo clinical procedures including important diagnostic and therapeutic procedures. Photodiagnostic and phototherapeutic agents, for example, include a class of molecules capable of absorbing, emitting, or scattering electromagnetic radiation applied to a biological material, particularly in the visible and near infrared regions of the electromagnetic spectrum. This property of optical agents is used in a range of biomedical applications for visualizing, imaging or otherwise characterizing biological materials and/or achieving a desired therapeutic outcome. Recent developments in targeted administration and delivery of optical agents, and advanced systems and methods for applying and detecting electromagnetic radiation in biological environments, has considerably expanded the applicability and effectiveness of optical agents for clinical applications.

Important applications of optical agents include use for biomedical imaging and visualization. Biomedical images are generated, for example, by detecting electromagnetic radiation, nuclear radiation, acoustic waves, electrical fields, and/or magnetic fields transmitted, emitted and/or scattered by components of a biological sample. Modulation of the energy or intensity of the applied radiation yields patterns of transmitted, scattered and/or emitted radiation, acoustic waves, electrical fields or magnetic fields that contain useful anatomical, physiological, and/or biochemical information. A number of applications of biomedical imaging have matured into robust, widely used clinical techniques including planar projection and tomographic X-ray imaging, magnetic resonance imaging, ultrasound imaging, and gamma ray imaging.

Advanced optical imaging methods, such as confocal scanning laser tomography, optical coherence tomography, and endoscopic visualization, have emerged as essential molecular imaging techniques for imaging and visualizing biological processes at the organ, cellular and subcellular (e.g., molecular) levels. Established optical imaging techniques are based on monitoring spatial variations in a variety of optical parameters including the intensities, polarization states, and frequencies of transmitted, reflected, and emitted electromagnetic radiation. Given that many biological materials of interest are incompatible with ultraviolet light, research is currently directed to developing and enhancing imaging techniques using visible and near infrared (NIR) radiation having wavelengths from about 400 nm to about 900 nm. In particular, NIR light (700 nm to 900 nm) is are useful for visualizing and imaging deeper lesions than visible light because electromagnetic radiation of this wavelength range is capable of substantial penetration (e.g., up to four centimeters) in a range of biological media. Accordingly, optical imaging and visualization using optical agents has potential to provide a safer imaging technology, as compared to X-ray and other widely used nuclear medicine technologies. Applications of optical imaging for diagnosis and monitoring of the onset, progression and treatment of various disease conditions, including cancer, are well established. (D. A. Benaron and D. K. Stevenson, Optical time-of-flight and absorbance imaging of biologic media, Science, 1993, 259, pp. 1463-1466; R. F. Potter (Series Editor), Medical optical tomography: functional imaging and monitoring, SPIE Optical Engineering Press, Bellingham, 1993; G. J. Tearney et al., In vivo endoscopic optical biopsy with optical coherence tomography, Science, 1997, 276, pp. 2037-2039; B. J. Tromberg et al., Non-invasive measurements of breast tissue optical properties using frequency-domain photon migration, Phil. Trans. Royal Society London B, 1997, 352, pp. 661-668; S. Fantini et al., Assessment of the size, position, and optical properties of breast tumors in vivo by noninvasive optical methods, Appl. Opt., 1998, 37, pp. 1982-1989; A. Pelegrin et al., Photoimmunodiagnosis with antibody-fluorescein conjugates: in vitro and in vivo preclinical studies, J. Cell Pharmacol., 1992, 3, pp. 141-145).

Optical agents for in vivo and in vitro biomedical imaging, anatomical visualization and monitoring organ function are described in U.S. Pat. Nos. 5,672,333; 5,698,397; 6,167,297; 6,228,344; 6,748,259; 6,838,074; 7,011,817; 7,128,896, and 7,201,892. In this context, optical imaging agents are commonly used for enhancing signal-to-noise and resolution of optical images and extending these techniques to a wider range of biological settings and media. In addition, use of optical imaging agents having specific molecular recognition and/or tissue targeting functionality has also been demonstrated as effective for identifying, differentiating and characterizing discrete components of a biological sample at the organ, tissue, cellular, and molecular levels. Further, optical agents have been developed as tracers for real time monitoring of physiological function in a patient, including fluorescence-based monitoring of renal function. (See International Patent Publication PCT/US2007/0149478). Given their recognized utility, considerable research continues to be directed toward developing improved optical agents for biomedical imaging and visualization.

In addition to their important role in biomedical imaging and visualization, optical agents have also been extensively developed for clinical applications for phototherapy. The benefits of phototherapy using optical agents are widely acknowledged as this technique has the potential to provide efficacy comparable to radiotherapy, while entirely avoiding the exposure of non-target organs and tissue to harmful radiation. Phototherapy has been used effectively for localized superficial or endoluminal malignant and premalignant conditions. The clinical efficacy of phototherapy has also been demonstrated for the treatment of various other diseases, injuries, and disorders, including cardiovascular disorders such as atherosclerosis and vascular restenosis, inflammatory diseases, ophthalmic diseases and dermatological diseases. (See, Zheng Huang "A Review of Progress in Clinical Photodynamic Therapy", Technol Cancer Res Treat. 2005 June; 4(3): 283-293; "Photodiagnosis And Photodynamic Therapy", Brown S, Brown E A, Walker I. The present and future role of photodynamic therapy in cancer treatment. Lancet Oncol. 2004; 5:497-508; Triesscheijn M, Baas P, Schellens J H M. "Photodynamic Therapy in Oncology"; The Oncologist. 2006; 11:1034-1044; and Dougherty T J, Gamer C J, Henderson B W, Jon G, Kessel D, Korbelik M, Moan J, Peng Q. Photodynamic Therapy. J. Natl. Cancer Inst. 1998; 90:899-905). Phototherapy is carried out by administration and delivery of a photosensitizer to a target tissue (e.g., tumor, lesion, organ etc.) followed by photoactivation of the photosensitizer by absorption of applied electromagnetic radiation.

For both photodiagnostic and phototherapeutic applications, optical agents preferably exhibit a high degree of selectivity for the target tissue. Selectivity provided by optical agents facilitates effective delivery to a target tissue of interest and provides a means of differentiating different tissue classes during imaging, visualization and therapy.

Previous studies have shown that the cyclooxygenase II (COX-II) enzyme is not expressed in most normal tissues, but is expressed in response to inflammation. In addition, the COX-II enzyme is present in tumor cells. COX-II is up-regulated in colorectal cancer and many other cancers including prostate, gastric, esophageal, uterine-endometrial, pancreatic, breast, cervical, head and neck, hepatic, skin, gallbladder, lung, and ovarian cancers. As a result, COX-II inhibition by both natural dietary molecules and pharmaceutical agents is currently being studied as a primary or adjunctive treatment for these conditions.

As will be generally recognized from the foregoing, detecting the COX-II enzyme is highly desired. Early detection offers the best means of reducing the high morbidity and mortality rates of cancer patients. Advances in radiology and thermography have significantly improved cancer detection, but these methods vary in their sensitivity depending upon the size, site, and histological cancer type. One limitation of the current methods is that it is often not possible to deliver diagnostic agents selectively or specifically to the appropriate tissue or cell type. In the case of diagnostic imaging of cancer, current methods for tumor-specific imaging are hindered by imaging agents that also accumulate in normal tissues.

SUMMARY

The present invention generally provides compounds useful for imaging, diagnosing and/or treating medical conditions. Compounds provided absorb and emit spectral energy in the visible, near infrared, and/or any other wavelength range useful for optical detection in medical procedures.

More specifically, the compounds of the present invention are pyrazine derivatives, including compositions, preparations and formulations, and methods of making and using such pyrazine derivatives. Pyrazine derivatives of the invention have a pyrazine core structure and various groups bonded to the core structure. In some embodiments, pyrazine derivatives of the present invention have a pyrazine core optionally functionalized to provide useful optical, biological, pharmacokinetic and/or physical properties. Compounds of the present invention further include conjugates, for example, bioconjugates comprising a pyrazine derivative linked to one or more targeting ligands such as a peptide, protein or other ligand capable of providing molecular recognition and/or targeting functionality. Compounds of the present invention further include compositions comprising a pyrazine derivative linked to a separate photosensitizer component useful for tandem imaging and phototherapy applications.

In an embodiment, the present invention is directed to a compound of the formula (FX1):

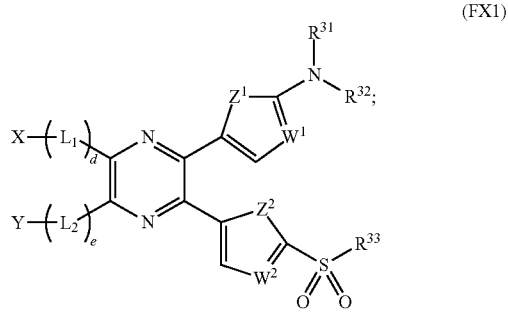
(FX1)

or a pharmaceutically acceptable salt thereof, wherein: each of $Z^1$ and $Z^2$ is independently O, S, CH=CH, —NR$^{37}$—, or CH$_2$;

each of $W^1$ and $W^2$ is independently CH or N;

each of $L^1$ and $L^2$ is independently —(CH$_2$)$_c$—, —(HCCH)$_c$—, —O—, —S—, —SO—, —SO$_2$—, —SO$_3$—, —OSO$_2$—, —NR$^{22}$—, —CO—, —COO—, —OCO—, —OCOO—, —CONR$^{23}$—, —NR$^{24}$CO—, —OCONR$^{25}$—, —NR$^{26}$COO—, —NR$^{27}$CONR$^{28}$—, or —NR$^{29}$CSNR$^{30}$—;

each c is independently an integer from 1 to 10, and each of $R^{22}$-$R^{30}$ is independently hydrogen, C$_1$-C$_{10}$ alkyl, C$_3$-C$_{10}$ cycloalkyl, or C$_5$-C$_{10}$ aryl;

each of X and Y is independently hydrogen, C$_1$-C$_{10}$ alkyl, C$_3$-C$_{10}$ cycloalkyl, C$_5$-C$_{10}$ aryl, C$_1$-C$_{10}$ acyl, C$_2$-C$_{10}$ alkenyl, C$_2$-C$_{10}$ alkynyl, C$_5$-C$_{10}$ alkylaryl, halo, halomethyl, dihalomethyl, trihalomethyl, —CN, —CO$_2$R$^1$, —CONR$^2$R$^3$, —COR$^4$, —NO$_2$, —SOR$^5$, —OSR$^{36}$, —SO$_2$R$^6$, —SO$_2$OR$^7$, —SO$_2$NR$^8$R$^9$, —PO$_3$R$^{10}$R$^{11}$, —OR$^{12}$, —SR$^{13}$, —NR$^{14}$R$^{15}$, —NR$^{16}$COR$^{17}$, or

$Z^3$ is a single bond, —CR$^{18}$R$^{19}$—, —O—, —NR$^{20}$—, —NCOR$^{21}$—, —S—, —SO—, or —SO$_2$—;

each of $R^1$ to $R^{21}$, $R^{35}$ and $R^{37}$ is independently hydrogen or C$_1$-C$_{10}$ alkyl;

each of m and n is independently 1, 2, or 3, provided that m+n≥3 if $Z^3$ is a single bond;

each of $R^{31}$ and $R^{32}$ is independently H, C$_1$-C$_6$ alkyl, halo, halomethyl, dihalomethyl, or trihalomethyl;

$R^{33}$ is H, NR$^{34}$R$^{35}$, C$_1$-C$_6$ alkyl, halo, halomethyl, dihalomethyl, or trihalomethyl;

each of $R^{34}$ and $R^{35}$ is independently hydrogen or C$_1$-C$_3$ alkyl; and each of d and e is independently 0 or 1.

In an aspect of the invention, the present invention is directed to a compound of the formula (FX1), wherein e and d are both 0. In an aspect of the invention, the present invention is directed to a compound of the formula (FX1), wherein one of X and Y is hydrogen and the other of X and Y is an electron donating group. In an aspect of the invention, the present invention is directed to a compound of the formula (FX1), wherein one of X and Y is hydrogen and the other of X and Y is an electron withdrawing group.

In an embodiment, the present invention is directed to a compound of the formula (FX2):

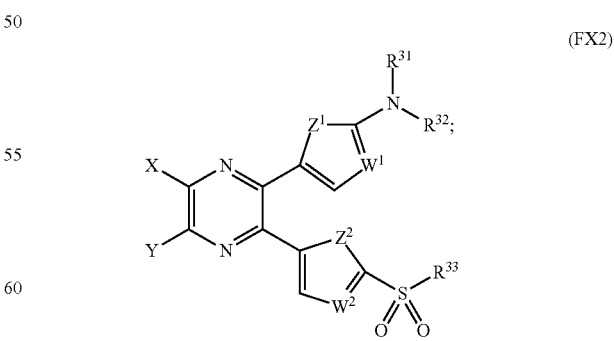
(FX2)

or a pharmaceutically acceptable salt thereof, wherein: each of $Z^1$ and $Z^2$ is independently O, S, CH=CH, —NR$^{37}$, or CH$_2$;

each of $W^1$ and $W^2$ is independently CH or N;

each of X and Y is independently hydrogen, $C_1$-$C_{10}$ alkyl, $C_3$-$C_{10}$ cycloalkyl, $C_5$-$C_{10}$ aryl, $C_1$-$C_{10}$ acyl, $C_2$-$C_{10}$ alkenyl, $C_2$-$C_{10}$ alkynyl, $C_6$-$C_{10}$ alkylaryl, halo, halomethyl, dihalomethyl, trihalomethyl, —CN, —$CO_2R^1$, —$CONR^2R^3$, —$COR^4$, —$NO_2$, —$SOR^5$, —$OSR^{36}$, —$SO_2R^6$, —$SO_2OR^7$, —$SO_2NR^8R^9$, —$PO_3R^{10}R^{11}$, —$OR^{12}$, —$SR^{13}$, —$NR^{14}R^{15}$, —$NR^{16}COR^{17}$, or

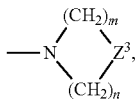

$Z^3$ is a single bond, —$CR^{18}R^{19}$—, —O—, —$NR^{20}$—, —$NCOR^{21}$—, —S—, —SO—, or —$SO_2$—;

each of $R^1$ to $R^{21}$, $R^{36}$ and $R^{37}$ is independently hydrogen or $C_1$-$C_{10}$ alkyl;

each of m and n is independently 1, 2, or 3, provided that m+n≥3 if $Z^3$ is a single bond;

each of $R^{31}$ and $R^{32}$ is independently H, $C_1$-$C_6$ alkyl, halo, halomethyl, dihalomethyl, or trihalomethyl;

$R^{33}$ is H, $NR^{34}R^{35}$, $C_1$-$C_6$ alkyl, halo, halomethyl, dihalomethyl, or trihalomethyl; and each of $R^{34}$ and $R^{35}$ is independently hydrogen or $C_1$-$C_3$ alkyl.

In an embodiment, the present invention is directed to a compound of the formula (FX3):

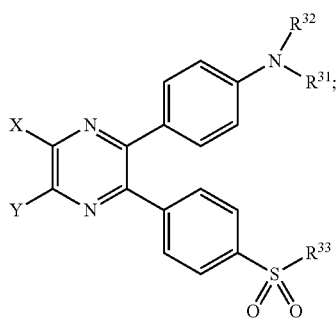

(FX3)

or a pharmaceutically acceptable salt thereof, wherein: each of X and Y is independently hydrogen, $C_1$-$C_{10}$ alkyl, $C_3$-$C_{10}$ cycloalkyl, $C_6$-$C_{10}$ aryl, $C_1$-$C_{10}$ acyl, $C_2$-$C_{10}$ alkenyl, $C_2$-$C_{10}$ alkynyl, $C_6$-$C_{10}$ alkylaryl, halo, halomethyl, dihalomethyl, trihalomethyl, —CN, —$CO_2R^1$, —$CONR^2R^3$, —$COR^4$, —$NO_2$, —$SOR^5$, —$OSR^{36}$, —$SO_2R^6$, —$SO_2OR^7$, —$SO_2NR^8R^9$, —$PO_3R^{10}R^{11}$, —$OR^{12}$, —$SR^{13}$, —$NR^{14}R^{15}$, —$NR^{15}COR^{17}$, or

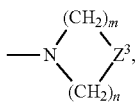

$Z^3$ is a single bond, —$CR^{18}R^{19}$—, —O—, —$NR^{20}$—, —$NCOR^{21}$—, —S—, —SO—, or —$SO_2$—;

each of $R^1$ to $R^{21}$ and $R^{36}$ is independently hydrogen or $C_1$-$C_{10}$ alkyl; each of m and n is independently 1, 2, or 3, provided that m+n≥3 if $Z^3$ is a single bond;

each of $R^{31}$ and $R^{32}$ is independently H, $C_1$-$C_6$ alkyl, halo, halomethyl, dihalomethyl, or trihalomethyl;

$R^{33}$ is H, $NR^{34}R^{35}$, $C_1$-$C_6$ alkyl, halo, halomethyl, dihalomethyl, or trihalomethyl; and each of $R^{34}$ and $R^{35}$ is independently hydrogen or $C_1$-$C_3$ alkyl.

In an embodiment, the present invention is directed to a compound of the formula (FX4):

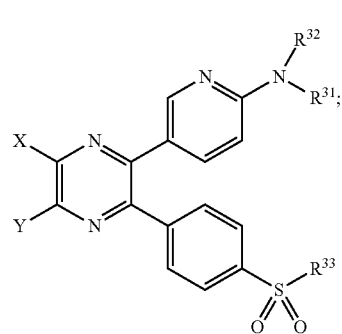

(FX4)

or a pharmaceutically acceptable salt thereof, wherein: each of X and Y is independently hydrogen, $C_1$-$C_{10}$ alkyl, $C_3$-$C_{10}$ cycloalkyl, $C_5$-$C_{10}$ aryl, $C_1$-$C_{10}$ acyl, $C_2$-$C_{10}$ alkenyl, $C_2$-$C_{10}$ alkynyl, $C_5$-$C_{10}$ alkylaryl, halo, halomethyl, dihalomethyl, trihalomethyl, —CN, —$CO_2R^1$, —$CONR^2R^3$, —$COR^4$, —$NO_2$, —$SOR^5$, —$OSR^{36}$, —$SO_2R^6$, —$SO_2OR^7$, —$SO_2NR^5R^9$, —$PO_3R^{10}R^{11}$, —$OR^{12}$, —$SR^{13}$, —$NR^{14}R^{15}$, —$NR^{16}COR^{17}$, or

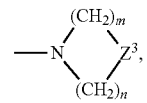

$Z^3$ is a single bond, —$CR^{18}R^{19}$—, —O—, —$NR^{20}$—, —$NCOR^{21}$—, —S—, —SO—, or —$SO_2$—;

each of $R^1$ to $R^{21}$ and $R^{36}$ is independently hydrogen or $C_1$-$C_{10}$ alkyl;

each of m and n is independently 1, 2, or 3, provided that m+n≥3 if $Z^3$ is a single bond;

each of $R^{31}$ and $R^{32}$ is independently H, $C_1$-$C_6$ alkyl, halo, halomethyl, dihalomethyl, or trihalomethyl;

$R^{33}$ is H, $NR^{34}R^{35}$, $C_1$-$C_6$ alkyl, halo, halomethyl, dihalomethyl, or trihalomethyl; and each of $R^{34}$ and $R^{35}$ is independently hydrogen or $C_1$-$C_3$ alkyl.

In an embodiment, the present invention is directed to a compound of the formula (FX5):

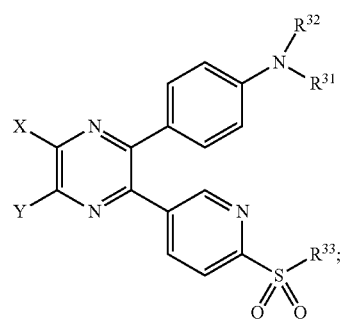

(FX5)

or a pharmaceutically acceptable salt thereof, wherein: each of X and Y is independently hydrogen, $C_1$-$C_{10}$ alkyl, $C_3$-$C_{10}$ cycloalkyl, $C_5$-$C_{10}$ aryl, $C_1$-$C_{10}$ acyl, $C_2$-$C_{10}$ alkenyl, $C_2$-$C_{10}$ alkynyl, $C_5$-$C_{10}$ alkylaryl, halo, halomethyl, dihalomethyl, trihalomethyl, —CN, —$CO_2R^1$, —$CONR^2R^3$, —$COR^4$, —$NO_2$, —$SOR^5$, —$OSR^{36}$, —$SO_2R^6$, —$SO_2OR^7$, —$SO_2NR^8R^9$, $OR^{12}$, —$SR^{13}$, —$NR^{14}R^{15}$, —$NR^{16}COR^{17}$, or

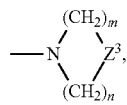

$Z^3$ is a single bond, —$CR^{18}R^{19}$—, —O—, —$NR^{20}$—, —$NCOR^{21}$—, —S—, —SO—, or —$SO_2$—;

each of $R^1$ to $R^{21}$ and $R^{36}$ is independently hydrogen or $C_1$-$C_{10}$ alkyl;

each of m and n is independently 1, 2, or 3, provided that m+n≥3 if $Z^3$ is a single bond;

each of $R^{31}$ and $R^{32}$ is independently H, $C_1$-$C_6$ alkyl, halo, halomethyl, dihalomethyl, or trihalomethyl;

$R^{33}$ is H, $NR^{34}R^{35}$, $C_1$-$C_6$ alkyl, halo, halomethyl, dihalomethyl, or trihalomethyl; and each of $R^{34}$ and $R^{35}$ is independently hydrogen or $C_1$-$C_3$ alkyl.

In an embodiment, the present invention is directed to a compound of the formula (FX6):

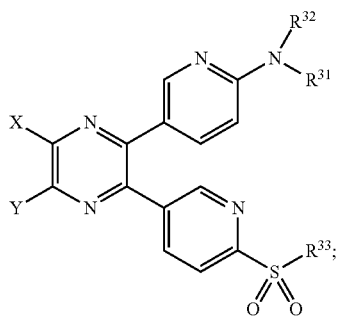

(FX6)

or a pharmaceutically acceptable salt thereof, wherein:
each of X and Y is independently hydrogen, $C_1$-$C_{10}$ alkyl, $C_3$-$C_{10}$ cycloalkyl, $C_5$-$C_{10}$ aryl, $C_1$-$C_{10}$ acyl, $C_2$-$C_{10}$ alkenyl, $C_2$-$C_{10}$ alkynyl, $C_6$-$C_{10}$ alkylaryl, halo, halomethyl, dihalomethyl, trihalomethyl, —CN, —$CO_2R^1$, —$CONR^2R^3$, —$COR^4$, —$NO_2$, —$SOR^5$, —$OSR^{36}$, —$SO_2R^6$, —$SO_2OR^7$, —$SO_2NR^8R^9$, —$PO_3R^{10}R^{11}$, —$OR^{12}$, —$SR^{13}$, —$NR^{14}R^{15}$, —$NR^{16}COR^{17}$, or

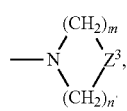

$Z^3$ is a single bond, —$CR^{18}R^{19}$—, —O—, —$NR^{20}$—, —$NCOR^{21}$—, —S—, —SO—, or —$SO_2$—;

each of $R^1$ to $R^{21}$ and $R^{36}$ is independently hydrogen or $C_1$-$C_{10}$ alkyl;

each of m and n is independently 1, 2, or 3, provided that m+n≥3 if $Z^3$ is a single bond;

each of $R^{31}$ and $R^{32}$ is independently H, $C_1$-$C_6$ alkyl, halo, halomethyl, dihalomethyl, or trihalomethyl;

$R^{33}$ is H, $NR^{34}R^{35}$, $C_1$-$C_6$ alkyl, halo, halomethyl, dihalomethyl, or trihalomethyl; and each of $R^{34}$ and $R^{35}$ is independently hydrogen or $C_1$-$C_3$ alkyl.

In an embodiment, the present invention is directed to a compound of the formula (FX7):

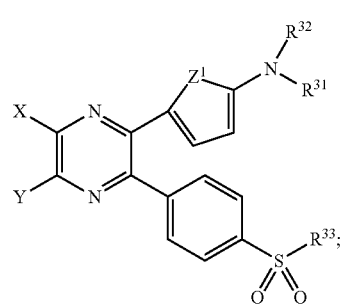

(FX7)

or a pharmaceutically acceptable salt thereof, wherein: $Z^1$ is O, S, or CH;

each of X and Y is independently hydrogen, $C_1$-$C_{10}$ alkyl, $C_3$-$C_{10}$ cycloalkyl, $C_5$-$C_{10}$ aryl, $C_r$-$C_{10}$ acyl, $C_2$-$C_{10}$ alkenyl, $C_2$-$C_{10}$ alkynyl, $C_5$-$C_{10}$ alkylaryl, halo, halomethyl, dihalomethyl, trihalomethyl, —CN, —$CO_2R^1$, —$CONR^2R^3$, —$COR^4$, —$NO_2$, —$SOR^5$, —$OSR^{35}$, —$SO_2R^6$, —$SO_2OR^7$, —$SO_2NR^8R^9$, —$PO_3R^{10}R^{11}$, —$OR^{12}$, —$SR^{13}$, —$NR^{14}R^{15}$, —$NR^{16}COR^{17}$, or

$Z^3$ is a single bond, —$CR^{18}R^{19}$—, —O—,—$NR^{20}$— $NCOR^{21}$—, —S—, —SO—, or —$SO_2$—;

each of $R^1$ to $R^{21}$ and $R^{36}$ is independently hydrogen or $C_1$-$C_{10}$ alkyl; each of m and n is independently 1, 2, or 3, provided that m+n≥3 if $Z^3$ is a single bond;

each of $R^{31}$ and $R^{32}$ is independently H, $C_1$-$C_6$ alkyl, halo, halomethyl, dihalomethyl, or trihalomethyl;

$R^{33}$ is H, $NR^{34}R^{35}$, $C_1$-$C_6$ alkyl, halo, halomethyl, dihalomethyl, or trihalomethyl; and each of $R^{34}$ and $R^{35}$ is independently hydrogen or $C_1$-$C_3$ alkyl.

In an embodiment, the present invention is directed to a compound of the formula (FX8):

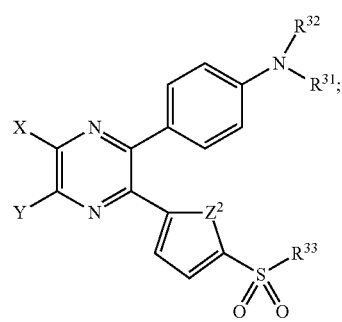

(FX8)

or a pharmaceutically acceptable salt thereof, wherein: $Z^2$ is O, S, or CH;

each of X and Y is independently hydrogen, $C_1$-$C_{10}$ alkyl, $C_3$-$C_{10}$ cycloalkyl, $C_5$-$C_{10}$ aryl, $C_1$-$C_{10}$ acyl, $C_2$-$C_{10}$ alkenyl, $C_2$-$C_{10}$ alkynyl, $C_5$-$C_{10}$ alkylaryl, halo, halomethyl, dihalomethyl, trihalomethyl, —CN, —$CO_2R^1$, —$CONR^2R^3$, —$COR^4$, —$NO_2$, —$SOR^5$, —$OSR^{36}$, —$SO_2R^6$, —$SO_2OR^7$, —$SO_2NR^8R^9$, —$PO_3R^{10}R^{11}$, —$OR^{12}$, —$SR^{13}$, —$NR^{14}R^{15}$, —$NR^{16}COR^{17}$, or

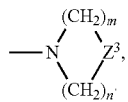

$Z^3$ is a single bond, —$CR^{18}R^{19}$—, —O—, —$NR^{20}$—, —$NCOR^{21}$—, —S—, —SO—, or —$SO_2$—;

each of $R^1$ to $R^{21}$ and $R^{36}$ is independently hydrogen or $C_1$-$C_{10}$ alkyl;

each of m and n is independently 1, 2, or 3, provided that m+n≥3 if $Z^3$ is a single bond;

each of $R^{31}$ and $R^{32}$ is independently H, $C_1$-$C_6$ alkyl, halo, halomethyl, dihalomethyl, or trihalomethyl;

$R^{33}$ is H, $NR^{34}R^{36}$, $C_1$-$C_6$ alkyl, halo, halomethyl, dihalomethyl, or trihalomethyl; and each of $R^{34}$ and $R^{35}$ is independently hydrogen or $C_1$-$C_3$ alkyl.

In an embodiment, the present invention is directed to a compound of the formula (FX9):

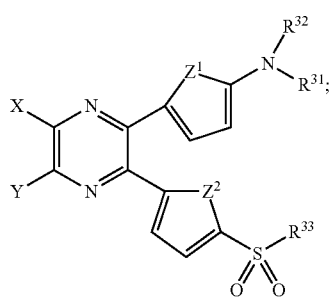

(FX9)

or a pharmaceutically acceptable salt thereof, wherein: each of $Z^1$ and $Z^2$ is independently O, S, or CH;

each of X and Y is independently hydrogen, $C_1$-$C_{10}$ alkyl, $C_3$-$C_{10}$ cycloalkyl, $C_5$-$C_{10}$ aryl, $C_1$-$C_{10}$ acyl, $C_2$-$C_{10}$ alkenyl, $C_2$-$C_{10}$ alkynyl, $C_5$-$C_{10}$ alkylaryl, halo, halomethyl, dihalomethyl, trihalomethyl, —CN, —$CO_2R^1$, —$CONR^2R^3$, —$COR^4$, —$NO_2$, —$SOR^5$, —$OSR^{36}$, —$SO_2R^6$, —$SO_2OR^7$, —$SO_2NR^8R^9$, —$PO_3R^{10}R^{11}$, —$OR^{12}$, —$SR^{13}$, —$NR^{14}R^{15}$, —$NR^{16}COR^{17}$, or

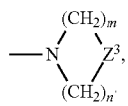

$Z^3$ is a single bond, —$CR^{18}R^{19}$—, —O—, —$NR^{20}$—, —$NCOR^{21}$—, —S—, —SO—, or —$SO_2$—;

each of $R^1$ to $R^{21}$ and $R^{36}$ is independently hydrogen or $C_1$-$C_{10}$ alkyl;

each of m and n is independently 1, 2, or 3, provided that m+n≥3 if $Z^3$ is a single bond;

each of $R^{31}$ and $R^{32}$ is independently H, $C_1$-$C_6$ alkyl, halo, halomethyl, dihalomethyl, or trihalomethyl;

$R^{33}$ is H, $NR^{34}R^{35}$, $C_1$-$C_6$ alkyl, halo, halomethyl, dihalomethyl, or trihalomethyl; and each of $R^{34}$ and $R^{35}$ is independently hydrogen or $C_1$-$C_3$ alkyl.

In an embodiment of any of the preceding formulas one of X or Y is —CN, —$CO_2R^1$, —$CONR^2R^3$, —$COR^4$, —$NO_2$, —$SOR^5$, —$SO_2R^6$, —$SO_2OR^7$, —$SO_2NR^8R^9$, or —$PO_3R^{10}R^{11}$; the other of X or Y is —$OR^{12}$, —$SR^{13}$, —$NR^{14}R^{15}$, —$NR^{16}COR^{17}$, or

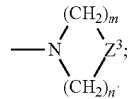

$Z^3$ is a single bond, —$CR^{18}R^{19}$—, —O—, —$NR^{26}$—, —$NCOR^{21}$—, —SO—, or —$SO_2$—; each of $R^1$ to $R^{21}$ is independently hydrogen or $C_1$-$C_6$ alkyl; and each of m and n is independently 1, 2, or 3, provided that m+n≥3 if $Z^3$ is a single bond.

In an embodiment of any of the preceding formulas one of X and Y is an electron withdrawing group and the other of X and Y is hydrogen.

In an embodiment of any of the preceding formulas one of X and Y is an electron donating group and the other of X and Y is hydrogen.

In an embodiment of any of the preceding formulas one of X or Y is —CN, —$CO_2R^1$, —$CONR^2R^3$, —$COR^4$, —$NO_2$, —$SOR^5$, —$SO_2R^6$, —$SO_2OR^7$, —$SO_2NR^8R^9$, or —$PO_3R^{10}R^{11}$; each of $R^1$ to $R^{11}$ is independently hydrogen or $C_1$-$C_6$ alkyl; and the other of X or Y is hydrogen.

In an embodiment of any of the preceding formulas one of X or Y is —$OR^{12}$, —$SR^{13}$, —$NR^{14}R^{15}$, —$NR^{16}COR^{17}$, or

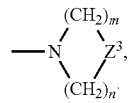

$Z^3$ is a single bond, —$CR^{18}R^{19}$, —O—, —$NR^{20}$—, —$NCOR^{21}$—, —S—, —SO—, or —$SO_2$—; each of $R^{12}$ to $R^{21}$ is independently hydrogen or $C_1$-$C_6$ alkyl; each of m and n is independently 1, 2, or 3, provided that m+n≥3 if $Z^3$ is a single bond; and the other of X or Y is hydrogen.

In an embodiment of any of the preceding formulas X and Y are both directly linked to the pyrazine core structure. In an embodiment of this aspect of the invention, d and e are both 0 (i.e., $L_1$ and $L_2$ are absent).

In an embodiment of any of the preceding formulas one of X or Y is hydrogen, —CN, —$CO_2R^1$, —$CONR^2R^3$, —$COR^4$, —$NO_2$, —$SOR^5$, —$SO_2R^6$, —$SO_2OR^7$, —$SO_2NR^8R^9$, or —$PO_3R^{10}R^{11}$; each of $R^1$ to $R^{11}$ is independently hydrogen or $C_1$-$C_3$ alkyl; and the other of X or Y is —$NR^{14}R^{15}$, and each of $R^{14}$ and $R^{15}$ is independently hydrogen or $C_1$-$C_3$ alkyl. In an embodiment of any of the preceding formulas one of X and Y is an electron withdrawing group and the other of X and Y is an electron donating group. In an embodiment, X or Y is —$NR^{14}R^{15}$, and each of $R^{14}$ and $R^{15}$ is independently hydrogen or $C_1$-$C_3$ alkyl. In an embodiment, X is an electron withdrawing group and Y is an electron donating group. In an embodiment, Y is an electron withdrawing group and X is an electron donating group. In an embodiment, X is —CN, —$CO_2R^1$, —$CONR^2R^3$, —$COR^4$, —$NO_2$, —$SOR^5$, —$SO_2R^6$, —$SO_2OR^7$, —$SO_2NR^8R^9$, or —$PO_3R^{10}R^{11}$; and Y is $OR^{12}$, —$SR^{13}$, —$NR^{14}R^{15}$, —$NR^{16}COR^{17}$, or

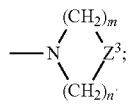

$Z^3$ is a single bond, —$CR^{18}R^{19}$—, —O—, —$NR^{20}$—, —$NCOR^{21}$—, —S—, —SO—, or —$SO_2$—; each of $R^1$ to $R^{21}$ is independently hydrogen or $C_1$-$C_6$ alkyl; each of m and n is independently 1, 2, or 3, provided that m+n≥3 if $Z^3$ is a single bond.

In an embodiment, the present invention is directed to a compound being one of formulas: (FX10), (FX11), (FX12) or (FX13):

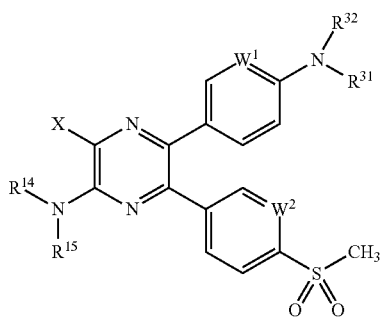

(FX10)

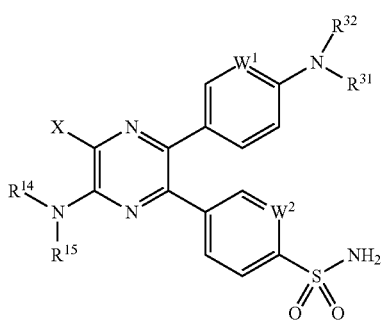

(FX11)

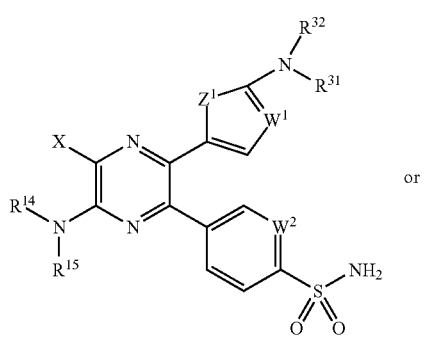

(FX12)

or

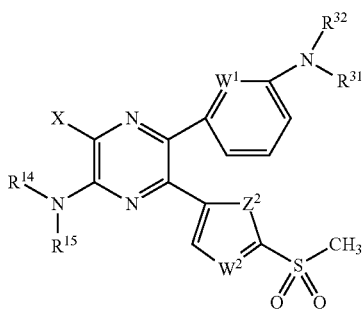

(FX13)

or a pharmaceutically acceptable salt thereof, wherein: X is independently —CN, —$CO_2R^1$, —$CONR^2R^3$, —$COR^4$, —$NO_2$, —$SOR^5$, —$SO_2R^6$, —$SO_2OR^7$, —$SO_2NR^8R^9$, or —$PO_3R^{10}R^{11}$, each of $R^1$-$R^{11}$ is independently hydrogen or $C_1$-$C_6$ alkyl; each of $R^{14}$, $R^{15}$, $R^{31}$ and $R^{32}$ is independently hydrogen or methyl; each of $W^1$ and $W^2$ is independently CH or N; and each of $Z^1$ and $Z^2$ is independently S or O.

The present invention further includes compositions comprising enantiomers, diastereomers and/or ionic forms (e.g., protonated and deprotonated forms) of the compounds of formulae (FX1)-(FX13), and related methods of using compounds of formulae (FX1)-(FX13), for example in a biomedical imaging procedure.

In an embodiment, a compound provided selectively binds to the cyclooxygenase II (COX-II) enzyme. In an embodiment, compounds provided are COX-II selective compounds. Without being bound by theory, it is believed the ring groups on the pyrazine structures described herein specifically bind to COX-II. In an embodiment, a compound provided selectively binds to a carbonic anhydrase enzyme. In an embodiment, a compound provided has a sulfonamide moiety. In an embodiment, compounds of the invention inhibit expression of COX-II.

Although Applicant does not wish to be bound by theory, the orientation of the two ring groups attached to the central pyrazine ring provide orientation of the compounds of the invention into the binding pocket of the COX-II enzyme or other desired target.

In an embodiment, provided is a compound described herein for use in a medical imaging procedure. In an embodiment, the medical imaging procedure comprises: (a) administering to a subject an effective amount of a compound provided herein under conditions sufficient for contacting the compound with the target cell, wherein the compound selectively binds to COX-II and/or carbonic anhydrase expressed by the target cell; (b) exposing the administered compound to electromagnetic radiation. In an embodiment, the procedure comprises exposing the administered compound to electromagnetic radiation having one or more wavelengths selected over a range of 350 nanometers to 1300 nanometers. In an embodiment, the procedure further comprises detecting electromagnetic radiation emitting from the compound in the subject. In an embodiment, exposing the compound administered to the subject to electromagnetic radiation increases the fluorescence intensity of the compound. In an embodiment, the procedure comprises targeting the compound to a selected organ in the subject. In an embodiment, the procedure further comprises targeting the compound to a selected tissue type in the subject. In an embodiment, the tissue type is selected from colon, prostate, gastric, esophageal, uterine, endometrial, pancreatic, breast, cervical, brain, skin, gallbladder, lung, or ovary.

Also provided is a compound for use in treating inflammation or an inflammation-associated disorder, the compound being of formula (FX1)-(FX13) described herein. Also provided is a compound for use in treating cancer or a cancer-associated disorder, the compound being of formula (FX1)-(FX13) described herein. Also provided is a pharmaceutical composition comprising a compound described herein and a pharmaceutically acceptable excipient.

In some embodiments, the present invention is directed to a pyrazine derivative having at least one electron withdrawing group (EWG) and at least one electron donating group (EDG) bonded directly or indirectly to a carbon atom of the pyrazine ring, the pyrazine ring also having two ring substituents bonded to adjacent carbon atoms of the pyrazine ring. In some embodiments, an electron withdrawing group and electron donating group are positioned on adjacent carbon atoms of the pyrazine ring core. Multiple electron withdrawing groups and/or electron donating groups on each substituent arm of the pyrazine ring are contemplated by this invention. For example, one EWG arm may comprise two, three, or more electron withdrawing groups bonded to the pyrazine core via a common linking moiety.

In some embodiments, the present invention is directed to a pyrazine derivative having one electron donating group bonded directly or indirectly to a carbon atom of the pyrazine ring, the pyrazine ring also having two ring substituents bonded to adjacent carbon atoms of the pyrazine ring. In some embodiments of the compounds of the formulas described herein, e and d are 0 and $L_1$ and $L_2$ are each a single bond so that X and Y are bonded directly to the pyrazine ring. In some embodiments, the present invention is directed to a pyrazine derivative having one electron donating group bonded directly or indirectly to a carbon atom of the pyrazine ring, the pyrazine ring also having two ring substituents bonded to adjacent carbon atoms of the pyrazine ring. In some embodiments, the present invention is directed to a compound of formula (FX1) described herein where one of X and Y is an electron donating group or an electron withdrawing group and the other of X and Y is hydrogen.

The present invention provides methods of making and using compounds, including compounds of formulas (FX1)-(FX13). Methods of this aspect of the present invention include in vivo, in vitro and ex vivo methods for biomedical and bioanalytical applications. Methods of the present invention include photodiagnostic and phototherapeutic methods, such as optical imaging, anatomical visualization, endoscopic visualization, image guided surgery, and Type 1 and Type 2 phototherapy of tumors and other lesions. For some compounds for use in vivo, in vitro or ex vivo for imaging or visualizing, the tissue, organs and/or cells is a tumor, tumor site, or other lesion.

In an embodiment, the present invention provides compounds that selectively bind to the COX-II enzyme or a portion thereof. In an embodiment, the present invention provides compounds that selectively bind to carbonic anhydrase or a portion thereof. In an embodiment, the present invention provides compounds that bind specifically to COX-II as compared to COX-1.

In an embodiment, the present invention provides methods of treating inflammation or inflammation-associated disorders, the method including administering a therapeutically-effective amount of a compound described herein to a subject in need thereof. In various embodiments, these disorders may include, but are not limited to arthritis and fever.

In an embodiment, the present invention provides methods of treating pain, the method including administering a therapeutically-effective amount of a compound described herein to a subject in need thereof.

In an embodiment, the present invention provides methods for treating cancer or a cancer-related disorder. The method includes administering a therapeutically effective amount of a compound described herein to a subject in need thereof. In various embodiments, these cancers may include colorectal, prostate, gastric, esophageal, uterine-endometrial, pancreatic, breast, cervical, head and neck, hepatic, skin, gallbladder, lung, and ovarian cancers.

In an embodiment, the present invention provides pharmaceutical compositions of a therapeutically effective amount of one or more pyrazine compounds described herein, or their pharmaceutically acceptable salts.

Without wishing to be bound by any particular theory, there can be discussion herein of beliefs or understandings of underlying principles or mechanisms relating to the invention. It is recognized that regardless of the ultimate correctness of any explanation or hypothesis, an embodiment of the invention can nonetheless be operative and useful.

Various features discussed herein in relation to one or more of the exemplary embodiments may be incorporated into any of the described aspects of the present invention alone or in any combination. Certain exemplary aspects of the invention are set forth herein. It should be understood that these aspects are presented merely to provide the reader with a brief summary of certain forms the invention might take and that these aspects are not intended to limit the scope of the invention. Indeed, the invention may encompass a variety of aspects that may not be explicitly set forth herein as would be understood by one of ordinary skill in the relevant art without undue experimentation.

BRIEF DESCRIPTION OF THE FIGURE

FIG. 1 shows exemplary functional regions of compounds of the invention. A is the optional push-pull electronic tuning region; B is the optical functionality region; and C is the binding selectivity region.

DETAILED DESCRIPTION

In general, the terms and phrases used herein have their art-recognized meaning, which can be found by reference to standard texts, journal references and contexts known to those skilled in the art. The definitions are provided to clarify their specific use in the context of the invention.

As used herein, the term "group" or "group corresponding to" may refer to a functional group of a chemical compound. Groups of the present compounds refer to an atom or a collection of atoms that are a part of the compound. Groups of the present invention may be attached to other atoms of the compound via one or more covalent bonds. Groups may also be characterized with respect to valence state. The present invention includes groups characterized as monovalent, divalent, trivalent etc. valence states. In some embodiments, for example, a group corresponding to a specified aromatic or heteroaromatic compound refers to an aryl, heteroaryl, arylene or heteroarylene group corresponding to the specified aromatic or heteroaromatic compound.

In embodiments, two substituents, such as EDG and EWG substituents, on a compound of the invention can act in what is known as a "push-pull" arrangement. In embodiments of the "push-pull" arrangement, the electron density of the compound or a portion thereof, such as an aryl or heteroaryl group, is polarized due in part to the location of an EWG and EDG on the compound. In embodiments of the "push-pull' arrangement, an EWG is positioned at a terminus of a substituent arm of the structure and an EDG is positioned at a terminus of a different substituent arm of the structure. In embodiments of the "push-pull" arrangement, an EWG is positioned at one end of a π bond and an EDG is positioned at the other end of a π bond. In an embodiment, an EWG is positioned para- to an EDG in a six-membered ring structure. In an embodiment, an EWG is positioned trans- to an EDG in an alkylene structure. In some embodiments, compounds having the "push-pull" arrangement exhibit a shift in the optical absorbance and emission spectrum as compared to compounds not having the "push-pull" arrangement.

"Optical agent" generally refers to compounds, compositions, preparations, and/or formulations that absorb, emit, or scatter electromagnetic radiation of wavelength, generally in the range of 350-900 nanometers, within a biologically relevant environment or condition. In some embodiments, optical agents of the present invention, when excited by electromagnetic radiation, undergo emission via fluorescence or phosphorescence pathways. These pathways are useful for diagnostic imaging, visualization, or organ function monitoring. Compounds belonging to this class are commonly referred to as "optical imaging agents" or "optical contrast agents." In some other embodiments, optical agents of the present invention absorb electromagnetic radiation and undergo photochemical reactions such as photofragmentation of one or more photolabile bonds to generate reactive intermediates such as nitrenes, carbene, free radicals, ions, excited species, etc. This process is useful for phototherapy of tumors or other lesions. Compounds belonging to this class are commonly referred to as "photosensitizers." The term "photosensitizer" refers to a phototherapeutic agent or a component thereof providing for photoactivation, for example, photoactivation resulting in generation of reactive species that locally kill, injure, inactivate or otherwise degrade cells (e.g., cancer cells, tumor cells, non-cancer cells, etc.).

Optical agents of the present invention can contain fluorophores. The term "fluorophore" generally refers to a component or moiety of a molecule or group which causes a molecule or group to be fluorescent. Fluorophores can be functional groups in a molecule which absorb electromagnetic radiation of first specific wavelengths and re-emit energy at second specific wavelengths. The amount and wavelengths of the emitted electromagnetic radiation depend on both the fluorophore and the chemical environment of the fluorophore. In aspects of the invention, fluorophores emit energy in the visible (e.g. 350 nm to 750 nm) and NIR regions (e.g., 750-1300 nm) of the electromagnetic spectrum.

As used herein, a "chromophore" is a compound or functional group of a compound that absorbs electromagnetic radiation, preferably for some applications electromagnetic radiation having wavelengths in the UV (e.g. 200 nm to 350 nm) or visible (e.g. 350 nm to 750 nm) of the electromagnetic spectrum.

As used herein, a "fluorophore" is a compound or functional group of a compound that absorbs electromagnetic radiation and undergoes fluorescence. Preferably for some applications a fluorophore of the compounds of the invention absorb electromagnetic radiation and generate fluorescence having wavelengths in the UV (e.g. 200 nm to 350 nm) or visible (e.g. 350 nm to 750 nm) of the electromagnetic spectrum. In some embodiment, a fluorophore of the present compounds has an appreciable quantum yield for fluorescence, such as a quantum yield over the range of 0.001 to 1, 0.01 to 1, optionally 0.1 to 1. Optical agents of the present invention include, but are not limited to, contrast agents, imaging agents, dyes, detectable agents, photosensitizer agents, photoactivators, and photoreactive agents; and conjugates, complexes, and derivatives thereof. Optical agents of the present invention include pyrazine derivatives having a pyrazine ring core structure and derivatives thereof. Some optical agents of the present invention provide detectable agents that can be administered to a subject and subsequently detected using a variety of optical techniques, including optical imaging, visualization, and other forms of optical detection.

As used herein, an "electron withdrawing group" (EWG) refers to any chemical group that draws electrons from a center, such as the pyrazine core of the present invention. In an embodiment, electron withdrawing group(s) as substituent groups for the compositions of formulae (FX1)-(FX13) are independently selected from cyano (—CN), carbonyl (—CO), carboxylate (—$CO_2R^a$), halo (—F, —Cl, —Br, —I, —At), carbamate (—$CONR^bR^c$), acyl (—$COR^d$), nitro (—$NO_2$), sulfinyl (—$SOR^e$), sulfonyl (—$SO_2R^f$)—$SO_2OR^g$, and —$PO_3R^hR^i$, wherein in the context of this description, $R^a$-$R^i$ are independently selected to enhance biological and/or physiochemical properties of the optical agents of the invention. In some instances, $R^a$-$R^i$ are independently selected from any one of a hydrogen atom, an anionic functional group (e.g., carboxylate, sulfonate, sulfate, phosphonate or phosphate) and a hydrophilic functional group (e.g., hydroxyl, carboxyl, sulfonyl, sulfonato or phosphonato). In other instances, $R^a$-$R^i$ are independently selected from hydrogen, $C_{1-10}$ alkyl, aryl, heteroaryl, —$(CH_2)_nOH$, —$(CH_2)_nCO_2H$, —$(CH_2)_nSO_3H$, —$(CH_2)_nSO_3^-$, —$(CH_2)_nOSO_3H$, —$(CH_2)_nOSO_3^-$, —$(CH_2)_nNHSO_3H$, —$(CH_2)_nNHSO_3^-$, —$(CH_2)_nPO_3H_2$, —$(CH_2)_nPO_3H^-$, —$(CH_2)_nPO_3^=$, —$(CH_2)_nOPO_3H_2$, —$(CH_2)_nOPO_3H^-$ and —$(CH_2)_nOPO_3^=$, wherein n is an integer from 1 to 10. In one example of this embodiment, the EWG(s) are independently selected from —CN, —$CO_2R^f$, —$CONR^bR^c$, —$COR^d$, —$NO_2$, and —$SO_2R^e$. An EWG is typically located at the terminus of a substituent arm of the pyrazine derivative.

As used herein, an "electron donating group" (EDG) refers to any chemical group that releases electrons to a center, such as the pyrazine core of the present invention. In an embodiment, electron donating group(s) as substituent groups for the compositions of formulae (FX1)-(FX13) are independently selected from $C_1$-$C_{10}$ alkyl, $C_3$-$C_{10}$ cycloalkyl, $C_3$-$C_{10}$ aryl, —$(CH_2)_nOH$, —$OR^j$, —$SR^k$, —$NR^lR^m$, —$N(R^n)COR^o$, and —$P(R^p)$, wherein in the context of this description, $R^j$-$R^p$ are independently selected to enhance biological and/or physiochemical properties of the optical agents of the invention and wherein n is selected from the range of 1 to 10. In some instances, $R^j$-$R^p$ are independently selected from any one of a hydrogen atom, an anionic functional group (e.g., carboxylate, sulfonate, sulfate, phosphonate or phosphate) and a hydrophilic functional group (e.g., hydroxyl, carboxyl, sulfonyl, sulfonato or phosphonato). In other instances, $R^j$-$R^p$ are independently selected from hydrogen, $C_{1-10}$ alkyl, aryl, heteroaryl, —$(CH_2)_nOH$, —$(CH_2)_nCO_2H$, —$(CH_2)_nSO_3H$, —$(CH_2)_nSO_3^-$, —$(CH_2)_nOSO_3H$, —$(CH_2)_nOSO_3^-$, —$(CH_2)_nNHSO_3H$, —$(CH_2)_nNHSO_3^-$, —$(CH_2)_nPO_3H_2$, —$(CH_2)_nPO_3H^-$, —$(CH_2)_nPO_3^=$, —$(CH_2)_nOPO_3H_2$, —$(CH_2)_nOPO_3H^-$ and —$(CH_2)_nOPO_3^=$ where n is an integer from 1 to 10. In one example of this embodiment, the EDG(s) are independently selected from —$OR^j$, —$SR^k$, —$NR^lR^m$, and —$N(R^n)COR^o$. An EDG is typically located at the terminus of a substituent arm of the pyrazine derivative.

As used herein, "selective binding" and other forms of the phrase means a preferential binding of one molecule for another in a mixture of molecules. The binding of a compound to a target can be considered selective if the binding affinity is about $1 \times 10^4$ M$^{-1}$ to about $1 \times 10^6$ M$^{-1}$ or greater. In some embodiments, compounds of the invention exhibit selective binding to COX-II or a portion thereof (also known as COX-II selective compound). In some embodiments, COX-II selective compounds bind covalently to COX-II polypeptides. In other embodiments, COX-II selective compounds bind non-covalently to COX-II polypeptides. In some embodiment, a COX-II selective compound is a COX-II selective inhibitor. A "COX-II selective inhibitor" inhibits the activity of COX-II greater than the activity of COX-1.

In an embodiment, an effective amount of a compound or composition of the invention is a therapeutically effective amount. As used herein, the phrase "therapeutically effective" qualifies the amount of compound or composition administered in the therapy. This amount achieves the goal of ameliorating, suppressing, eradicating, preventing, reducing the risk of, or delaying the onset of a targeted condition. In an embodiment, an effective amount of a compound or composition of the invention is a diagnostically effective amount. As used herein, the phrase "diagnostically effective" qualifies the amount of compound or composition administered in diagnosis, for example of a disease state or other pathological condition. The amount achieves the goal of being detectable while avoiding adverse side effects found with higher doses. In an embodiment, an active ingredient or other component is included in a therapeutically acceptable amount. In an embodiment, an active ingredient or other component is included in a diagnostically acceptable amount.

As used herein, the term "pharmaceutically" can refer to acid addition salts or base addition salts of the compounds in the present disclosure. A pharmaceutically acceptable salt is any salt which retains at least a portion of the activity of the parent compound and does not impart any significant deleterious or undesirable effect on a subject to whom it is administered and in the context in which it is administered. Pharmaceutically acceptable salts include metal complexes and salts of both inorganic and organic acids. Pharmaceutically acceptable salts include metal salts such as aluminum, calcium, iron, magnesium, manganese and complex salts. Pharmaceutically acceptable salts include, but are not limited to, acid salts such as acetic, aspartic, alkylsulfonic, arylsulfonic, axetil, benzenesulfonic, benzoic, bicarbonic, bisulfuric, bitartaric, butyric, calcium edetate, camsylic, carbonic, chlorobenzoic, -32-cilexetil, citric, edetic, edisylic, estolic, esyl, esylic, formic, fumaric, gluceptic, gluconic, glutamic, glycolic, glycolylarsanilic, hexamic, hexylresorcjnoic, hydrabamic, hydrobromic, hydrochloric, hydroiodic, hydroxynaphthoic, isethionic, lactic, lactobionic, maleic, malic, malonic, mandelic, methanesulfonic, methylnitric, methylsulfuric, mucic, muconic, napsylic, nitric, oxalic, p-nitromethanesulfonic, pamoic, pantothenic, phosphoric, monohydrogen phosphoric, dihydrogen phosphoric, phthalic, polygalactouronic, propionic, salicylic, stearic, succinic, sulfamic, sulfanlic, sulfonic, sulfuric, tannic, tartaric, teoclic, toluenesulfonic, and the like. Pharmaceutically acceptable salts may be derived from amino acids, including but not limited to cysteine. Other pharmaceutically acceptable salts may be found, for example, in Stahl et al., Handbook of Pharmaceutical Salts Properties, Selection, and Use, Wiley-VCH; Verlag Helvetica Chimica Acta, Zürich, 2002. (ISBN 3-906390-26-8).

The term "amino acid" comprises naturally occurring amino acids as well as non-naturally occurring amino acids, including amino acid analogs and derivatives. One skilled in the art will recognize that reference herein to an amino acid comprises, for example, naturally occurring proteogenic L-amino acids; D-amino acids; chemically modified amino acids such as amino acid analogs and derivatives; naturally occurring non-proteogenic amino acids, and chemically synthesized compounds having properties known in the art to be characteristic of amino acids.

The term "nucleic acid" as used herein generally refers to a molecule or strand of DNA, RNA, or derivatives or analogs thereof including one or more nucleobases. Nucleobases comprise purine or pyrimidine bases typically found in DNA or RNA (e.g., adenine, guanine, thymine, cytosine, and/or uracil). The term "nucleic acid" also comprises oligonucleotides and polynucleotides. Nucleic acids may be single-stranded molecules, or they may be double-, triple- or quadruple-stranded molecules that may comprise one or more complementary strands of a particular molecule. "Nucleic acid" includes artificial nucleic acids including peptide nucleic acids, morpholino nucleic acids, glycol nucleic acids and threose nucleic acids. Artificial nucleic acids may be capable of nucleic acid hybridization.

As used herein, "sequence" means the linear order in which monomers occur in a polymer, the order of amino acids in a polypeptide or the order of nucleotides in a polynucleotide for example.

The terms "peptide" and "polypeptide" are used synonymously in the present description, and refer to a class of compounds composed of amino acid residues chemically bonded together by amide bonds (or peptide bonds), regardless of length, functionality, environment, or associated molecule(s). Peptides and polypeptides are polymeric compounds comprising at least two amino acid residues or modified amino acid residues. Modifications can be naturally occurring or non-naturally occurring, such as modifications generated by chemical synthesis. Modifications to amino acids in peptides include, but are not limited to, phosphorylation, glycosylation, lipidation, prenylation, sulfonation, hydroxylation, acetylation, methionine oxidation, alkylation, acylation, carbamylation, iodination and the addition of cofactors. Peptides include proteins and further include compositions generated by degradation of proteins, for example by proteolyic digestion. Peptides and polypeptides can be generated by substantially complete digestion or by partial digestion of proteins. Polypeptides comprising 2 to 100 amino acid units, optionally for some embodiments 2 to 50 amino acid units and, optionally for some embodiments 2 to 20 amino acid units can be used as polypeptide targeting ligands in the invention, for example, where the polypepetide preferentially binds to proteins, peptides or other biomolecules expressed, or otherwise generated by, a target tissue, such as a tumor, precancerous tissue, site of inflammation or other lesion. Typically, the polypeptide is at least four amino acid residues in length and can range up to a full-length protein.

"Protein" refers to a class of compounds comprising one or more polypeptide chains and/or modified polypeptide chains. Proteins can be modified by naturally occurring processes such as post-translational modifications or co-translational modifications. Exemplary post-translational modifications or co-translational modifications include, but are not limited to, phosphorylation, glycosylation, lipidation, prenylation, sulfonation, hydroxylation, acetylation, methionine oxidation, the addition of cofactors, proteolysis, and assembly of proteins into macromolecular complexes. Modification of proteins can also include non-naturally occurring derivatives, analogues and functional mimetics generated by chemical synthesis. Exemplary derivatives include chemical modifications such as alkylation, acylation, carbamylation, iodination or any modification that derivatizes the protein.

As used herein, "polynucleotide" and "oligonucleotide" are used interchangeably and refer to a class of compounds composed of nucleic acid residues chemically bonded together. The invention provides optical agents having an oligonucleotide or polynucleotide targeting ligand which comprises a plurality of nucleic acid residues, such as DNA or RNA residues, and/or modified nucleic acid residues that preferentially binds to proteins, peptides or other biomolecules expressed, or otherwise generated by, a target tissue, such as a tumor, precancerous tissue, site of inflammation or other lesion. Modifications to nucleic acid residues can be naturally occurring or non-naturally occurring, such as modifications generated by chemical synthesis. Oligo- or polynucleotide targeting ligands include, for example, oligo- or poly-nucleotides comprising 1 to 100 nucleic acid units, optionally for some embodiments 1 to 50 nucleic acid units and, optionally for some embodiments 1 to 20 nucleic acid units. Polypeptide and oligonucleotide include a polymer of at least two nucleotides joined together by phosphodiester bonds and may consist of either ribonucleotides or deoxyribonucleotides.

The term "aptamer" refers to an oligo- or poly-nucleotide or polypeptide that binds to, or otherwise selectively or preferentially associates with, a specific target molecule. For example, the invention provides optical agents having an aptamer targeting ligand that preferentially binds to proteins, peptides or other biomolecules expressed, or otherwise generated by, a target tissue, such as a tumor, precancerous tissue, site of inflammation or other lesion.

"Peptidomimetic" refers to a small molecule having activity, including biological activity that resembles that of a polypeptide or is substantially the same as a polypeptide. Morphine, for example, is a peptidomimetic of endorphin peptide. In some embodiments, a peptidomimetic is a small protein-like polymer designed to mimic the functionality of a peptide. Peptidomimetics useful as targeting ligands for some compounds of the invention in the present invention include peptoids and (3-peptides. The composition and biological activity of peptidomimetics and use of peptidomimetics in targeted diagnostics and therapeutics are further described in the following references: (1) A. Giannis and T. Kolter, *Peptidomimetics for Receptor Ligands—Discovery, Development, and Medical Perspectives*, Angewandte Chemie International Edition In English, vol. 32, 1993, pg. 1244-1267 and (2) Patch, J. A. et al., *Versatile oligo(N-substituted)glycines: The many roles of peptoids in drug discovery*., Pseudo-Peptides in Drug Discovery 2004, 1-31 and P. E. Nielsen.

When used herein, the term "diagnosis", "diagnostic" and other root word derivatives are as understood in the art and are further intended to include a general monitoring, characterizing and/or identifying a state of health, physical state, or disease. The term is meant to encompass the concept of prognosis. For example, the diagnosis of cancer can include an initial determination and/or one or more subsequent assessments regardless of the outcome of a previous finding. The term does not necessarily imply a defined level of certainty regarding the prediction of a particular status or outcome.

As used herein, "administering" means that a compound or formulation thereof of the present invention, such as an optical agent, is provided to a subject, for example in a therapeutically effective amount.

Alkyl groups include straight-chain, branched and cyclic (e.g., cycloalkyl) alkyl groups. Alkyl groups include those having from 1 to 30 carbon atoms. Alkyl groups include small alkyl groups having 1 to 3 carbon atoms. Alkyl groups include medium length alkyl groups having from 4-10 carbon atoms. Alkyl groups include long alkyl groups having more than 10 carbon atoms, particularly those having 10-30 carbon atoms. The terms cycloalkyl and cyclic alkyl groups are used synonymously and specifically refer to an alkyl group having a ring structure such as a ring structure comprising 3-30 carbon atoms, optionally 3-20 carbon atoms and optionally 2-20 carbon atoms, including an alkyl group having one or more rings. Cycloalkyl groups include those having one or more rings. Cycloalkyl groups include those having a 3-, 4-, 5-, 6-, 7-, 8-, 9- or 10-member carbon ring and particularly those having a 3-, 4-, 5-, 6-, or 7-member ring. The carbon rings in cycloalkyl groups can also carry alkyl groups. Cycloalkyl groups can include bicyclic and tricyclic alkyl groups. Alkyl groups are optionally substituted. Substituted alkyl groups include among others those which are substituted with aryl groups, which in turn can be optionally substituted. Specific alkyl groups include methyl, ethyl, n-propyl, iso-propyl, cyclopropyl, n-butyl, s-butyl, t-butyl, cyclobutyl, n-pentyl, branched-pentyl, cyclopentyl, n-hexyl, branched hexyl, and cyclohexyl groups, all of which are optionally substituted. Substituted alkyl groups include fully halogenated or semihalogenated alkyl groups, such as alkyl groups having one or more hydrogens replaced with one or more fluorine atoms, chlorine atoms, bromine atoms and/or iodine atoms. Substituted alkyl groups include fully fluorinated or semifluorinated alkyl groups, such as alkyl groups having one or more hydrogens replaced with one or more fluorine atoms. An alkoxy group is an alkyl group linked to oxygen and can be represented by the formula R—O. Examples of alkoxy groups include, but are not limited to, methoxy, ethoxy, propoxy, butoxy and heptoxy. Alkoxy groups include substituted alkoxy groups wherein the alky portion of the groups is substituted as provided herein in connection with the description of alkyl groups. As used herein, MeO— refers to $CH_3O$—.

Alkenyl groups include straight-chain alkenyl groups, branched alkenyl groups, and cyclic alkenyl groups (e.g., cycloalkenyl). Alkenyl groups include those having 1, 2 or more double bonds and those in which two or more of the double bonds are conjugated double bonds. Alkenyl groups include those having from 2 to 20 carbon atoms. Alkenyl groups include small alkenyl groups having 2 to 3 carbon atoms. Alkenyl groups include medium length alkenyl groups having from 4-10 carbon atoms. Alkenyl groups include long alkenyl groups having more than 10 carbon atoms, particularly those having 10-20 carbon atoms. Cyclic alkenyl groups include those having one or more rings. Cyclic alkenyl groups include those in which a double bond is in the ring or in an alkenyl group attached to a ring. Cyclic alkenyl groups include those having a 3-, 4-, 5-, 6-, 7-, 8-, 9- or 10-member carbon ring and particularly those having a 3-, 4-, 5-, 6- or 7-member ring. The carbon rings in cyclic alkenyl groups can also carry alkyl groups. Cyclic alkenyl groups can include bicyclic and tricyclic alkyl groups. Alkenyl groups are optionally substituted. Substituted alkenyl groups include among others those which are substituted with alkyl or aryl groups, which groups in turn can be optionally substituted. Specific alkenyl groups include ethenyl, prop-1-enyl, prop-2-enyl, cycloprop-1-enyl, but-1-enyl, but-2-enyl, cyclobut-1-enyl, cyclobut-2-enyl, pent-1-enyl, pent-2-enyl, branched pentenyl, cyclopent-1-enyl, hex-1-enyl, branched hexenyl, cyclohexenyl, all of which are optionally substituted. Substituted alkenyl groups include fully halogenated or semihalogenated alkenyl groups, such as alkenyl groups having one or more hydrogens replaced with one or more fluorine atoms, chlorine atoms, bromine atoms and/or iodine atoms. Substituted alkenyl groups include fully fluorinated or semifluorinated alkenyl groups, such as alkenyl groups having one or more hydrogens replaced with one or more fluorine atoms.

Aryl groups include groups having one or more 5-, 6- or 7-member aromatic and/or heterocyclic aromatic rings. The term heteroaryl specifically refers to aryl groups having at least one 5-, 6- or 7-member heterocyclic aromatic rings. Aryl groups can contain one or more fused aromatic and heteroaromatic rings or a combination of one or more aromatic or heteroaromatic rings and one or more nonaromatic rings that may be fused or linked via covalent bonds. Heterocyclic aromatic rings can include one or more N, O, or S atoms in the ring. Heterocyclic aromatic rings can include those with one, two or three N, those with one or two 0, and those with one or two S, or combinations of one or two or three N, O or S atoms. Aryl groups are optionally substituted. Substituted aryl groups include among others those which are substituted with alkyl or alkenyl groups, which groups in turn can be optionally substituted. Specific aryl groups include phenyl groups, biphenyl groups, pyridinyl groups, and naphthyl groups, all of which are optionally substituted. Substituted aryl groups include fully halogenated or semihalogenated aryl groups, such as aryl groups having one or more hydrogens replaced with one or more fluorine atoms, chlorine atoms, bromine atoms and/or iodine atoms. Substituted aryl groups include fully fluorinated or semifluorinated aryl groups, such as aryl groups having one or more hydrogens replaced with one or more fluorine atoms. Aryl groups include, but are not limited to, aromatic group-containing or heterocylic aromatic group-containing groups corresponding to any one of the following: benzene, naphthalene, naphthoquinone, diphenylmethane, fluorene, anthracene, anthraquinone, phenanthrene, tetracene, tetracenedione, pyridine, quinoline, isoquinoline, indoles, isoindole, pyrrole, imidazole, oxazole, thiazole, pyrazole, pyrazine, pyrimidine, purine, benzimidazole, furans, benzofuran, dibenzofuran, carbazole, acridine, acridone, phenanthridine, thiophene, benzothiophene, dibenzothiophene, xanthene, xanthone, flavone, coumarin, azulene or anthracycline. As used herein, a group corresponding to the groups listed above expressly includes an aromatic or heterocyclic aromatic radical, including monovalent, divalent and polyvalent radicals, of the aromatic and heterocyclic aromatic groups listed herein are provided in a covalently bonded configuration in the compounds of the invention at any suitable point of attachment. In embodiments, aryl groups contain between 5 and 30 carbon atoms. In embodiments, aryl groups contain one aromatic or heteroaromatic six-membered ring and one or more additional five- or six-membered aromatic or heteroaromatic ring. In embodiments, aryl groups contain between five and eighteen carbon atoms in the rings. Aryl groups optionally have one or more aromatic rings or heterocyclic aromatic rings having one or more electron donating groups, electron withdrawing groups and/or targeting ligands provided as substituents.

Arylalkyl groups or alkylaryl groups are alkyl groups substituted with one or more aryl groups wherein the alkyl groups optionally carry additional substituents and the aryl groups are optionally substituted. Specific alkylaryl groups are phenyl-substituted alkyl groups, e.g., phenylmethyl groups. Alkylaryl groups are alternatively described as aryl groups substituted with one or more alkyl groups wherein the alkyl groups optionally carry additional substituents and the aryl groups are optionally substituted. Specific alkylaryl groups are alkyl-substituted phenyl groups such as methylphenyl. Substituted arylalkyl groups include fully halogenated or semihalogenated arylalkyl groups, such as arylalkyl groups having one or more alkyl and/or aryl having one or more hydrogens replaced with one or more fluorine atoms, chlorine atoms, bromine atoms and/or iodine atoms.

Optional substitution of alkyl groups includes substitution with one or more alkenyl groups, aryl groups or both, wherein the alkenyl groups or aryl groups are optionally substituted. Optional substitution of alkenyl groups includes substitution with one or more alkyl groups, aryl groups, or both, wherein the alkyl groups or aryl groups are optionally substituted. Optional substitution of aryl groups includes substitution of the aryl ring with one or more alkyl groups, alkenyl groups, or both, wherein the alkyl groups or alkenyl groups are optionally substituted.

Optional substituents for any alkyl, alkenyl and aryl group includes substitution with one or more of the following substituents, among others:

halogen, including fluorine, chlorine, bromine or iodine;
pseudohalides, including —CN;
    —$NO_2$;
    —COOR where R is a hydrogen or an alkyl group or an aryl group and more specifically where R is a methyl, ethyl, propyl, butyl, or phenyl group all of which groups are optionally substituted;
    —COR where R is a hydrogen or an alkyl group or an aryl group and more specifically where R is a methyl, ethyl, propyl, butyl, or phenyl group all of which groups are optionally substituted;
    —$CON(R)_2$ where each R, independently of each other R, is a hydrogen or an alkyl group or an aryl group and more specifically where R is a methyl, ethyl, propyl, butyl, or phenyl group all of which groups are optionally substituted; and where R and R can form a ring which can contain one or more double bonds and can contain one or more additional carbon atoms;
    —$OCON(R)_2$ where each R, independently of each other R, is a hydrogen or an alkyl group or an aryl group and more specifically where R is a methyl, ethyl, propyl, butyl, or phenyl group all of which groups are optionally substituted; and where R and R can form a ring which can contain one or more double bonds and can contain one or more additional carbon atoms;
    —$N(R)_2$ where each R, independently of each other R, is a hydrogen, or an alkyl group, or an acyl group or an aryl group and more specifically where R is a methyl, ethyl, propyl, butyl, phenyl or acetyl group, all of which are optionally substituted; and where R and R can form a ring which can contain one or more double bonds and can contain one or more additional carbon atoms;
    —SR, where R is hydrogen or an alkyl group or an aryl group and more specifically where R is hydrogen, methyl, ethyl, propyl, butyl, or a phenyl group, which are optionally substituted;
    —$SO_2R$, or —SOR where R is an alkyl group or an aryl group and more specifically where R is a methyl, ethyl, propyl, butyl, or phenyl group, all of which are optionally substituted;
    —OCOOR where R is an alkyl group or an aryl group;
    —$SO_2N(R)_2$ where each R, independently of each other R, is a hydrogen, or an alkyl group, or an aryl group all of which are optionally substituted and wherein R and R can form a ring which can contain one or more double bonds and can contain one or more additional carbon atoms;
    —OR where R is H, an alkyl group, an aryl group, or an acyl group all of which are optionally substituted. In a particular example R can be an acyl yielding —OCOR" where R" is a hydrogen or an alkyl group or an aryl group and more specifically where R" is methyl, ethyl, propyl, butyl, or phenyl groups all of which groups are optionally substituted.

Specific substituted alkyl groups include haloalkyl groups, particularly trihalomethyl groups and specifically trifluoromethyl groups. Specific substituted aryl groups include mono-, di-, tri, tetra- and pentahalo-substituted phenyl groups; mono-, di-, tri-, tetra-, penta-, hexa-, and hepta-halo-substituted naphthalene groups; 3- or 4-halo-substituted phenyl groups, 3- or 4-alkyl-substituted phenyl groups, 3- or 4-alkoxy-substituted phenyl groups, 3- or 4-RCO-substituted phenyl, 5- or 6-halo-substituted naphthalene groups. More specifically, substituted aryl groups include acetylphenyl groups, particularly 4-acetylphenyl groups; fluorophenyl groups, particularly 3-fluorophenyl and 4-fluorophenyl groups; chlorophenyl groups, particularly 3-chlorophenyl and 4-chlorophenyl groups; methylphenyl groups, particularly 4-methylphenyl groups, and methoxyphenyl groups, particularly 4-methoxyphenyl groups. As used herein, the term "polyhydroxyialkyl" refers to an alkyl group having more than one hydroxy substitution.

Selection of $R^1$-$R^{37}$ in the compounds of any one of formulas (FX1)-(FX13) establishes, at least in part, the physical, chemical, optical and/or pharmacokinetic properties of optical agents for the present compositions and methods. In some embodiments, for example $R^1$-$R^{37}$ are selected to provide optical properties supporting and enabling use of these compositions in phototherapeutic methods, such as providing one or more of the following: (i) large extinction coefficients; (ii) strong absorption in the visible and/or infrared regions of the electromagnetic spectrum (e.g., 350 to 1300 nanometers, preferably for some applications 400-900 nanometers); and (iii) a large quantum yield for the production of reactive species, such as free radicals or ions, capable of causing photoactivation initiated tissue damage. Selection of the composition of $R^1$-$R^{37}$ in the compounds of any one of formulas (FX1)-(FX13) can also be based, at least in part, on a number of pharmacokinetic and physical properties supporting effective delivery and clearance of the optical agents of the present methods and compositions. Such factors can include solubility, toxicity, immune response, biocompatibility, and bioclearance considerations. In some embodiments, any one of $R^1$-$R^{37}$ in the compounds of any one of formulas (FX1)-(FX13) comprises a hydrophilic group, a lipophilic group, hydrophobic group, or an amphiphilic group. In an embodiment, at least one of $R^1$-$R^{37}$ is a substituent comprising poly (ethylene glycol), abbreviated as PEG and —$(CH_2OCH_2)_bR$, or a derivative of PEG.

As used herein, the term "alkylene" and "alkylene group" are used synonymously and refer to a divalent group derived from an alkyl group as defined herein. The invention includes compounds having one or more alkylene groups. Alkylene groups in some embodiments in some compounds function as bridging and/or spacer groups in the present compositions. Compounds of the invention may have substituted and/or unsubstituted $C_1$-$C_{20}$ alkylene, $C_1$-$C_{10}$ alkylene and $C_{10}C_5$ alkylene groups.

As used herein, the term "cycloalkylene" and "cycloalkylene group" are used synonymously and refer to a divalent group derived from a cycloalkyl group as defined herein. Cycloalkylene groups in some embodiments in some compounds function as bridging and/or spacer groups in the present compositions. Compounds of the invention may have substituted and/or unsubstituted $C_3$-$C_{20}$ cycloalkylene, $C_3$-$C_{10}$ cycloalkylene and $C_3$-$C_5$ cycloalkylene groups.

As used herein, the term "arylene" and "arylene group" are used synonymously and refer to a divalent radical derived from an aryl group as defined herein. The invention includes compounds having one or more arylene groups. In some embodiments, an arylene is a divalent group derived from an aryl group by removal of hydrogen atoms from two intra-ring carbon atoms of an aromatic ring of the aryl group. Arylene groups in some embodiments function as bridging and/or spacer groups in the present compositions. Arylene groups in other embodiments function as chromophore, fluorphore, dye and/or imaging groups in the present compositions. Compounds of the invention include substituted and/or unsubstituted $C_3$-$C_{30}$ arylene, $C_3$-$C_{20}$ arylene, $C_3$-$C_{10}$ arylene and $C_3$-$C_5$ arylene groups.

As used herein, the term "heteroarylene" and "heteroarylene group" are used synonymously and refer to a divalent radical derived from a heteroaryl group as defined herein. The invention includes compounds having one or more heteroarylene groups. In some embodiments, an heteroarylene is a divalent group derived from an heteroaryl group by removal of hydrogen atoms from two intra-ring carbon atoms or intra-ring nitrogen atoms of a heteroaromatic ring of the heteroaryl group. Heteroarylene groups in some embodiments function as bridging and/or spacer groups in the present compositions. Heteroarylene groups in other embodiments function as chromophore, fluorphore, dye and/or imaging groups in the present compositions. Compounds of the invention include substituted and/or unsubstituted $C_3$-$C_{30}$ heteroarylene, $C_3$-$C_{20}$ heteroarylene $C_3$-$C_{10}$ heteroarylene and $C_3$-$C_5$ heteroarylene groups.

As used herein, the term "alkenylene" and "alkenylene group" are used synonymously and refer to a divalent radical derived from an alkenyl group as defined herein. The invention includes compounds having one or more alkenylene groups. Alkenylene groups in some embodiments function as bridging and/or spacer groups in the present compositions. Compounds of the invention include substituted and/or unsubstituted $C_2$-$C_{20}$ alkenylene, $C_2$-$C_{10}$ alkenylene and $C_2$-$C_5$ alkenylene groups.

As used herein, the term "cycloalkenylene" and "cycloalkenylene group" are used synonymously and refer to a divalent group derived from a cycloalkenyl group as defined herein. The invention includes compounds having one or more cycloalkenylene groups. Cycloalkenylene groups in some embodiments function as bridging and/or spacer groups in the present compositions. Compounds of the invention include substituted and/or unsubstituted $C_3$-$C_{20}$ cycloalkenylene, $C_3$-$C_{10}$ cycloalkenylene and $C_3$-$C_5$ cycloalkenylene groups.

As used herein, the term "alkynylene" and "alkynylene group" are used synonymously and refer to a divalent group derived from an alkynyl group as defined herein. The invention includes compounds having one or more alkynylene groups. Alkynylene groups in some embodiments function as bridging and/or spacer groups in the present compositions. Compounds of the invention include substituted and/or unsubstituted $C_2$-$C_{20}$ alkynylene, $C_2$-$C_{10}$ alkynylene and $C_2$-$C_5$ alkynylene groups.

As used herein, the term "halo" refers to a halogen group such as a fluoro (—F), chloro (—Cl), bromo (—Br), iodo (—I) or astato (—At).

The term "heterocyclic" refers to ring structures containing at least one other kind of atom, in addition to carbon, in the ring. Examples of such atoms include nitrogen, oxygen and sulfur. Examples of heterocyclic rings include, but are not limited to, pyrrolidinyl, piperidyl, imidazolidinyl, tetrahydrofuryl, tetrahydrothienyl, furyl, thienyl, pyridyl, quinolyl, isoquinolyl, pyridazinyl, pyrazinyl, indolyl, imidazolyl, oxazolyl, thiazolyl, pyrazolyl, pyridinyl, benzoxadiazolyl, benzothiadiazolyl, triazolyl and tetrazolyl groups. Atoms of heterocyclic rings can be bonded to a wide range of other atoms and functional groups, for example, provided as substituents.

The term "carbocyclic" refers to ring structures containing only carbon atoms in the ring. Carbon atoms of carbocyclic rings can be bonded to a wide range of other atoms and functional groups, for example, provided as substituents.

The term "alicyclic" refers to a ring that is not an aromatic ring. Alicyclic rings include both carbocyclic and heterocyclic rings.

As used herein, the term "alkoxyalkyl" refers to a substituent of the formula alkyl-O-alkyl.

Amino acids include glycine, alanine, valine, leucine, isoleucine, methionine, praline, phenylalanine, tryptophan, asparagine, glutamine, glycine, serine, threonine, serine, threonine, asparagine, glutamine, tyrosine, cysteine, lysine, arginine, histidine, aspartic acid and glutamic acid. As used herein, reference to "a side chain residue of a natural α-amino acid" specifically includes the side chains of the above-referenced amino acids.

It should be noted that as used herein and in the appended claims, the singular forms "a", "an", and "the" include plural reference unless the context clearly dictates otherwise. Thus, for example, reference to "a cell" includes a plurality of such cells and equivalents thereof known to those skilled in the art, and so forth. As well, the terms "a" (or "an"), "one or more" and "at least one" can be used interchangeably herein. It is also to be noted that the terms "comprising", "including", and "having" can be used interchangeably.

As will be clear to those of ordinary skill in the art, the groups and structures described herein as portions of the compounds of the invention may be defined as if they are separate valence-satisfied chemical structures. It is intended that when a group is described or shown as being a substituent of another group, that the group be viewed as having a valency to allow this binding to Occur.

In certain embodiments, the invention encompasses administering optical agents useful in the invention to a patient or subject. A "patient" or "subject", used equivalently herein, refers to an animal. In particular, an animal refers to a mammal, preferably a human. The subject may either: (1) have a condition able to be monitored, diagnosed, prevented and/or treated by administration of an optical agent of the invention; or (2) is susceptible to a condition that is able to be monitored, diagnosed, prevented and/or treated by administration of an optical agent of the invention.

As to any of the groups described herein which contain one or more substituents, it is understood that such groups do not contain any substitution or substitution patterns which are sterically impractical and/or synthetically non-feasible. In addition, the compounds of this invention include all stereochemical isomers arising from the substitution of these compounds.

The compounds of this invention may contain one or more chiral centers. Accordingly, this invention is intended to include racemic mixtures, diasteromers, enantiomers, tautomers and mixture enriched in one or more steroisomer. The scope of the invention as described and claimed encompasses the racemic forms of the compounds as well as the individual enantiomers and non-racemic mixtures thereof.

As used herein, "spacer moiety" refers to a component provided between the pyrazine ring of some compounds of the invention and any of X or Y, for example. In some embodiments, any one of $L_1$-$L_2$ in formulas (FX1)-(FX13) is a spacer moiety. Spacer moieties useful for some embodiments are provided between X and Y and the pyrazine ring to enhance the overall chemical, optical, physical and/or pharmacokinetic properties of an optical agent of the invention. Useful spacer moieties for compounds of the invention having formulas (FX1)-(FX13) include $C_1$-$C_{10}$ alkylene, $C_3$-$C_{10}$ cycloalkylene, $O_2$-$C_{10}$ alkenylene, $C_3$-$C_{10}$ cycloalkenylene, $C_2$-$C_{10}$ alkynylene, ethenylene, ethynylene, phenylene, 1-aza-2,5-dioxocyclopentylene, 1,4-diazacyclohexylene, —$(CH_2CH_2O)_b$—, or —$(CHOH)_a$—, wherein each of a and b is independently selected from the range of 1 to 100, optionally selected from the range of 1 to 30 and optionally selected from the range of 1 to 10. The invention includes compounds having formulas (FX1)-(FX13) that do not have a spacer moiety.

As is customary and well known in the art, hydrogen atoms in formulas (FX1)-(FX13) are not always explicitly shown, for example, hydrogen atoms bonded to the carbon atoms of aromatic and alicyclic rings are not always explicitly shown in formulas (FX1)-(FX13). The structures provided herein, for example in the context of the description of formulas (FX1)-(FX13), are intended to convey to one of reasonable skill in the art the chemical composition of compounds of the methods and compositions of the invention, and as will be understood by one of skill in the art, the structures provided do not indicate the specific bond angles between atoms of these compounds.

The invention is further detailed in the following Examples, which are offered by way of illustration and are not intended to limit the scope of the invention in any manner.

EXAMPLE 1

Methods of Use and Formulations

In an embodiment, the present invention provides pyrazine derivatives substituted with two aryl groups, the aryl substituents being bonded to adjacent carbon atoms of the pyrazine ring, which derivatives selectively bind to the COX-II enzyme. Such pyrazine derivatives can be used for detecting and imaging cells, and in particular cancer cells, that express the COX-II enzyme at a higher level than normal cells. Without being bound by a particular theory, it is understood that the aryl or other ring substituents bound to the pyrazine derivative serve to bind the COX-II enzyme whereas the pyrazine moiety functions as an optical tag that enables detection or imaging of cells that express the COX-II enzyme. In general, molecules absorbing, emitting, or scattering in the visible, NIR, or long-wavelength (UV-A, >300 nm) region of the electromagnetic spectrum are useful for optical measurement. The high sensitivity associated with fluorescence permits detection without the negative effects of radioactivity or ionizing radiation. Pyrazines are one of the few classes of small molecules having desirable photophysical properties for biomedical optical applications. These compounds are very low molecular weight fluorescent scaffold systems with surprisingly bright emission in the yellow-to-red region of the electromagnetic spectrum. Binding of the pyrazines to COX-II enhances fluorescence output by immobilizing the structure and minimizing non-radiative transitions. In addition, it is possible to induce a wavelength shift because of binding through FRET-type interactions with proximal aromatic amino acid residues in the enzyme's active site.

In an embodiment of this aspect, the invention provides a method of using an optical agent, for example, in a biomedical procedure for optically imaging or visualizing a target tissue or a class of target tissues. The present methods include tissue selective imaging and visualization methods, such as imaging or visualization of a target tissue that expresses, secretes or otherwise produces the COX-II enzyme, for example, a target tissue that expresses, secretes or otherwise produces the COX-II enzyme at an elevated level. A method of this aspect comprises the step of administering a diagnostically effective amount of a compound to a subject, wherein the compound is a compound having any of formulae (FX1)-

(FX13) or a pharmaceutical preparation thereof. In some embodiments, the method of this aspect further comprises contacting a target tissue that expresses, secretes or otherwise produces the COX-II enzyme with a diagnostically effective amount of a compound having any of formulae (FX1)-(FX13). In some embodiments, the method of this aspect further comprises contacting cancer cells, for example, cancer cells of a tumor, with a diagnostically effective amount of a compound having any of formulae (FX1)-(FX13). The present methods are useful for imaging or visualizing colorectal cancer and other cancers, including prostate cancer, gastric cancer, esophageal cancer, uterine-endometrial cancer, pancreatic cancer, breast cancer, cervical cancer, head and neck cancer, hepatic cancer, skin cancer, gallbladder cancer, ling cancer and ovarian cancer.

In methods of this aspect, the compound that has been administered to the subject then is exposed in vivo to electromagnetic radiation and electromagnetic radiation emitted or scattered by the compound is then detected. In some embodiments, fluorescence is excited from the compound (e.g., due to the electromagnetic radiation exposure), optionally via multiphoton excitation processes. In an embodiment particularly useful for imaging and/or visualization, the method of this aspect further comprises: (i) exposing a compound, such as a compound having any one of formula (FX1)-(FX13), administered to the subject to electromagnetic radiation capable of exciting emission from the compound; and (ii) measuring the emission from the compound. In some embodiments, the methods of the present invention use fluorescence excitation via exposure to light having one or more wavelengths selected over the range of 300-1300 nm. For example, optical coherence tomography (OCT) is an optical imaging technique compatible with the present compounds that allows high resolution cross sectional imaging of tissue microstructure. OCT methods use wavelengths of about 1280 nm. Use of electromagnetic radiation having one or more wavelengths selected over the range of 700 nanometers to 1300 nanometers may be useful for some in situ optical imaging methods of the present invention, including biomedical applications for imaging organs, tissue and/or tumors, anatomical visualization, optical guided surgery and endoscopic procedures. Compounds in present methods may function as contrast agents, optical probes and/or tracer elements. The methods of the present invention include in vivo, in vitro and ex vivo imaging and visualization. The present invention provides methods for a range of clinical procedures, including optical imaging methods and/or visualization guided surgery and/or endoscopic diagnostic and therapeutic procedures.

Another aspect of the invention is a method of treating inflammation or inflammation-associated disorders, the method comprising administering to a subject in need thereof a therapeutically-effective amount of a compound having any of formulae (FX1)-(FX13) or a pharmaceutical preparation thereof. These disorders may include arthritis and fever. In some embodiments, the method of this aspect further comprises contacting a target tissue that expresses, secretes or otherwise produces the COX-II enzyme with a therapeutically effective amount of a compound having any of formulae (FX1)-(FX13). In some embodiments, the method of this aspect further comprises contacting cancer cells, for example, cancer cells of a tumor, with a therapeutically effective amount of a compound having any of formulae (FX1)-(FX13). In certain embodiments, compounds of the invention are useful to treat arthritis, including but not limited to rheumatoid arthritis, spondyloarthopathies, gouty arthritis, osteoarthritis, systemic lupus erythematosus, and juvenile arthritis. Compounds of the invention are useful in the treatment of asthma, bronchitis, menstrual cramps, tendonitis, bursitis, skin-related conditions such as psoriasis, eczema, burns, and dermatitis, and from post-operative inflammation including from ophthalmic surgery such as cataract surgery and refractive surgery. Compounds of the invention also are useful to treat gastrointestinal conditions such as inflammatory bowel disease, Crohn's disease, gastritis, irritable bowel syndrome, and ulcerative-colitis. Compounds of the invention are useful in treating inflammation in vascular diseases, migraine headaches, periarteritis nodosa, thyroiditis, aplastic anemia, Hodgkin's disease, sclerodoma, rheumatic fever, type I diabetes, neuromuscular junction disease including myasthenia gravis, white matter disease including multiple sclerosis, sarcoidosis, nephrotic syndrome, Behcet's syndrome, polymyositis, gingivitis, nephritis, hypersensitivity, swelling occurring after injury, myocardial ischemia, and the like. Compounds of the invention are useful in the treatment of inflammation in ophthalmic diseases, such as retinitis, retinopathies, uveitis, ocular photophobia, and of acute injury to the eye tissue. Compounds of the invention are useful in the treatment of pulmonary inflammation, such as that associated with viral infections and cystic fibrosis. Compounds of the invention are useful for the treatment of inflammation-associated central nervous system disorders such as cortical dementias including Alzheimer's disease. Compounds of the invention are useful in the treatment of allergic rhinitis, respiratory distress syndrome, endotoxin shock syndrome, atherosclerosis, and central nervous system damage resulting from stroke, ischemia, and trauma. The term "inflammation" generally refers to a biological response of vascular tissues to harmful stimuli, such as pathogens, damaged cells, irritants, etc. Inflammation can be either acute or chronic. Acute inflammation is an initial response of the body to harmful stimuli and can be achieved by the increased movement of plasma and leukocytes from the blood into injured tissues. An inflammatory response can involve the local vascular system, the immune system, and/or various cells within the injured tissue. Prolonged inflammation, referred to as chronic inflammation, can lead to a progressive shift in the type of cells which are present at the site of inflammation can be characterized by simultaneous destruction and healing of the tissue from the inflammatory process.

Another aspect of the invention is a method of treating pain, the method including administering a therapeutically-effective amount of a compound described herein to a subject in need thereof. Compounds of the invention are useful in the treatment of pain, but not limited to postoperative pain, dental pain, muscular pain, and pain resulting from cancer.

Another aspect of the invention includes methods for the use of any compound or salt described herein in treating cancer or a cancer-related disorder. These may include, but are not limited to colorectal, prostate, gastric, esophageal, uterine-endometrial, pancreatic, breast, cervical, head and neck, hepatic, skin, gallbladder, lung, and ovarian cancers. Cancer or cancer-related disorders may include brain cancer, bone cancer, epithelial cell-derived neoplasia (epithelial carcinoma) such as basal cell carcinoma, adenocarcinoma, gastrointestinal cancer such as lip cancer, mouth cancer, esophageal cancer, small bowel cancer and stomach cancer, liver cancer, bladder cancer, renal cell carcinoma, and other known cancers that effect cells throughout the body.

"Target tissue" refers to tissue of a subject to which an optical agent is administered or otherwise contacted, for example during a biomedical procedure such as an optical imaging, phototherapy, monitoring or visualization procedure. Target tissues can be contacted with an optical agent of the invention under in vivo conditions or ex vivo conditions. Target tissues in some embodiments include cancerous tissue, cancer cells, precancerous tissue, a tumor, a lesion, a site of inflammation, or vasculature tissue. In some embodiments, a target tissue includes a melanoma cell, a breast lesion, a prostate lesion, a lung cancer cell, a colorectal cancer cell, an atherosclerotic plaque, a brain lesion, a blood vessel lesion, a lung lesion, a heart lesion, a throat lesion, an ear lesion, a rectal lesion, a bladder lesion, a stomach lesion, an intestinal lesion, an esophagus lesion, a liver lesion, a pancreatic lesion, and a solid tumor. Target tissue in some embodiments refers to a selected organ of the subject or component thereof, such as lung, heart, brain, stomach, liver, kidneys, gallbladder, pancreas, intestines, rectum, skin, colon, prostate, ovaries, breast, bladder, blood vessel, throat, ear, or esophagus.

In an embodiment, the invention provides a pharmaceutical formulation comprising a composition of the invention, such as a compound of any one of formulae (FX1)-(FX13). In an embodiment, the invention provides a method of synthesizing a composition of the invention or a pharmaceutical formulation thereof, such as a compound of any one of formulae (FX1)-(FX13). In an embodiment, a pharmaceutical formulation comprises one or more excipients, carriers, diluents, and/or other components as would be understood in the art. Preferably, the components meet the standards of the National Formulary ("NF"), United States Pharmacopoeia ("USP"; United States Pharmacopeial Convention Inc., Rockville, Md.), or Handbook of Pharmaceutical Manufacturing Formulations (Sarfaraz K. Niazi, all volumes, ISBN: 9780849317521, ISBN 10: 0849317525; CRC Press, 2004). See, e.g., United States Pharmacopeia and National Formulary (USP 30-NF 25), Rockville, Md.: United States Pharmacopeial Convention; 2007; and 2008, and each of any earlier editions; The Handbook of Pharmaceutical Excipients, published jointly by the American Pharmacists Association and the Pharmaceutical Press (Pharmaceutical Press (2005) (ISBN-10: 0853696187, ISBN-13: 978-0853696186); Merck Index, Merck & Co., Rahway, N.J.; and Gilman et al., (eds) (1996); Goodman and Gilman's: The Pharmacological Bases of Therapeutics, 8th Ed., Pergamon Press. In embodiments, the formulation base of the formulations of the invention comprises physiologically acceptable excipients, namely, at least one binder and optionally other physiologically acceptable excipients. Physiologically acceptable excipients are those known to be usable in the pharmaceutical technology sectors and adjacent areas, particularly, those listed in relevant pharmacopeias (e.g. DAB, Ph. Eur., BP, NF, USP), as well as other excipients whose properties do not impair a physiological use.

In an embodiment, an effective amount of a composition of the invention is a therapeutically effective amount. In an embodiment, an effective amount of a composition of the invention is a diagnostically effective amount. In an embodiment, an active ingredient or other component is included in a therapeutically acceptable amount. In an embodiment, an active ingredient or other component is included in a diagnostically acceptable amount.

Variations on compositions including salts and ester forms of compounds: Compounds of this invention and compounds useful in the methods of this invention include those of the compounds and formula (s) described herein and pharmaceutically-acceptable salts and esters of those compounds. In embodiments, salts include any salts derived from the acids of the formulas herein which acceptable for use in human or veterinary applications. In embodiments, the term esters refers to hydrolyzable esters of compounds of the names and structural formulas herein. In embodiments, salts and esters of the compounds of the formulas herein can include those which have the same or better therapeutic, diagnostic, or pharmaceutical (human or veterinary) general properties as the compounds of the formulas herein. In an embodiment, a composition of the invention is a compound or salt or ester thereof suitable for pharmaceutical formulations.

In an embodiment, the invention provides a method for treating a medical condition comprising administering to a subject (e.g. patient) in need thereof, a therapeutically effective amount of a composition of the invention, such as a compound of any one of formulae (FX1)-(FX13). In an embodiment, the medical condition is cancer, or various other diseases, injuries, and disorders, including cardiovascular disorders such as atherosclerosis and vascular restenosis, inflammatory diseases, ophthalmic diseases and dermatological diseases.

In an embodiment, the invention provides a medicament which comprises a therapeutically effective amount of one or more compositions of the invention, such as a compound of any one of formulae (FX1)-(FX13). In an embodiment, the invention provides a medicament which comprises a therapeutically or diagnostically effective amount of one or more compositions of the invention. In an embodiment, the invention provides a method for making a medicament for treatment of a condition described herein. In an embodiment, the invention provides a method for making a medicament for diagnosis or aiding in the diagnosis of a condition described herein. In an embodiment, the invention provides the use of one or more compositions set forth herein for the making of a medicament.

Compounds of the invention can have prodrug forms. Prodrugs of the compounds of the invention are useful in embodiments including compositions and methods. Any compound that will be converted in vivo to provide a biologically, pharmaceutically, diagnostically, or therapeutically active form of a compound of the invention is a prodrug. Various examples and forms of prodrugs are well known in the art. Examples of prodrugs are found, inter alia, in Design of Prodrugs, edited by H. Bundgaard, (Elsevier, 1985), Methods in Enzymology, Vol. 42, at pp. 309-396, edited by K. Widder, et. al. (Academic Press, 1985); A Textbook of Drug Design and Development, edited by Krosgaard-Larsen and H. Bundgaard, Chapter 5, "Design and Application of Prodrugs," by H. Bundgaard, at pp. 113-191, 1991); H. Bundgaard, Advanced Drug Delivery Reviews, Vol. 8, p. 1-38 (1992); H. Bundgaard, et al., Journal of Pharmaceutical Sciences, Vol. 77, p. 285 (1988); and Nogrady (1985) Medicinal Chemistry A Biochemical Approach, Oxford University Press, New York, pages 388-392). A prodrug, such as a pharmaceutically acceptable prodrug can represent prodrugs of the compounds of the invention which are, within the scope of sound medical judgment, suitable for use in contact with the tissues of humans and lower animals without undue toxicity, irritation, allergic response, and the like, commensurate with a reasonable benefit/risk ratio, and effective for their intended use. Prodrugs of the invention can be rapidly transformed in vivo to a parent compound of a compound described herein, for example, by hydrolysis in blood or by other cell, tissue, organ, or system processes. Further discussion is provided in T. Higuchi and V. Stella, Pro-drugs as Novel Delivery Systems, V. 14 of the A.C.S. Symposium Series, and in Edward B. Roche, ed., Bioreversible Carriers in Drug Design, American Pharmaceutical Association and Pergamon Press (1987).

The invention contemplates pharmaceutically active compounds either chemically synthesized or formed by in vivo biotransformation to compounds set forth herein.

In an embodiment, a composition of the invention is isolated or purified. In an embodiment, an isolated or purified compound can be at least partially isolated or purified as would be understood in the art. In an embodiment, the composition of the invention has a chemical purity of 95%, optionally for some applications 99%, optionally for some applications 99.9%, optionally for some applications 99.99%, and optionally for some applications 99.999% pure.

Typically, a compound of the present invention, or pharmaceutically acceptable salt thereof, is administered to a subject in a diagnostically or therapeutically effective amount. One skilled in the art generally can determine an appropriate dosage. Factors affecting a particular dosage regimen (including the amount of compound delivered, frequency of administration, and whether administration is continuous or intermittent) include, for example, the type, age, weight, sex, diet, and condition of the subject; the type of pathological condition and its severity; and the nature of the desired effect. Pharmacological considerations include pyrazine compound activity, efficacy, pharmacokinetic, and toxicology profiles of the particular pyrazine compound used; the route of administration and whether a drug delivery system is utilized; and whether the pyrazine compound is administered as part of a combination therapy (e.g., whether the agent is administered in combination with one or more active compounds, other agents, radiation, and the like).

Compositions for oral administration may be, for example, prepared in a manner such that a single dose in one or more oral preparations contains at least about 20 mg of the pyrazine compound per square meter of subject body surface area, or at least about 50, 100, 150, 200, 300, 400, or 500 mg of the pyrazine compound per square meter of subject body surface area (the average body surface area for a human is, for example, 1.8 square meters). In particular, a single dose of a composition for oral administration can contain from about 20 to about 600 mg, and in certain aspects from about 20 to about 400 mg, in another aspect from about 20 to about 300 mg, and in yet another aspect from about 20 to about 200 mg of the pyrazine compound per square meter of subject body surface area. Compositions for parenteral administration can be prepared in a manner such that a single dose contains at least about 20 mg of the pyrazine compound per square meter of subject body surface area, or at least about 40, 50, 100, 150, 200, 300, 400, or 500 mg of the pyrazine compound per square meter of subject body surface area. In particular, a single dose in one or more parenteral preparations contains from about 20 to about 500 mg, and in certain aspects from about 20 to about 400, and in another aspect from about 20 to about 400 mg, and in yet another aspect from about 20 to about 350 mg of the pyrazine compound per square meter of subject body surface area. It should be recognized that these oral and parenteral dosage ranges represent generally preferred dosage ranges, and are not intended to limit the invention. The dosage regimen actually employed can vary widely, and, therefore, can deviate from the generally preferred dosage regimen. It is contemplated that one skilled in the art will tailor these ranges to the individual subject.

Toxicity and therapeutic efficacy of such compounds and bioconjugates can be determined by standard pharmaceutical procedures in cell cultures or experimental animals for determining the $LD_{50}$ (the dose lethal to 50% of the population) and the $ED_{50}$, (the dose therapeutically effective in 50% of the population). The dose ratio between toxic and therapeutic effects is the therapeutic index that can be expressed as the ratio $LD_{50}/ED_{50}$. Compounds and bioconjugates that exhibit large therapeutic indices are preferred. While compounds and bioconjugates exhibiting toxic side effects can be used, care should be taken to design a delivery system that targets such compounds and bioconjugates to the site affected by the disease or disorder in order to minimize potential damage to unaffected cells and reduce side effects.

Data obtained from cell culture assays and animal studies can be used in formulating a range of dosages for use in humans and other mammals. The dosage of such compounds and bioconjugates lies preferably within a range of circulating plasma or other bodily fluid concentrations that include the $ED_{50}$ and provides clinically efficacious results (i.e., reduction in disease symptoms). The dosage can vary within this range depending upon the dosage form employed and the route of administration utilized. For any compound and bioconjugate of the present invention, the therapeutically effective amount can be estimated initially from cell culture assays. A dosage can be formulated in animal models to achieve a circulating plasma concentration range that includes the $ED_{50}$ (the concentration of the test compound that achieves a half-maximal inhibition of symptoms) as determined in cell culture. Such information can be used to more accurately determine useful dosages in humans and other mammals. Compound and bioconjugate levels in plasma can be measured, for example, by high performance liquid chromatography.

An amount of a compound or bioconjugate that can be combined with a pharmaceutically acceptable carrier to produce a single dosage form will vary depending upon the patient treated and the particular mode of administration. It will be appreciated by those skilled in the art that the unit content of a compound/bioconjugate contained in an individual dose of each dosage form need not in itself constitute a therapeutically effective amount, as the necessary therapeutically effective amount could be reached by administration of a number of individual doses. The selection of dosage depends upon the dosage form utilized, the condition being treated, and the particular purpose to be achieved according to the determination of those skilled in the art.

The dosage and dosage regime for treating a disease or condition can be selected in accordance with a variety of factors, including the type, age, weight, sex, diet and/or medical condition of the patient, the route of administration, pharmacological considerations such as activity, efficacy, pharmacokinetic and/or toxicology profiles of the particular compound/bioconjugate employed, whether a compound/bioconjugate delivery system is utilized, and/or whether the compound/bioconjugate is administered as a pro-drug or part of a drug combination. Thus, the dosage regime actually employed can vary widely from subject to subject, or disease to disease and different routes of administration can be employed in different clinical settings.

The identified compounds/bioconjugates monitor, treat, inhibit, control and/or prevent, or at least partially arrest or partially prevent, diseases and conditions of interest and can be administered to a subject at therapeutically effective amounts and optionally diagnostically effective amounts. Compositions/formulations of the present invention comprise a therapeutically effective amount (which can optionally include a diagnostically effective amount) of at least one compound or bioconjugate of the present invention. Subjects receiving treatment that includes a compound/bioconjugate of the invention are preferably animals (e.g., mammals, reptiles and/or avians), more preferably humans, horses, cows, dogs, cats, sheep, pigs, and/or chickens, and most preferably humans.

As indicated above, it is contemplated that the pyrazine compounds and pharmaceutically acceptable salts of the present invention may be used as part of a combination. The term "combination" means the administration of two or more compounds directed to the target condition. The treatments of the combination generally may be co-administered in a simultaneous manner. Two compounds can be co-administered as, for example: (a) a single formulation (e.g., a single capsule) having a fixed ratio of active ingredients; or (b) multiple, separate formulations (e.g., multiple capsules) for each compound. The treatments of the combination may alternatively (or additionally) be administered at different times.

It is further contemplated that the pyrazine compounds and salts of this invention can be used in the form of a kit that is suitable for use in performing the methods described herein, packaged in a container. The kit can contain the pyrazine compound or compounds and, optionally, appropriate diluents, devices or device components suitable for administration and instructions for use in accordance with the methods of the present invention. The devices can include parenteral injection devices, such as syringes or transdermal patch or the like. Device components can include cartridges for use in injection devices and the like. In one aspect, the kit includes a first dosage form including a pyrazine compound or salt of this invention and a second dosage form including another active ingredient in quantities sufficient to carry out the methods of the present invention. The first dosage form and the second dosage form together can include a therapeutically effective amount of the compounds for treating the targeted condition(s).

This invention also is directed, in part, to pharmaceutical compositions including a therapeutically effective amount of a compound or salt of this invention, as well as processes for making such compositions. Such compositions generally include one or more pharmaceutically acceptable carriers (e.g., excipients, vehicles, auxiliaries, adjuvants, diluents) and may include other active ingredients. Formulation of these compositions may be achieved by various methods known in the art. A general discussion of these methods may be found in, for example, Hoover, John E., Remington's Pharmaceutical Sciences (Mack Publishing Co., Easton, Pa.: 1975). See also, Lachman, L., eds., Pharmaceutical Dosage Forms (Marcel Decker, New York, N.Y., 1980).

The preferred composition depends on the route of administration. Any route of administration may be used as long as the target of the compound or pharmaceutically acceptable salt is available via that route. Suitable routes of administration include, for example, oral, parenteral, inhalation, rectal, nasal, topical (e.g., transdermal and intraocular), intravesical, intrathecal, enteral, pulmonary, intralymphatic, intracavital, vaginal, transurethral, intradermal, aural, intramammary, buccal, orthotopic, intratracheal, intralesional, percutaneous, endoscopical, transmucosal, sublingual, and intestinal administration.

Pharmaceutically acceptable carriers that may be used in conjunction with the compounds of the invention are well known to those of ordinary skill in the art. Carriers can be selected based on a number of factors including, for example, the particular pyrazine compound(s) or pharmaceutically acceptable salt(s) used; the compound's concentration, stability, and intended bioavailability; the condition being treated; the subject's age, size, and general condition; the route of administration; etc. A general discussion related to carriers may be found in, for example, J. G. Nairn, Remington's Pharmaceutical Science, pp. 1492-1517 (A. Gennaro, ed., Mack Publishing Co., Easton, Pa. (1985)).

As used herein, the term "controlled-release component" refers to an agent that facilitates the controlled-release of a compound including, but not limited to, polymers, polymer matrices, gels, permeable membranes, liposomes, microspheres, or the like, or any combination thereof. Methods for producing compounds in combination with controlled-release components are known to those of skill in the art.

As used herein, the term "pharmaceutically acceptable" means approved by a regulatory agency of an appropriate federal or state government; or listed in the U.S. Pharmacopoeia or other generally recognized pharmacopoeia for use in animals, and more particularly in humans; or does not impart significant deleterious or undesirable effect on a subject to whom it is administered and in the context in which it is administered.

Solid dosage forms for oral administration include, for example, capsules, tablets, gelcaps, pills, dragees, troches, powders, granules, and lozenges. In such solid dosage forms, the compounds or pharmaceutically acceptable salts thereof can be combined with one or more pharmaceutically acceptable carriers. The compounds and pharmaceutically acceptable salts thereof can be mixed with carriers including, but not limited to, lactose, sucrose, starch powder, corn starch, potato starch, magnesium carbonate, microcrystalline cellulose, cellulose esters of alkanoic acids, cellulose alkyl esters, talc, stearic acid, magnesium stearate, magnesium oxide, sodium and calcium salts of phosphoric and sulfuric acids, sodium carbonate, agar, mannitol, sorbitol, sodium saccharin, gelatin, acacia gum, alginic acid, sodium alginate, tragacanth, colloidal silicon dioxide, croscarmellose sodium, polyvinylpyrrolidone, and/or polyvinyl alcohol, and then tableted or encapsulated for convenient administration. Such capsules or tablets can contain a controlled-release formulation, as can be provided in a dispersion of the compound or salt in hydroxypropylmethyl cellulose. In the case of capsules, tablets, and pills, the dosage forms also can include buffering agents, such as sodium citrate, or magnesium or calcium carbonate or bicarbonate. Tablets and pills additionally can, for example, include a coating (e.g., an enteric coating) to delay disintegration and absorption. The concentration of the pyrazine compound in a solid oral dosage form can be from about 5 to about 50%, and in certain aspects from about 8 to about 40%, and in another aspect from about 10 to about 30%) by weight based on the total weight of the composition.

Liquid dosage forms of the compounds of the present invention for oral administration include, for example, pharmaceutically acceptable emulsions, solutions, suspensions, syrups, and elixirs containing inert diluents commonly used in the art (e.g., water). Such compositions also can include adjuvants, such as wetting, emulsifying, suspending, flavoring (e.g., sweetening), and/or perfuming agents. The concentration of the pyrazine compound in the liquid dosage form can be from about 0.01 to about 5 mg, and in certain aspects from about 0.01 to about 1 mg, and in another aspect from about 0.01 to about 0.5 mg per ml of the composition. Low concentrations of the compounds of the present invention in liquid dosage form can be prepared in the case that the pyrazine compound is more soluble at low concentrations. Techniques for making oral dosage forms useful in the present invention are generally described in, for example, Modern Pharmaceutics, Chapters 9 and 10 (Banker & Rhodes, Editors (1979)). See also, Lieberman et al., Pharmaceutical Dosage Forms Tablets (1981). See also, Ansel, Introduction to Pharmaceutical Dosage Forms (2nd Edition (1976)).

In some aspects of the present invention, tablets or powders for oral administration can be prepared by dissolving the pyrazine compound in a pharmaceutically acceptable solvent capable of dissolving the compound to form a solution and then evaporating when the solution is dried under vacuum. A carrier can also be added to the solution before drying. The resulting solution can be dried under vacuum to form a glass. The glass can then be mixed with a binder to form a powder. This powder may be mixed with fillers or other conventional tableting agents, and then processed to form a tablet. Alternatively, the powder may be added to a liquid carrier to form a solution, emulsion, suspension, or the like.

In some aspects, solutions for oral administration are prepared by dissolving the pyrazine compound in a pharmaceutically acceptable solvent capable of dissolving the compound to form a solution. An appropriate volume of a carrier is added to the solution while stirring to form a pharmaceutically acceptable solution for oral administration.

In some embodiments, a liposome or micelle can be utilized as a carrier or vehicle for the composition.

In one embodiment, the pyrazine compounds are formulated as nanoparticles or microparticles. Use of such nanoparticle or microparticle formulations can be beneficial for some applications to enhance delivery, localization, target specificity, administration, etc. of the pyrazine compound. Potentially useful nanoparticles and microparticles include, but are not limited to, micelles, liposomes, microemulsions, nanoemulsions, vesicles, tubular micelles, cylindrical micelles, bilayers, folded sheets structures, globular aggregates, swollen micelles, inclusion complex, encapsulated droplets, microcapsules, nanocapsules or the like. As will be understood by those having skill in the art, the pyrazine compounds can be located inside the nanoparticle or microparticle, within a membrane or wall of the nanoparticle or microparticle, or outside of (but bonded to or otherwise associated with) the nanoparticle or microparticle. The agent formulated in nanoparticles or microparticles can be administered by any of the routes described elsewhere herein. In a formulation applied topically, the pyrazine compound is slowly released over time. In an injectable formulation, the liposome, micelle, capsule, etc., circulates in the bloodstream and is delivered to the desired site (e.g., target tissue).

Preparation and loading of nanoparticles and microparticles are well known in the art. As one example, liposomes can be prepared from dipalmitoyl phosphatidylcholine (DPPC) or egg phosphatidylcholine (PC) because this lipid has a low heat transition. Liposomes are made using standard procedures as known to one skilled in the art (e.g., Braun-Falco et al., (Eds.), Griesbach Conference, Liposome Dermatics, Springer-Verlag, Berlin (1992), pp. 69 81; 91 117. Polycaprolactone, poly(glycolic) acid, poly(lactic) acid, polyanhydride or lipids can be formulated as microspheres. As an illustrative example, the present pyrazine compounds can be mixed with polyvinyl alcohol (PVA), the mixture then dried and coated with ethylene vinyl acetate, then cooled again with PVA. In a liposome, the present pyrazine compounds can be within one or both lipid bilayers, in the aqueous between the bilayers, or within the center or core. Liposomes can be modified with other molecules and lipids to form a cationic liposome. Liposomes can also be modified with lipids to render their surface more hydrophilic which increases their circulation time in the bloodstream. The thus-modified liposome has been termed a "stealth" liposome, or a long-lived liposome, as described in U.S. Pat. No. 6,258,378, and in Stealth Liposomes, Lasic and Martin (Eds.) 1995 CRC Press, London. Encapsulation methods include detergent dialysis, freeze drying, film forming, injection, as known to one skilled in the art and disclosed in, for example, U.S. Pat. No. 6,406,713. Optionally, the present compositions and methods include a micelle delivery system, for example, involving one or more PEG-based amphiphilic polymers developed for drug delivery including: PEG-poly(α-caprolactone), PEG-poly(amino acid), PEG-polylactide or PEG-phospholipid constructs; a cross linked poly(acrylic acid) polymer system, a phospholipid-based system and/or block copolymer systems comprising one or more of the following polymer blocks: a poly(lactic acid) polymer block; a poly (propylene glycol) polymer block; a poly(amino acid) polymer block; a poly(ester) polymer block; a poly (□caprolactone) polymer block; a poly(ethylene glycol) block, a poly (acrylic acid) block; a polylactide block; a polyester block; a polyamide block; a polyanhydride block; a polyurethane block; a polyimine block; a polyurea block; a polyacetal block; a polysaccharide block; and a polysiloxane block.

"Parenteral administration" includes subcutaneous injections, intravenous injections, intraarterial injections, intraorbital injections, intracapsular injections, intraspinal injections, intraperitoneal injections, intramuscular injections, intrasternal injections, and infusion. Dosage forms suitable for parenteral administration include solutions, suspensions, dispersions, emulsions, and any other dosage form that can be administered parenterally.

Compounds and bioconjugates of the present invention can be formulated for parenteral administration by injection (e.g., by bolus injection or continuous infusion). Formulations for injection can be presented in unit dosage form in ampoules or in multi-dose containers with an optional preservative added. The parenteral preparation can be enclosed in ampoules, disposable syringes or multiple dose vials made of glass, plastic or the like. The formulation can take such forms as suspensions, solutions or emulsions in oily or aqueous vehicles, and can contain formulatory agents such as suspending, stabilizing and/or dispersing agents.

For example, a parenteral preparation can be a sterile injectable solution or suspension in a nontoxic parenterally acceptable diluent or solvent (e.g., as a solution in 1,3-butanediol). Among the acceptable vehicles and solvents that can be employed are water, Ringer's solution, and isotonic sodium chloride solution. In addition, sterile, fixed oils are conventionally employed as a solvent or suspending medium. For this purpose any bland fixed oil can be employed including synthetic mono- or di-glycerides. In addition, fatty acids such as oleic acid can be used in the parenteral preparation.

Alternatively, compounds and bioconjugates of the present invention can be formulated in powder form for constitution with a suitable vehicle, such as sterile pyrogen-free water, before use. For example, a compound/bioconjugate suitable for parenteral administration can include a sterile isotonic saline solution containing between 0.1 percent and 90 percent weight per volume of the compound/bioconjugate. By way of example, a solution can contain from about 5 percent to about 20 percent, more preferably from about 5 percent to about 17 percent, more preferably from about 8 to about 14 percent, and still more preferably about 10 percent weight per volume of the compound/bioconjugate. The solution or powder preparation can also include a solubilizing agent and a local anesthetic such as lignocaine to ease pain at the site of the injection. Other methods of parenteral delivery of compounds/bioconjugates will be known to the skilled artisan and are within the scope of the invention.

A compound/bioconjugate of the invention can be formulated as a depot preparation. Such long-acting formulations can be administered by implantation (e.g., subcutaneously or intramuscularly) or by intramuscular injection. Accordingly, the compound/bioconjugate can be formulated with suitable polymeric or hydrophobic materials such as an emulsion in an acceptable oil or ion exchange resin, or as sparingly soluble derivatives such as a sparingly soluble salt. Other methods of depot delivery of compounds/bioconjugates will be known to the skilled artisan and are within the scope of the invention.

For topical application, a compound/bioconjugate can be combined with a pharmaceutically acceptable carrier so that an effective dosage is delivered, based on the desired activity ranging from an effective dosage, for example, of 1.0 μM to 1.0 mM. In one aspect of the invention, a topical formulation of a compound/bioconjugate can be applied to the skin. The pharmaceutically acceptable carrier can be in the form of, for example, and not by way of limitation, an ointment, cream, gel, paste, foam, aerosol, suppository, pad or gelled stick.

A topical formulation can include a therapeutically effective amount of a compound/bioconjugate in an ophthalmologically acceptable excipient such as buffered saline, mineral oil, vegetable oils such as corn or arachis oil, petroleum jelly, Miglyol 182, alcohol solutions, or liposomes or liposome-like products. Any of these formulations of such compounds/bioconjugates can include preservatives, antioxidants, antibiotics, immunosuppressants, and other biologically or pharmaceutically effective agents that do not exert a significant detrimental effect on the compound/bioconjugate. Other methods of topical delivery of compounds/bioconjugates will be known to the skilled artisan and are within the scope of the invention.

Compounds/bioconjugates of the invention can be formulated in rectal formulations such as suppositories or retention enemas that include conventional suppository bases such as cocoa butter or other glycerides and/or binders and/or carriers such as triglycerides, microcrystalline cellulose, gum tragacanth or gelatin. Rectal formulations can contain a compound/bioconjugate in the range of 0.5% to 10% by weight, for example. Other methods of rectal delivery of compounds/bioconjugates will be known to the skilled artisan and are within the scope of the invention.

Various other delivery systems are known in the art and can be used to administer the compounds/bioconjugates of the invention. Moreover, these and other delivery systems can be combined and/or modified to promote optimization of the administration of compounds/bioconjugates of the present invention. Exemplary formulations that include compounds/bioconjugates of the present invention are described elsewhere herein (the compounds/bioconjugates of the present invention are indicated as the active ingredient, but those of skill in the art will recognize that pro-drugs and compound combinations are also meant to be encompassed by this term).

Controlled-release (or sustained-release) preparations can be formulated to extend the activity of a compound/bioconjugate and reduce dosage frequency. Controlled-release preparations can also be used to effect the time of onset of action or other characteristics, such as blood levels of the compound/bioconjugate, and consequently affect the occurrence of side effects.

Controlled-release preparations can be designed to initially release an amount of a compound/bioconjugate that produces the desired therapeutic effect, and gradually and continually release other amounts of the compound/bioconjugate to maintain the level of therapeutic effect over an extended period of time. In order to maintain a near-constant level of a compound/bioconjugate in the body, the compound/bioconjugate can be released from the dosage form at a rate that will replace the amount of compound/bioconjugate being metabolized and/or excreted from the body. The controlled-release of a compound/bioconjugate can be stimulated by various inducers, e.g., change in pH, change in temperature, enzymes, water, and/or other physiological conditions or molecules.

Controlled-release systems can include, for example, an infusion pump which can be used to administer the compound/bioconjugate in a manner similar to that used for delivering insulin or chemotherapy to the body generally, or to specific organs or tumors. Typically, using such a system, the compound/bioconjugate is administered in combination with a biodegradable, biocompatible polymeric implant that releases the compound/bioconjugate over a controlled period of time at a selected site. Examples of polymeric materials include polyanhydrides, polyorthoesters, polyglycolic acid, polylactic acid, polyethylene vinyl acetate, and copolymers and combinations thereof. In addition, a controlled release system can be placed in proximity of a therapeutic target (e.g., organ, tissue, or group of cells), thus requiring only a fraction of a systemic dosage.

Compounds/bioconjugates of the invention can be administered by other controlled-release means or delivery devices that are well known to those of ordinary skill in the art. These include, for example, hydropropylmethyl cellulose, other polymer matrices, gels, permeable membranes, osmotic systems, multilayer coatings, microparticles, liposomes, microspheres, or the like, or a combination of any of the above to provide the desired release profile in varying proportions. Other methods of controlled-release delivery of compounds/bioconjugates will be known to the skilled artisan and are within the scope of the invention.

Injectable preparations (e.g., sterile injectable aqueous or oleaginous suspensions) can be formulated according to the known art using suitable dispersing, wetting agents, and/or suspending agents. Acceptable vehicles for parenteral use include both aqueous and nonaqueous pharmaceutically-acceptable solvents. Suitable pharmaceutically acceptable aqueous solvents include, for example, water, saline solutions, dextrose solutions (e.g., such as DW5), electrolyte solutions, etc.

Suitable pharmaceutically-acceptable nonaqueous solvents include, but are not limited to, the following (as well as mixtures thereof): alcohols (these include, for example, σ-glycerol formal, β-glycerol formal, 1,3-butyleneglycol, aliphatic or aromatic alcohols having from 2 to about 30 carbons (e.g., methanol, ethanol, propanol, isopropanol, butanol, t-butanol, hexanol, octanol, amylene hydrate, benzyl alcohol, glycerin (glycerol), glycol, hexylene, glycol, tetrahydrofuranyl alcohol, cetyl alcohol, and stearyl alcohol), fatty acid esters of fatty alcohols (e.g., polyalkylene glycols, such as polypropylene glycol and polyethylene glycol), sorbitan, sucrose, and cholesterol); amides (these include, for example, dimethylacetamide (DMA), benzyl benzoate DMA, dimethylformamide, N-hydroxyethyO-lactamide, N,N-dimethylacetannide-amides, 2-pyrrolidinone, 1-methyl-2-pyrrolidinone, and polyvinylpyrrolidone); esters (these include, for example, acetate esters (e.g., monoacetin, diacetin, and triacetin), aliphatic and aromatic esters (e.g., ethyl caprylate or octanoate, alkyl oleate, benzyl benzoate, or benzyl acetate), dimethylsulfoxide (DMSO), esters of glycerin (e.g., mono, di, and tri-glyceryl citrates and tartrates), ethyl benzoate, ethyl acetate, ethyl carbonate, ethyl lactate, ethyl oleate, fatty acid esters of sorbitan, glyceryl monostearate, glyceride esters (e.g., mono, di, or tri-glycerides), fatty acid esters (e.g., isopropyl myristrate), fatty acid derived PEG esters (e.g., PEG-hydroxyoleate and PEG-hydroxystearate), N-methylpyrrolidinone, pluronic 60, polyoxyethylene sorbitol oleic polyesters (e.g., poly(ethoxylated)$_{30-60}$ sorbitol poly (oleate)$_{2-4}$, poly(oxyethylene)$_{15-20}$ monooleate, poly(oxyethylene)$_{15-20}$ mono 12-hydroxystearate, and poly(oxyethylene)$_{15-20}$ mono ricinoleate), polyoxyethylene sorbitan esters (e.g., polyoxyethylene-sorbitan monooleate, polyoxyethylene-sorbitan monopalmitate, polyoxyethylene-sorbitan monolaurate, polyoxyethylene-sorbitan monostearate, and POLYSORBATE 20, 40, 60, and 80 (from ICI Americas, Wilmington, Del.)), polyvinylpyrrolidone, alkyleneoxy modified fatty acid esters (e.g., polyoxyl 40 hydrogenated castor oil and polyoxyethylated castor oils, such as CREMOPHOR EL solution or CREMOPHOR RH 40 solution), saccharide fatty acid esters (i.e., the condensation product of a monosaccharide (e.g., pentoses, such as, ribose, ribulose, arabinose, xylose, lyxose, and xylulose; hexoses, such as glucose, fructose, galactose, mannose, and sorbose; trioses; tetroses; heptoses; and octoses), disaccharide (e.g., sucrose, maltose, lactose, and trehalose), oligosaccharide, or a mixture thereof with one or more $C_4$-$C_{22}$ fatty acids (e.g., saturated fatty acids, such as caprylic acid, capric acid, lauric acid, myristic acid, palmitic acid, and stearic acid; and unsaturated fatty acids, such as palmitoleic acid, oleic acid, elaidic acid, erucic acid, and linoleic acid), and steroidal esters); ethers (these are typically alkyl, aryl, and cyclic ethers having from 2 to about 30 carbons. Examples include diethyl ether, tetrahydrofuran, dimethyl isosorbide, diethylene glycol monoethyl ether), and glycofurol (tetrahydrofurfuranyl alcohol polyethylene glycol ether); ketones (these typically have from about 3 to about 30 carbons. Examples include acetone, methyl ethyl ketone, methyl isobutyl ketone); hydrocarbons (these are typically aliphatic, cycloaliphatic, and aromatic hydrocarbons having from about 4 to about 30 carbons). Examples include benzene, cyclohexane, dichloromethane, dioxolanes, hexane, n-decane, n-dodecane, n-hexane, sulfolane, tetramethylenesulfone, tetramethylenesulfoxide, toluene, dimethylsulfoxide (DMSO); and tetramethylene sulfoxide; oils (these include oils of mineral, vegetable, animal, essential, or synthetic origin). These include mineral oils, such as aliphatic and wax-based hydrocarbons, aromatic hydrocarbons, mixed aliphatic and aromatic based hydrocarbons, and refined paraffin oil; vegetable oils, such as linseed, tung, safflower, soybean, castor, cottonseed, groundnut, rapeseed, coconut, palm, olive, corn, corn germ, sesame, persic, and peanut oil; glycerides, such as mono-, di-, and triglycerides; animal oils, such as fish, marine, sperm, cod-liver, haliver, squaiene, squalane, and shark liver oil; oleic oils; and polyoxyethylated castor oil); alkyl, alkenyl, or aryl halides (these include alkyl or aryl halides having from 1 to about 30 carbons and one or more halogen substituents. Examples include methylene chloride); monoethanolamine; petroleum benzin; trolamine; omega-3 polyunsaturated fatty acids (e.g., alpha-linolenic acid, eicosapentaenoic acid, docosapentaenoic acid, or docosahexaenoic acid); polyglycol ester of 12-hydroxystearic acid and polyethylene glycol (SOLUTOL HS-15, from BASF, Ludwigshafen, Germany); polyoxyethylene glycerol; sodium laurate; sodium oleate; and sorbitan monooleate. Other pharmaceutically acceptable solvents for use in the invention are well known to those of ordinary skill in the art. General discussion relating to such solvents may be found in, for example, The Chemotherapy Source Book (Williams & Wilkens Publishing), The Handbook of Pharmaceutical Excipients, (American Pharmaceutical Association, Washington, D.C., and The Pharmaceutical Society of Great Britain, London, England, 1968), Modern Pharmaceutics 3d ed., (G. Banker et. al., eds., Marcel Dekker, Inc., New York, N.Y. (1995)), The Pharmacological Basis of Therapeutics, (Goodman & Gilman, McGraw Hill Publishing), Pharmaceutical Dosage Forms, (H. Lieberman et. al., eds., Marcel Dekker, Inc., New York, N.Y. (1980)), Remington's Pharmaceutical Sciences, 19th ed., (A. Gennaro, ed., Mack Publishing, Easton, Pa., (1995)), The United States Pharmacopeia 24, The National Formulary 19, (National Publishing, Philadelphia, Pa. (2000)); Spiegel, A. J., et al., "Use of Nonaqueous Solvents in Parenteral Products," J. Pharma. Sciences, Vol. 52, No. 10, pp. 917-927 (1963).

Solvents useful in the present invention include, but are not limited to, those known to stabilize the pyrazine compounds or pharmaceutically acceptable salts thereof. These typically include, for example, oils rich in triglycerides, such as safflower oil, soybean oil, and mixtures thereof; and alkyleneoxy-modified fatty acid esters, such as polyoxyl 40 hydrogenated castor oil and polyoxyethylated castor oils (e.g., CREMOPHOR EL solution or CREMOPHOR RH 40 solution). Commercially available triglycerides include INTRALIPID emulsified soybean oil (Kabi-Pharmacia Inc., Stockholm, Sweden), NUTRALIPID emulsion (McGaw, Irvine, Calif.), LIPOSYN II 20% emulsion (a 20% fat emulsion solution containing 100 mg safflower oil, 100 mg soybean oil, 12 mg egg phosphatides, and 25 mg glycerin per ml of solution; Abbott Laboratories, Chicago, Ill.), LIPOSYN III 2% emulsion (a 2% fat emulsion solution containing 100 mg safflower oil, 100 mg soybean oil, 12 mg egg phosphatides, and 25 mg glycerin per ml of solution; Abbott Laboratories, Chicago, Ill.), natural or synthetic glycerol derivatives containing the docosahexaenoyl group at levels of from about 25 to about 100% (by weight based on the total fatty acid content) (DHASCO from Martek Biosciences Corp., Columbia, Md.; DHA MAGURO from Daito Enterprises, Los Angeles, Calif.; SOYACAL; and TRAVEMULSION). Ethanol in particular is a useful solvent for dissolving a pyrazine compound or pharmaceutically acceptable salt thereof to form solutions, emulsions, and the like.

Additional components can be included in the compositions of this invention for various purposes generally known in the pharmaceutical industry. These components tend to impart properties that, for example, enhance retention of the pyrazine compound or salt at the site of administration, protect the stability of the composition, control the pH, and facilitate processing of the pyrazine compound or salt into pharmaceutical formulations, and the like. Specific examples of such components include cryoprotective agents; agents for preventing reprecipitation of the pyrazine compound or salt surface; active, wetting, or emulsifying agents (e.g., lecithin, polysorbate-80, TWEEN 80, pluronic 60, and polyoxyethylene stearate); preservatives (e.g., ethyl-p-hydroxybenzoate); microbial preservatives (e.g., benzyl alcohol, phenol, m-cresol, chlorobutanol, sorbic acid, thimerosal, and paraben); agents for adjusting pH or buffering agents (e.g., acids, bases, sodium acetate, sorbitan monolaurate, etc.); agents for adjusting osmolarity (e.g., glycerin); thickeners (e.g., aluminum monostearate, stearic acid, cetyl alcohol, stearyl alcohol, guar gum, methyl cellulose, hydroxypropylcellulose, tristearin, cetyl wax esters, polyethylene glycol, etc.); colorants; dyes; flow aids; non-volatile silicones (e.g., cyclomethicone); clays (e.g., bentonites); adhesives; bulking agents; flavorings; sweeteners; adsorbents; fillers (e.g., sugars such as lactose, sucrose, mannitol, sorbitol, cellulose, calcium phosphate, etc.); diluents (e.g., water, saline, electrolyte solutions, etc.); binders (e.g., gelatin; gum tragacanth; methyl cellulose; hydroxypropyl methylcellulose; sodium carboxymethyl cellulose; polyvinylpyrrolidone; sugars; polymers; acacia; starches, such as maize starch, wheat starch, rice starch, and potato starch; etc.); disintegrating agents (e.g., starches, such as maize starch, wheat starch, rice starch, potato starch, and carboxymethyl starch; cross-linked polyvinyl pyrrolidone; agar; alginic acid or a salt thereof, such as sodium alginate; croscarmellose sodium; crospovidone; etc); lubricants (e.g., silica; talc; stearic acid and salts thereof, such as magnesium stearate; polyethylene glycol; etc.); coating agents (e.g., concentrated sugar solutions including gum arabic, talc, polyvinyl pyrrolidone, carbopol gel, polyethylene glycol, titanium dioxide, etc.); and antioxidants (e.g., sodium metabisulfite, sodium bisulfite, sodium sulfite, dextrose, phenols, thiophenols, etc.). Techniques and compositions for making parenteral dosage forms are generally known in the art. Formulations for parenteral administration may be prepared from one or more sterile powders and/or granules having a compound or salt of this invention and one or more of the carriers or diluents mentioned for use in the formulations for oral administration. The powder or granule typically is added to an appropriate volume of a solvent (typically while agitating (e.g., stirring) the solvent) that is capable of dissolving the powder or granule. Particular solvents useful in the invention include, for example, water, polyethylene glycol, propylene glycol, ethanol, corn oil, cottonseed oil, peanut oil, sesame oil, benzyl alcohol, sodium chloride, and/or various buffers.

Emulsions for parenteral administration can be prepared by, for example, dissolving a compound or salt of this invention in any pharmaceutically acceptable solvent capable of dissolving the compound to form a solution; and adding an appropriate volume of a carrier, which is an emulsion, to the solution while stirring to form the emulsion. Solutions for parenteral administration can be prepared by, for example, dissolving a compound or salt of this invention in any pharmaceutically acceptable solvent capable of dissolving the compound to form a solution; and adding an appropriate volume of a carrier to the solution while stirring to form the solution.

Suppositories for rectal administration can be prepared by, for example, mixing the drug with a suitable nonirritating excipient that is solid at ordinary temperatures, but liquid at the rectal temperature and will therefore melt in the rectum to release the drug. Suitable excipients include, for example, cocoa butter; synthetic mono-, di-, or triglycerides; fatty acids; and/or polyethylene glycols.

"Topical administration" includes the use of transdermal administration, such as transdermal patches or iontophoresis devices.

If desired, the emulsions or solutions described above for oral or parenteral administration can be packaged in IV bags, vials, or other conventional containers in concentrated form, and then diluted with a pharmaceutically acceptable liquid (e.g., saline) to form an acceptable pyrazine concentration before use.

Other adjuvants and modes of administration well known in the pharmaceutical art may also be used. Pharmaceutically acceptable salts comprise pharmaceutically-acceptable anions and/or cations. Pharmaceutically-acceptable cations include among others, alkali metal cations (e.g., $Li^+$, $Na^+$, $K^+$), alkaline earth metal cations (e.g., $Ca^{2+}$, $Mg^{2+}$), non-toxic heavy metal cations and ammonium ($NH_4^+$) and substituted ammonium ($N(R')_4^+$, where R' is hydrogen, alkyl, or substituted alkyl, i.e., including, methyl, ethyl, or hydroxyethyl, specifically, trimethyl ammonium, triethyl ammonium, and triethanol ammonium cations). Pharmaceutically-acceptable anions include among other halides (e.g., $F^-$, $Cl^-$, $Br^-$ $At^-$), sulfate, acetates (e.g., acetate, trifluoroacetate), ascorbates, aspartates, benzoates, citrates, and lactate.

The present compositions, preparations and formulations can be used both as a diagnostic agent as well as a photodynamic therapeutic agent concomitantly. For example, an effective amount of the present compositions, preparations and formulations in a pharmaceutically acceptable formulation is administered to a patient. Administration is followed by a procedure that combines photodiagnosis and phototherapy. For example, a composition comprising compounds for combined photodiagnosis and phototherapy is administered to a patient and its concentration, localization, or other parameters is determined at the target site of interest. More than one measurement may be taken to determine the location of the target site. The time it takes for the compound to accumulate at the target site depends upon factors such as pharmcokinetics, and may range from about thirty minutes to two days. Once the site is identified, the phototherapeutic part of the procedure may be done either immediately after determining the site or before the agent is cleared from the site. Clearance depends upon factors such as pharmacokinetics.

The present compositions, preparations and formulations can be formulated into diagnostic or therapeutic compositions for enteral, parenteral, topical, aerosol, inhalation, or cutaneous administration. Topical or cutaneous delivery of the compositions, preparations and formulations may also include aerosol formulation, creams, gels, solutions, etc. The present compositions, preparations and formulations are administered in doses effective to achieve the desired diagnostic and/or therapeutic effect. Such doses may vary widely depending upon the particular compositions employed in the composition, the organs or tissues to be examined, the equipment employed in the clinical procedure, the efficacy of the treatment achieved, and the like. These compositions, preparations and formulations contain an effective amount of the composition(s), along with conventional pharmaceutical carriers and excipients appropriate for the type of administration contemplated. These compositions, preparations and formulations may also optionally include stabilizing agents and skin penetration enhancing agents.

Methods of this invention comprise the step of administering an "effective amount" of the present diagnostic and therapeutic compositions, formulations and preparations containing the present compounds or compositions, to diagnose, image, monitor, evaluate, treat, reduce, alleviate, ameliorate or regulate a biological condition and/or disease state in a patient. The term "effective amount," as used herein, refers to the amount of the diagnostic and therapeutic formulation, that, when administered to the individual is effective to diagnose, image, monitor, evaluate, treat, reduce alleviate, ameliorate or regulate a biological condition and/or disease state. As is understood in the art, an effective amount of a given composition or formulation will depend at least in part upon the mode of administration (e.g. intravenous, oral, topical administration), any carrier or vehicle employed, and the specific individual to whom the formulation is to be administered (age, weight, condition, sex, etc.). The dosage requirements needed to achieve the "effective amount" vary with the particular formulations employed, the route of administration, and clinical objectives. Based on the results obtained in standard pharmacological test procedures, projected daily dosages of active compound or composition can be determined as is understood in the art. As used herein, "treat" means reduce or regulate a biological condition and/or disease state in a patient.

Any suitable form of administration can be employed in connection with the diagnostic and therapeutic formulations of the present invention. The diagnostic and therapeutic formulations of this invention can be administered intravenously, in oral dosage forms, intraperitoneally, subcutaneously, or intramuscularly, all using dosage forms well known to those of ordinary skill in the pharmaceutical arts.

The diagnostic and therapeutic formulations of this invention can be administered alone, but may be administered with a pharmaceutical carrier selected upon the basis of the chosen route of administration and standard pharmaceutical practice.

The diagnostic and therapeutic formulations of this invention and medicaments of this invention may further comprise one or more pharmaceutically acceptable carrier, excipient, buffer, emulsifier, surfactant, electrolyte or diluent. Such compositions and medicaments are prepared in accordance with acceptable pharmaceutical procedures, such as, for example, those described in Remingtons Pharmaceutical Sciences, 17th edition, ed. Alfonoso R. Gennaro, Mack Publishing Company, Easton, Pa. (1985).

It is understood that this invention is not limited to the particular compounds, methodology, protocols, and reagents described, as these may vary. It is also to be understood that the terminology used herein is for the purpose of describing particular embodiments only, and is not intended to limit the scope of the invention which will be limited only by the appended claims.

Compositions of the invention includes formulations and preparations comprising one or more of the present compounds provided in an aqueous solution, such as a pharmaceutically acceptable formulation or preparation. Optionally, compositions of the invention further comprise one or more pharmaceutically acceptable surfactants, buffers, electrolytes, salts, carriers, binders, coatings, preservatives and/or excipients.

EXAMPLE 2

Detection of COX-II Enzyme Using Optical Techniques

In an exemplary protocol for detecting or imaging binding of the COX-II enzyme, the pyrazine derivative is exposed to visible and/or near infrared light. This exposure of the pyrazine derivative to light may occur at any appropriate time but preferably occurs while the pyrazine derivative is located in the body. Due to this exposure of the pyrazine derivative to the visible and/or infrared light, the pyrazine derivative emits spectral energy (e.g., visible and/or near infrared light) that may be detected by appropriate detection equipment. The spectral energy emitted from the pyrazine derivative tends to exhibit a wavelength range greater than a wavelength range absorbed by the pyrazine derivative. For example, if the pyrazine derivative absorbs light of about 700 nm, the pyrazine derivative may emit light of about 745 nm.

Detection of the pyrazine derivative (or more particularly, light emitted therefrom) may be achieved through optical fluorescence, absorbance or light scattering procedures known in the art. This detection of the emitted spectral energy, or luminescence, may be characterized as a collection of the emitted spectral energy and a generation of electrical signal indicative of the collected spectral energy. For these purposes, the term "luminescence" includes the emission of light from excited electronic states of atoms or molecules. Luminescence generally refers to electromagnetic radiation emission, such as photoluminescence, chemiluminescence, and electrochemiluminescence, among others. In photoluminescence, including fluorescence and phosphorescence, the excited electronic state is created by the absorption of electromagnetic radiation. Luminescence detection involves detection of one or more properties of the luminescence or associated luminescence process. These properties can include intensity, excitation and/or emission spectrum, polarization, lifetime, and energy transfer, among others. These properties can also include time-independent (steady-state) and/or time-dependent (time-resolved) properties of the luminescence. Representative luminescence techniques include fluorescence intensity (FLINT), fluorescence polarization (FP), fluorescence resonance energy transfer (FRET), fluorescence lifetime (FLT), total internal reflection fluorescence (TIRF), fluorescence correlation spectroscopy (FCS), fluorescence recovery after photobleaching (FRAP), and bioluminescence resonance energy transfer (BRET), among others. By way of example, when an optical agent is used in the present invention, it is desirable that the wavelength of radiation be non-ionizing and be such that it excites the optical agent. This excitation can cause a bond of the molecule to break and can lead to creation of one or more appropriate radical(s). This excitation can also cause the molecule to emit part of the absorbed energy at a different wavelength. Such emission can be detected using fluorometric techniques as described above. One skilled in the art can readily determine the most appropriate treatment and optional detection technique based, at least in part, on the specific phototherapeutic agent(s) administered and/or the particular use (e.g., tissue to be treated).

"Phototherapy procedure" refers to a therapeutic procedure involving administration of a phototherapeutic agent to a patient followed by subsequent excitation by exposure to applied electromagnetic radiation, such as electromagnetic radiation having wavelengths in the visible and/or near IR region of the electromagnetic spectrum. Such wavelengths can be in the range of 350-1300 nanometers, so as to generate a therapeutically effective amount of excited phototherapeutic agent. Phototherapy includes, but is not limited to, photodynamic therapy. As used herein, "phototherapy" includes procedures involving administration of Type 1 and/or Type 2 phototherapeutic agents, optionally further including administration of one or more additional therapeutic agents. A detectable optical signal may be, for example, an observable change in absorbance, reflectance, phosphorescence, chemiluminescence, scattering, or other spectral property. Compounds of the invention can be phototherapeutic agents.

As used herein, "tumor-specific agent" refers to a compound or composition, such as an optical agent, that preferentially accumulates in a tumor at a higher level than normal tissue regardless of the particular mechanism of uptake in the tumors, for example, receptor mediated or enhanced permeability and retention (EPR). Optical agents of the invention include tumor-specific agents, including tumor specific phototherapy agents, for example having a targeting ligand providing specificity in the administration, delivery and/or binding to tumor tissue. Compounds of the invention can be tumor-specific agents.

By way of example, when a compound is used in the present invention, it is desirable that the wavelength of light supplied to the compound be such that it excites the compound. This excitation causes the molecule to emit part of the absorbed energy at a different wavelength, and the emission can be detected using fluorometric techniques as described above. One skilled in the art can readily determine the most appropriate detection technique based on, in part, the specific compound(s) administered, the particular use (e.g., tissue to be detected) and other aspects, including physical limitations of the analysis.

The techniques utilized to detect the spectral energy from the pyrazine derivative that is present in the body may be designed to detect only selected wavelengths (or wavelength ranges) and/or may include one or more appropriate spectral filters. Various catheters, endoscopes, ear clips, headbands, surface coils, finger probes, and the like may be utilized to expose the pyrazine derivative to light and/or to detect light emitting therefrom. This detection of spectral energy may be accomplished at one or more times intermittently or may be substantially continuous.

Preferably, non-ionizing energy is administered to the subject or sample for detecting or imaging cells binding of a compound of the invention to the COX-II enzyme. For these purposes, the term "non-ionizing energy" generally refers to electromagnetic radiation that does not carry enough energy to completely remove at least one electron from an atom or molecule of the patient's body. For example, in some embodiments, non-ionizing energy may include spectral energy ranging in wavelength from about 350 nm to about 1200 nm. In some embodiments, non-ionizing energy may simply include visible and/or near infrared light.

EXAMPLE 3

Synthesis

The pyrazine derivatives of the invention can be synthesized according to the methods in references known to the art and using the provided procedures and modifications thereof known to one of ordinary skill in the art. Synthesis of certain pyrazine derivatives is provided in references including: (i) Shirai, K. et al, Synthesis of fluorescent properties of 2,5-diamino-3,6-dicyanopyrazine dyes. Dyes and Pigments 1998, 39(1), 49-68; (ii) Kim, J. H. et al., Self-assembling of aminopyrazine fluorescent dyes and their solid state spectra. Dyes and Pigments 1998 39(4), 341-357; (iii) Barlin, G. B., The pyrazines. In The Chemistry of Heterocyclic Compounds. A. Weissberger and E. C. Taylor, Eds. John Wiley & Sons, New York: 1982; (iv) Donald, D. S., Synthesis of 3-5-diaminopyrazinoic acid from 3,5-diamino-2,6-dicyanopyrazine and intermediates. U.S. Pat. No. 3,948,895 (1976); (v) Donald, D. S., Diaminosubstituted dicyanopyrazines and process, U.S. Pat. No. 3,814,757 (1974); (vi) WO20061071759; (vii) WO07/149,478.

EXAMPLE 3A

Synthesis of Synthesis of 3-amino-6-[4-(dimethylamino)phenyl]-5-[4-(methylsulfonyl)phenyl]pyrazine-2-carboxylic acid

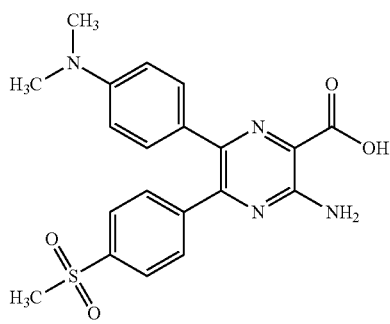 [SMILES: CN(C)c1ccc(-c2nc(C(=O)O)c(N)nc2-c2ccc(S(C)(=O)=O)cc2)cc1]

Step 1: A mixture of methyl 3-amino-5,6-dichloro-2-pyrazinecarboxylate (1.0 mmol, 222.0 mg), 4-(methylsulfonyl)phenyl botanic acid (1.2 mmol, 240.0 mg), and tetrakis (triphenylphosphine) Pd (0) (0.12 mmol, 138.7 mg) in 50 ml of anhydrous dimethylformamide was mixed via inert conditions. A solution of potassium carbonate (5 mmoles, 691.1 mg) in deionized water (3 ml) was added to the reaction mixture and heated at 75° C. overnight under an argon atmosphere. The product was purified by reversed phase HPLC (5-75 acetonitrile with 0.1% trifluoroacetic acid at 50 ml/min on XBridge Prep C18 OBD 5um 30×150 mm. Retention time 5.9 min) and characterized by 1H and $^{13}$C NMR. $^1$H NMR (500 MHz, DMSO-$d_6$) δ 8.08 (dt apparent, J=9.0 Hz, 2.0 Hz, 2H), δ 7.99 (cit apparent, J=8.5 Hz, 1.5 Hz, 2H), δ 7.66 (bs, 2H), δ 3.30 (s, 3H). $^{13}$C NMR (125 MHz, DMSO-$d_6$) δ 43.8 (s), δ 122.5 (s), δ 127.2 (s), δ 130.7 (s), δ 130.9 (s), δ 141.1 (s), δ 142.1 (s), δ 153.3 (s), δ 154.9 (s), δ 167.2 (s).

Step 2: A mixture of 3-amino-6-chloro-5-[4-(methylsulfonyl)phenyl]pyrazine-2-carboxylic acid (0.18 mmol, 60 mg,), 4-(dimethylamino)phenyl boronic acid (0.24 mmol, 40 mg), tetrakis(triphenylphosphine) Pd(0) (0.033 mmol, 38 mg), cesium carbonate (2.1 mmol, 297 mg) in dimethylformamide (2 ml) and deionized water (0.4 ml) was mixed under argon at room temperature. The reaction was heated in a microwave reactor at 120° C. for 15 min. The product was characterized by LC-MS (5-50 acetonitrile with 0.1% trifluoroacetic acid, positive ion [M+H]$^+$=413).

EXAMPLE 3B

Synthesis of 2-cyano-3-amino-6-[4-(disubstituted amino)phenyl]-5-[4-(methylsulfonyl)phenyl]pyrazine

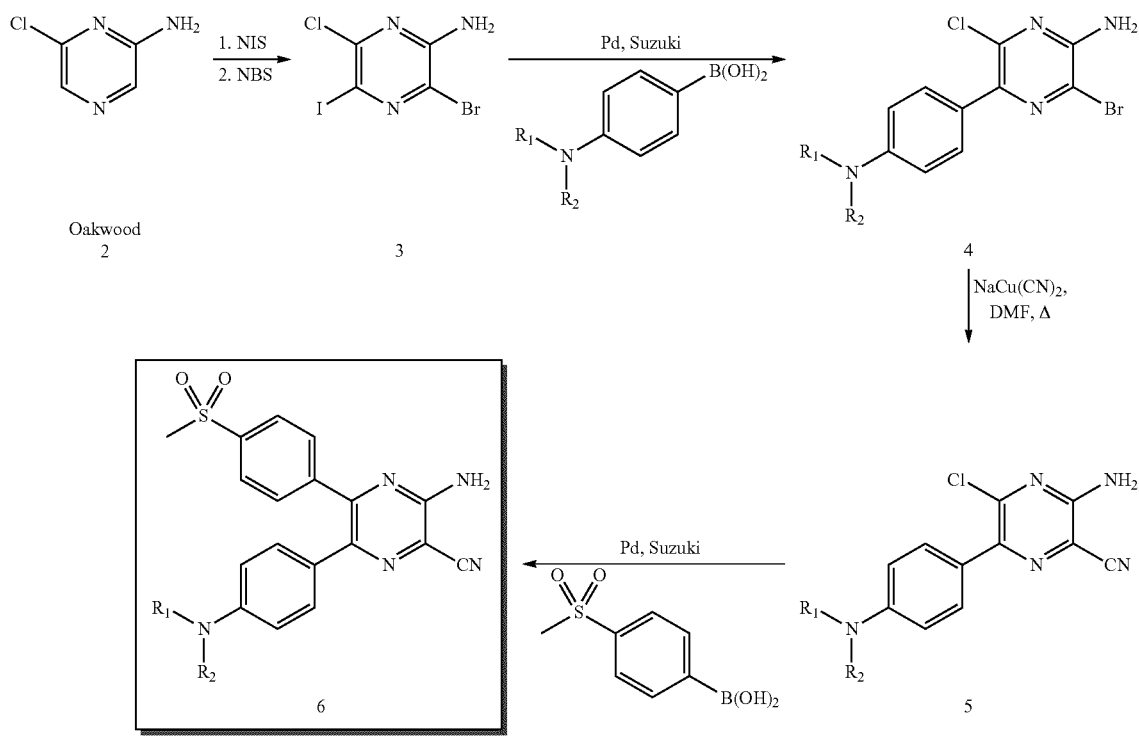

Commercially available chloropyrazine 2 can be converted to the fully orthogonally functionalized 3 using a one pot-two step iodination-bromination protocol. Selective Suzuki couplings can then be performed on the iodine in the presence of the chloride and bromide. A range of 4-substituted phenyl boronic acids can be introduced in this position via this chemistry. Thus, coupling with a 4-aminophenyl boronic acid derivative will provide compound 4. This material can then be converted to 5 by selective cyanation of the bromide. With compound 5 in hand a variety of Suzuki couplings can be performed on the chloride position to complete the syntheses of a range of integrated photonic COX-II inhibitors. Thus, coupling with 4-methyl-sulfonylphenyl boronic acid will provide compound 6.

EXAMPLE 3C

Alternative Synthesis to Pyrazine Based Compounds

Shown below is an alternative synthesis of pyrazine compounds of the invention. Commercially available compound I can be converted to compound 5 as shown in the reaction scheme using reaction conditions as known in the art. The substituent groups described herein can be substituted into the compounds using methods known in the art. Also shown is known compound Etoricoxib.

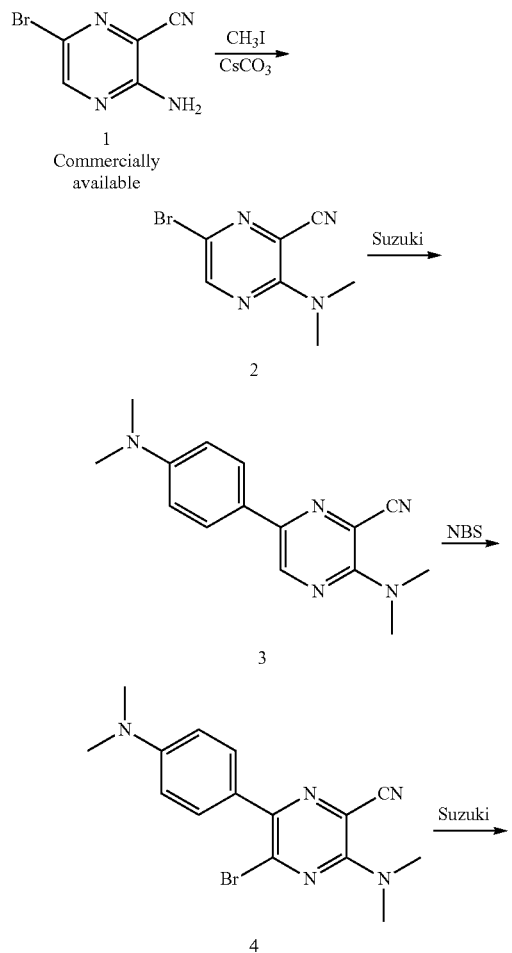

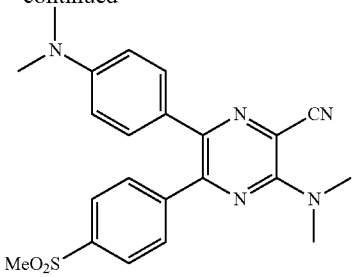

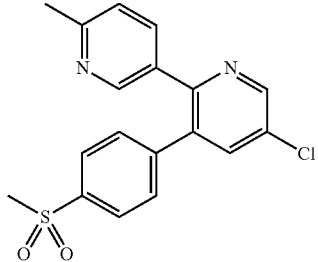

Etoricoxib

EXAMPLE 4

Biological Evaluation

Rat Carrageenan Foot Pad Edema Test

The carrageenan foot edema test can be performed with materials, reagents, and procedures essentially as described by Winter, et al., (Proc. Soc. Exp. Biol. Med., Ill, 544 (1962)). The test requires male Sprague-Dawley rats selected in each group so that the average body weight is as close as possible. Rats are fasted with free access to water for over sixteen hours prior to the test. The rats are dosed orally (1 mL) with compounds suspended in vehicle containing 0.5% methylcellulose and 0.025% surfactant, or with vehicle alone. One hour later a subplantar injection of 0.1 mL of 1% solution of carrageenan/sterile 0.9% saline is administered and the volume of the injected foot measured with a displacement plethysmometer connected to a pressure transducer with a digital indicator. Three hours after the injection of the carrageenan, the volume of the foot is again measured. The average foot swelling in a group of drug-treated animals is compared with that of a group of placebo-treated animals and the percentage inhibition of edema is determined (Otterness and Bliven, Laboratory Models for Testing NSAIDs, in Nonsteroidal Anti-Inflammatory Drugs, (J. Lombardino, ed. 1985)).

Rat Carrageenan-Induced Analgesia Test

The analgesia test using rat carrageenan can be performed with materials, reagents, and procedures essentially as described by Hargreaves, at al., (Pain, 32, 77 (1988)). The test requires male Sprague-Dawley rats treated as previously described for the Carrageenan Foot Pad Edema test. Three hours after the injection of the carrageenan, the rats are placed in a special Plexiglas container with a transparent floor having a high intensity lamp as a radiant heat source, positionable under the floor. After an initial twenty-minute period, thermal stimulation is begun either on the injected foot or on the contralateral uninjected foot. A photoelectric cell turns off the lamp and timer when light is interrupted by paw withdrawal. The time until the rat withdraws its foot is then measured. The withdrawal latency in seconds may be determined for the control and drug-treated groups, and percent inhibition of the hyperalgesic foot withdrawal is determined.

EXAMPLE 5

Evaluation of COX I and COX II Inhibiting Activity In Vitro

The COX II inhibition activity of the compounds of this invention can be determined by the following methods.
Preparation of Recombinant Cox Baculoviruses:

The assay uses a 2.0 kb fragment containing the coding region of either human or murine COX-1 or human or murine COX-II cloned into a BamHI site of the baculovirus transfer vector pVL1393 (Invitrogen) to generate the baculovirus transfer vectors for COX-1 and COX-2 in a manner similar to the method of D. R. O'Reilly et al (Baculovirus Expression Vectors: A Laboratory Manual (1992)). Recombinant baculoviruses are isolated by transfecting 4 µg of baculovirus transfer vector DNA into $SF_9$ insect cells ($2 \times 10^8$) along with 200 ng of linearized baculovirus plasmid DNA by the calcium phosphate method. See M. D. Summers and G. E. Smith, A Manual of Methods for Baculovirus Vectors and Insect Cell Culture Procedures, Texas Agric. Exp. Station Bull. 1555 (1987). Recombinant viruses are purified by three rounds of plaque purification and high titer ($10^7$-$10^8$ pfulml) stocks of virus are prepared. For large-scale production, $SF_9$ insect cells are infected in 10-liter fermentors ($0.5 \times 10^6$/ml) with the recombinant baculovirus stock such that the multiplicity of infection was 0.1. After 72 hours the cells are centrifuged and the cell pellet homogenized in Tris/Sucrose (50 mM: 25%, pH 8.0) containing 1% 3[(3-cholamidopropyl)dimethylammonio]-l-propane-sulfonate (CHAPS). The homogenate is centrifuged at 10,000×G for 30 minutes, and the resultant supernatant stored at −80° C. before being assayed for COX activity.
Assay for COX-1 and COX-2 Inhibiting Activity:

COX activity can be assayed as $PGE_2$ formed/µg protein/time using an ELISA to detect the prostaglandin released. CHAPS-solubilized insect cell membranes containing the appropriate COX enzyme are incubated in a potassium phosphate buffer (50 mM, pH 8.0) containing epinephrine, phenol, and heme with the addition of arachidonic acid (10 mM). Compounds are pre-incubated with the enzyme for 10-20 minutes prior to the addition of arachidonic acid. Any reaction between the arachidonic acid and the enzyme is stopped after ten minutes at 37° C./room temperature by transferring 40 µL of reaction mix into 160 µL ELISA buffer and 25 µM indomethacin. The PGE formed is measured by standard ELISA technology (Cayman Chemical).
Human Whole Blood Assay (hWBA)

The human whole blood assays described in Pairet et al., (1998) Infiamm Res 47 (Suppl 2): S93-S101 and Warner et al., (1999) Proc. Natl. Acad. Sci. USA 99:7563-7569 are useful for determining activity of COX-1 and COX-2 using the compounds of the invention. COX-1 activity is determine by release of prostanoids from platelets after stimulation of human whole blood clotting and COX-2 activity is determined by release of prostanoids from white blood cells over a time of about 18 hours following incubation of whole blood by LPS (bacterial lipopolysaccharide).
Additional COX Assays In vitro assays which use the target cells for the anti-inflammatory effects of NSAIDs such as gastric mucosa cells, chondrocytes or synoviocytes can be used because it is thought that increased COX-2 selectivity is correlated with reduced gastrointestinal toxicity.

EXAMPLE 6

Structure-Function Analysis

As shown in FIG. 1, structural regions of the compounds described herein have functions in binding of the compounds to a particular biological target such as COX-II, optical functionality, and electronic tuning. Changes to the structure of each of these regions provides desired changes to the functions described.

As described in "Cox-2 Inhibitors" M. Pairet/J, van Ryn Editors. 2004 Burkhauser Verlag Base1, and Cochrane, et al., (2002) Etoricoxib, Drugs 62: 2637-2651, the central ring of the compounds orients the two rings attached to the pyrazine ring into the binding pocket of the COX-2 enzyme. The six-membered ring of etoricoxib is believed to position the two aryl/heteroaryl rings and side chains so that etoricoxib exhibits greater selectivity to COX-2 binding in relation to COX-1 as compared to other studied COX-2 inhibitor compounds, for example. The two rings attached to the pyrazine ring of the compounds of the invention is important for binding of the compounds of the invention as well as providing selectivity of the compounds. The side chains on the electronic tuning portion of the molecule are useful in shifting the electronic properties of the molecule as well as providing regions for positioning groups that will improve the tolerability of the compound to a subject.

Diarylheterocyclic compounds with different central rings have been found to inhibit COX-2 expression and also be useful as anti-inflammatory agents. However, many of these compounds are not tolerated well in humans. In an embodiment, cyano and small amine groups present on the electronic tuning portion of the compounds of the invention should be tolerated by patients.

STATEMENTS REGARDING INCORPORATION BY REFERENCE AND VARIATIONS

All references throughout this application, for example patent documents including issued or granted patents or equivalents; patent application publications; and non-patent literature documents or other source material; are hereby incorporated by reference herein in their entireties, as though individually incorporated by reference, to the extent each reference is at least partially not inconsistent with the disclosure in this application (for example, a reference that is partially inconsistent is incorporated by reference except for the partially inconsistent portion of the reference).

The terms and expressions which have been employed herein are used as terms of description and not of limitation, and there is no intention in the use of such terms and expressions of excluding any equivalents of the features shown and described or portions thereof, but it is recognized that various modifications are possible within the scope of the invention claimed. Thus, it should be understood that although the invention has been specifically disclosed by preferred embodiments, exemplary embodiments and optional features, modification and variation of the concepts herein disclosed may be resorted to by those skilled in the art, and that such modifications and variations are considered to be within the scope of this invention as defined by the appended claims. The specific embodiments provided herein are examples of useful embodiments of the invention and it will be apparent to one skilled in the art that the invention may be carried out using a large number of variations of the devices, device components, methods steps set forth in the present description. As will be obvious to one of skill in the art, methods and devices useful for the present methods can include a large number of optional composition and processing elements and steps.

When a group of substituents is disclosed herein, it is understood that all individual members of that group and all subgroups, including any isomers, enantiomers, and diastereomers of the group members, are disclosed separately. When a Markush group or other grouping is used herein, all individual members of the group and all combinations and subcombinations possible of the group are intended to be individually included in the disclosure. When a compound is described herein such that a particular isomer, enantiomer or diastereomer of the compound is not specified, for example, in a formula or in a chemical name, that description is intended to include each isomers and enantiomer of the compound described individual or in any combination. Additionally, unless otherwise specified, all isotopic variants of compounds disclosed herein are intended to be encompassed by the disclosure. For example, it will be understood that any one or more hydrogens in a molecule disclosed can be replaced with deuterium or tritium. Isotopic variants of a molecule are generally useful as standards in assays for the molecule and in chemical and biological research related to the molecule or its use. Methods for making such isotopic variants are known in the art. Specific names of compounds are intended to be exemplary, as it is known that one of ordinary skill in the art can name the same compounds differently.

Many of the molecules disclosed herein contain one or more ionizable groups [groups from which a proton can be removed (e.g., —COOH) or added (e.g., amines) or which can be quaternized (e.g., amines)]. All possible ionic forms of such molecules and salts thereof are intended to be included individually in the disclosure herein. With regard to salts of the compounds herein, one of ordinary skill in the art can select from among a wide variety of available counterions those that are appropriate for preparation of salts of this invention for a given application. In specific applications, the selection of a given anion or cation for preparation of a salt may result in increased or decreased solubility of that salt.

Every formulation or combination of components described or exemplified herein can be used to practice the invention, unless otherwise stated.

Whenever a range is given in the specification, for example, a temperature range, a time range, or a composition or concentration range, all intermediate ranges and subranges, as well as all individual values included in the ranges given are intended to be included in the disclosure. It will be understood that any subranges or individual values in a range or subrange that are included in the description herein can be excluded from the claims herein.

All patents and publications mentioned in the specification are indicative of the levels of skill of those skilled in the art to which the invention pertains.

As used herein, "comprising" is synonymous with "including," "containing," or "characterized by," and is inclusive or open-ended and does not exclude additional, unrecited elements or method steps. As used herein, "consisting of" excludes any element, step, or ingredient not specified in the claim element. As used herein, "consisting essentially of" does not exclude materials or steps that do not materially affect the basic and novel characteristics of the claim. In each instance herein any of the terms "comprising", "consisting essentially of" and "consisting of" may be replaced with either of the other two terms. The invention illustratively described herein suitably may be practiced in the absence of any element or elements, limitation or limitations which is not specifically disclosed herein.

One of ordinary skill in the art will appreciate that starting materials, biological materials, reagents, synthetic methods, purification methods, analytical methods, assay methods, and biological methods other than those specifically exemplified can be employed in the practice of the invention without resort to undue experimentation. All art-known functional equivalents, of any such materials and methods are intended to be included in this invention. The terms and expressions which have been employed are used as terms of description and not of limitation, and there is no intention in the use of such terms and expressions of excluding any equivalents of the features shown and described or portions thereof, but it is recognized that various modifications are possible within the scope of the invention claimed. Thus, it should be understood that although the invention has been specifically disclosed by preferred embodiments and optional features, modification and variation of the concepts herein disclosed may be resorted to by those skilled in the art, and that such modifications and variations are considered to be within the scope of this invention as defined by the appended claims.

Various publications are references throughout this disclosure. A full citation corresponding to each reference number is listed below. The disclosures of the publications are herein incorporated by reference in their entireties.

REFERENCES

Ansorge, Nikolaus; Juettner, Stefan; Cramer, Thorsten; Schmidt, Wolfgang E.; Hoecker, Michael; Schmitz, Frank. An upstream CRE-E-box element is essential for gastrin-dependent activation of the cyclooxygenase-2 gene in human colon cancer cells. Regulatory Peptides (2007), 144(1-3), 25-33.

Chan, Andrew T.; Ogino, Shuji; Fuchs, Charles S. Aspirin and the risk of colorectal cancer in relation to the expression of COX-2. New England Journal of Medicine (2007), 356 (21), 2131-2142.

Tsuji, Masahiko; Tsuji, Shingo; Irie, Takanobu; Kakiuchi, Yoshimi; Yasumaru, Masakazu; Kawano, Sunao; Hayashi, Norio. Involvement of cyclooxygenase-2 in colorectal carcinogenesis. Recent Advances in Gastrointestinal Carcinogenesis (2006), 125-143.

Duque, Javier; Diaz-Munoz, Manuel D.; Fresno, Manuel; Iniguez, Miguel A. Up-regulation of cyclooxygenase-2 by interleukin-1β in colon carcinoma cells. Cellular Signalling (2006), 18(8), 1262-1269.

Tong, Xin; Yin, Lei; Joshi, Shree; Rosenberg, Daniel W.; Giardina, Charles. Cyclooxygenase-2 Regulation in Colon Cancer Cells: Modulation of RNA polymerase II elongation by histone deacetylase inhibitors. Journal of Biological Chemistry (2005), 280(16), 15503-15509.

Ghosh, Rita; Garcia, Gretchen E.; Crosby, Katherine; Inoue, Hiroyasu; Thompson, Ian M.; Troyer, Dean A.; Kumar, Addanki P. Regulation of Cox-2 by cyclic AMP response element binding protein in prostate cancer : potential role for nexrutine. Neoplasia (Ann Arbor, Mich., United States) (2007), 9(11), 893-899.

de Maat, Michiel F. G.; van de Velde, Cornelis J. H.; Umetani, Naoyuki; de Heer, Pieter; Putter, Hein; van Hoesel, Anneke Q.; Meijer, Gerrit A.; van Grieken, Nicole C.; Kuppen, Peter J. K.; Bilchik, Anton J.; Tollenaar, Rob A. E. M.; Hoon, Dave S. B. Epigenetic silencing of cyclooxygenase-2 affects clinical outcome in gastric cancer. Journal of Clinical Oncology (2007), 25(31), 4887-4894.

Xing, Guolan; Wang, Lidong; Wang, Nengchao; Wen, Wei; Qin, Ken; Fan, Zongmin; Li, Jilin; Zhang, Mei; Wu, Aiqun. Changes of COX-2 and VEGF expressions in esophageal precancerous and cancerous lesions from the patients at high incidence area in Henan province. Life Science Journal (2007), 4(2), 11-14.

Wang, Yuping; Xu, Xiaohui; Shen, Airong. Detection of COX-2, VEGF, and MVD in uterine endometrial carcinoma tissue. Zhengzhou Daxue Xuebao, Yixueban (2006), 41(5), 952-954. CODEN: ZDXYBA ISSN:1671-6825

Toeltzing, Oliver; Liu, Wenbiao; Fan, Fan; Wagner, Christine; Stengel, Kathrin; Somcio, Ray J.; Reinmuth, Niels; Parikh, Alexander A.; Hicklin, Daniel J.; Ellis, Lee M. Regulation of cyclooxygenase-2 (COX-2) expression in human pancreatic carcinoma cells by the insulin-like growth factor-I receptor (IGF-IR) system. Cancer Letters (Amsterdam, Netherlands) (2007), 258(2), 291-300.

Guo, Gui-long; Li, Zhuo-ying; You, Jie; Zhang, Xiao-hua. Mechanism and effect of selective COX-2 inhibitor nimesulide on the chemotherapy sensitiveness in breast cancer cell lines. Zhonghua Zhongliu Fangzhi Zazhi (2006), 13(16), 1214-1218.

Saldivar, J. Salvador; Lopez, David; Feldman, Rebecca A.; Tharappel-Jacob, Reena; de la Rosa, Antonio; Terreros, Daniel; Baldwin, William S. COX-2 overexpression as a biomarker of early cervical carcinogenesis : A pilot study. Gynecologic Oncology (2007), 107(1, Suppl. 1), S155-S162.

Bergmann, Christoph; Strauss, Laura; Zeidler, Reinhard; Lang, Stephan; Whiteside, Theresa L. Expansion of Human T Regulatory Type 1 Cells in the Microenvironment of Cyclooxygenase 2 Overexpressing Head and Neck Squamous Cell Carcinoma. Cancer Research (2007), 67(18), 8865-8873

Xu, Junli; He, Shuixiang; Chen, Jinghong; Fu, Han; Zhao, Gang; Wang, Yanli; Ren, Mudan. Effect of tanshinone II A on COX 2 expression in hepatocellular carcinoma cell line SMMC-7721. Shijie Huaren Xiaohua Zazhi (2006), 14(14), 1352-1356.

Rundhaug, Joyce E.; Mikulec, Carol; Pavone, Amy; Fischer, Susan M. A role for cyclooxygenase-2 in ultraviolet light-induced skin carcinogenesis. Molecular Carcinogenesis (2007), 46(8), 692-698

Kiguchi, Kaoru; Ruffino, Lynnsie; Kawamoto, Toru; Franco, Eugenia; Kurakata, Shin-ichi; Fujiwara, Kosaku; Hanai, Masaharu; Rumi, Mohammad; DiGiovanni, John. Therapeutic effect of CS-706, a specific cyclooxygenase-2 inhibitor, on gallbladder carcinoma in BK5.ErbB-2 mice. Molecular Cancer Therapeutics (2007), 6(6), 1709-1717.

Grozio, Alessia; Catassi, Alessia; Cavalieri, Zita; Paleari, Laura; Cesario, Alfredo; Russo, Patrizia. Nicotine, lung and cancer. Anti-Cancer Agents in Medicinal Chemistry (2007), 7(4), 461-466. CODEN: AAMCE4 ISSN:1871-5206.

Cao, Zongxian; Liu, Ling-Zhi; Dixon, Dan A.; Zheng, Jenny Z.; Chandran, Bala; Jiang, Bing-Hua. Insulin-like growth factor-I induces cyclooxygenase-2 expression via PI3K, MAPK and PKC signaling pathways in human ovarian cancer cells. Cellular Signalling (2007), 19(7), 1542-1553.

Lai, Ching-Shu; Li, Shiming; Chai, Chee-Yin; Lo, Chih-Yu; Ho, Chi-Tang; Wang, Ying-Jan; Pan, Min-Hsiung. Inhibitory effect of citrus 5-hydroxy-3,6,7,8,3',4'-hexamethoxyflavone on 12-O-tetradecanoylphorbol 13-acetate-induced skin inflammation and tumor promotion in mice. Carcinogenesis (2007), 28(12), 2581-2588.

Guo, Gui-long; Li, Zhuo-ying; You, Jie; Zhang, Xiao-hua. Mechanism and effect of selective COX-2 inhibitor nimesulide on the chemotherapy sensitiveness in breast cancer cell lines. Zhonghua Zhongliu Fangzhi Zazhi (2006), 13(16), 1214-1218.

Issa, Ala Y.; Volate, Suresh R.; Muga, Stephanie J.; Nitcheva, Daniela; Smith, Theresa; Wargovich, Michael J. Green tea selectively targets initial stages of intestinal carcinogenesis in the AOM-ApcMin mouse model. Carcinogenesis (2007), 28(9), 1978-1984.

Eisinger, Annie L.; Nadauld, Lincoln D.; Shelton, Dawne N.; Prescott, Stephen M.; Stafforini, Diana M.; Jones, David A. Retinoic Acid Inhibits—Catenin through Suppression of Cox-2: A role for truncated adenomatous polyposis coli. Journal of Biological Chemistry (2007), 282(40), 29394-29400.

Corona, Giulia; Deiana, Monica; Incani, Alessandra; Vauzour, David; Assunta Dessi, M.; Spencer, Jeremy P. E. Inhibition of p38/CREB phosphorylation and COX-2 expression by olive oil polyphenols underlies their antiproliferative effects. Biochemical and Biophysical Research Communications (2007), 362(3), 606-611.

Sano, Yasushi; Okuno, Tatsuya. Colon polyp and COX-2 inhibitor. Gan Bunshi Hyoteki Chiryo (2007), 5(2), 141-145.

Anti-EGFR and ErbB-2 antibodies attenuate cyclooxygenase-2 expression and cooperatively inhibit survival of human colon cancer cells. Cancer Letters (Amsterdam, Netherlands) (2007), 251(2), 237-246.

Jimeno, Antonio; Amador, Maria Luz; Kulesza, Peter; Wang, Xiaofei; Rubio-Viqueira, Belen; Zhang, Xiangfeng; Chan, Audrey; Wheelhouse, Jenna; Kuramochi, Hidekazu; Tanaka, Koji; Danenberg, Kathleen; Messersmith, Wells A.; Almuete, Virna; Hruban, Ralph H.; Maitra, Anirban; Yeo, Charles J.; Hidalgo, Manuel. Assessment of celecoxib pharmacodynamics in pancreatic cancer. Molecular Cancer Therapeutics (2006), 5(12), 3240-3247.

Fu, Suo-lin; Wu, Yun-lin; Qiao, Min-min; Zhang, Yong-ping; Chen, Ying; Sun, Bo; Qu, Qing. COX-2 inhibitors suppress activation of NF-κB in gastric cancer. Jiangxi Yixueyuan Xuebao (2006), 46(4), 16-20.

Kern, Michael A.; Haugg, Anke M.; Koch, Andreas F.; Schilling, Tobias; Breuhahn, Kai; Walczak, Henning; Fleischer, Binje; Trautwein, Christian; Michalski, Christoph; Schulze-Bergkamen, Henning; Friess, Helmut; Stremmel, Wolfgang; Krammer, Peter H.; Schirmacher, Peter; Mueller, Martina. Cyclooxygenase-2 Inhibition Induces Apoptosis Signaling via Death Receptors and Mitochondria in Hepatocellular Carcinoma. Cancer Research (2006), 66(14), 7059-7066.

Chen, Jen-Hao; Wu, Chew-Wun; Kao, Hwa-Li; Chang, Hwey-May; Li, Anna F-Y.; Liu, Tsung-Yun; Chi, Chin-Wen. Effects of COX-2 inhibitor on growth of human gastric cancer cells and its relation to hepatocyte growth factor. Cancer Letters (Amsterdam, Netherlands) (2006), 239(2), 263-270.

Krysan, Kostyantyn; Reckamp, Karen L.; Sharma, Sherven; Dubinett, Steven M. The potential and rationale for COX-2 inhibitors in lung cancer. Anti-Cancer Agents in Medicinal Chemistry (2006), 6(3), 209-220.

Irie, Takanobu; Tsujii, Masahiko; Tsuji, Shingo; Hayashi, Norio. Combination therapy of anticancer drugs and cyclooxygenase-2 (COX-2) inhibitors. Shokakika (2006), 42(2), 168-172.

Szabo, Gyoergy; Fischer, Janos; Kis-Varga, Agnes; Gyires, Klara. New Celecoxib Derivatives as Anti—Inflammatory Agents. Journal of Medicinal Chemistry (2008) ACS ASAP.

We claim:
1. A compound of the formula (FX1):

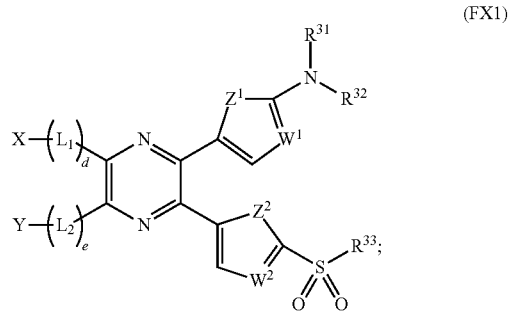

wherein:
  each of $Z^1$ and $Z^2$ is independently O, S, CH=CH, —$NR^{37}$, or $CH_2$;
  each of $W^1$ and $W^2$ is independently CH or N;
  each of $L_1$ and $L_2$ is independently —$(CH_2)_c$—, —$(HCCH)_c$—, —O—, —S—, —SO—, —$SO_2$—, —$SO_3$—, —$OSO_2$—, —$NR^{22}$—, —CO—, —COO—, —OCO—, —OCOO—, —$CONR^{23}$—, —$NR^{24}CO$—, —$OCONR^{25}$—, —$NR^{26}COO$—, —$NR^{27}CONR^{28}$—, or —$NR^{29}CSNR^{30}$—;
  each c is independently an integer from 1 to 10, and each of $R^{22}$-$R^{30}$ is independently hydrogen, $C_1$-$C_{10}$) alkyl, $C_3$-$C_{10}$ cycloalkyl, or $C_5$-$C_{10}$ aryl;
  each of X and Y is independently hydrogen, $C_1$-$C_{10}$ alkyl, $C_3$-$C_{10}$ cycloalkyl, $C_5$-$C_{10}$ aryl, $C_1$-$C_{10}$ acyl, $C_2$-$C_{10}$ alkenyl, $C_2$-$C_{10}$ alkynyl, $C_5$-$C_{10}$ alkylaryl, halo, halomethyl, dihalomethyl, trihalomethyl, —CN, —$CO_2R^1$, —$CONR^2R^3$, —$COR^4$, —$NO_2$, —$SOR^5$, —$OSR^{36}$, —$SO_2R^6$, —$SO_2OR^7$, —$SO_2NR^8R^9$, —$PO_3R^{10}R^{11}$, —$OR^{12}$, —$SR^{13}$, —$NR^{14}R^{15}$, —$NR^{16}COR^{17}$, or

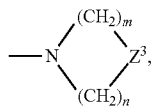

$Z^3$ is a single bond, —$CR^{18}R^{19}$—, —O—, —$NR^{20}$—, —$NCOR^{21}$—, —S—, —SO—, or —$SO_2$—;
each of $R^1$ to $R^{21}$, $R^{36}$ and $R^{37}$ is independently hydrogen or $C_1$-$C_{10}$ alkyl;
each of m and n is independently 1, 2, or 3, provided that m+n≥3 if $Z^3$ is a single bond;
each of $R^{31}$ and $R^{32}$ is independently H, $C_1$-$C_6$ alkyl, halo, halomethyl, dihalomethyl, or trihalomethyl;
$R^{33}$ is H, $NR^{34}R^{35}$, $C_1$-$C_6$ alkyl, halo, halomethyl, dihalomethyl, or trihalomethyl;
each of $R^{34}$ and $R^{35}$ is independently hydrogen or $C_1$-$C_3$ alkyl; and
each of d and e is independently 0 or 1.

2. The compound of claim 1, having the formula (FX2):

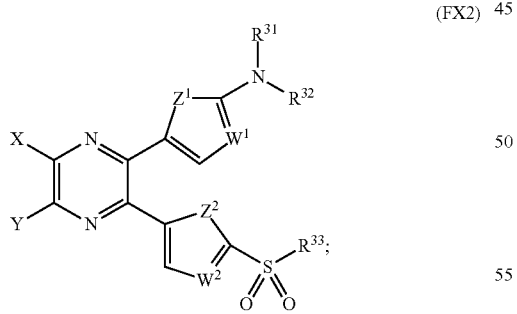

(FX2)

wherein:
  each of $Z^1$ and $Z^2$ is independently O, S, CH=CH, —$NR^{37}$, or $CH_2$;
  each of $W^1$ and $W^2$ is independently CH or N;
  each of X and Y is independently hydrogen, $C_1$-$C_{10}$ alkyl, $C_3$-$C_{10}$ cycloalkyl, $C_5$-$C_{10}$ aryl, $C_1$-$C_{10}$ acyl, $C_2$-$C_{10}$ alkenyl, $C_2$-$C_{10}$ alkynyl, $C_5$-$C_{10}$ alkylaryl, halo, halomethyl, dihalomethyl, trihalomethyl, —CN, —$CO_2R^1$, —$CONR^2R^3$, —$COR^4$, —$NO_2$, —$SOR^5$, —$OSR^{36}$, —$SO_2R^6$, —$SO_2OR^7$, —$SO_2NR^8R^9$, —$PO_3R^{10}R^{11}$, —$OR^{12}$, —$SR^{13}$, —$NR^{14}R^{15}$, —$NR^{16}COR^{17}$, or

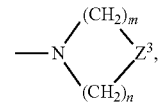

$Z^3$ is a single bond, —$CR^{18}R^{19}$—, —O—, —$NR^{20}$—, —$NCOR^{21}$—, —S—, —SO—, or —$SO_2$—;
each of $R^1$ to $R^{21}$, $R^{36}$ and $R^{37}$ is independently hydrogen or $C_1$-$C_{10}$ alkyl;
each of m and n is independently 1, 2, or 3, provided that m+n≥3 if $Z^3$ is a single bond;
each of $R^{31}$ and $R^{32}$ is independently H, $C_1$-$C_6$ alkyl, halo, halomethyl, dihalomethyl, or trihalomethyl;
$R^{33}$ is H, $NR^{34}R^{35}$, $C_1$-$C_6$ alkyl, halo, halomethyl, dihalomethyl, or trihalomethyl; and
each of $R^{34}$ and $R^{35}$ is independently hydrogen or $C_1$-$C_3$ alkyl.

3. The compound of claim 1, having the formula (FX3) to (FX9):

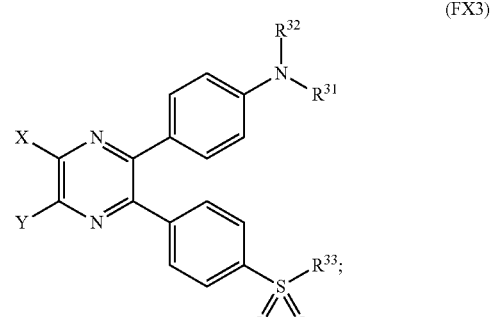

(FX3)

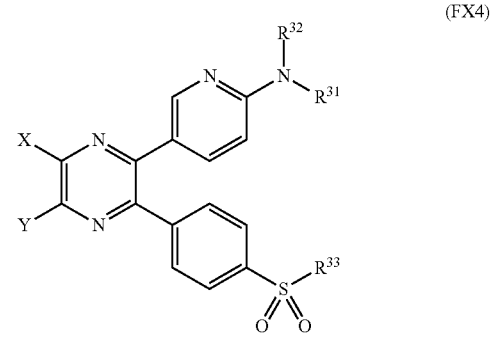

(FX4)

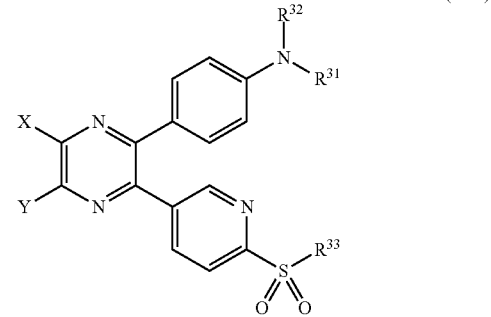

(FX5)

-continued

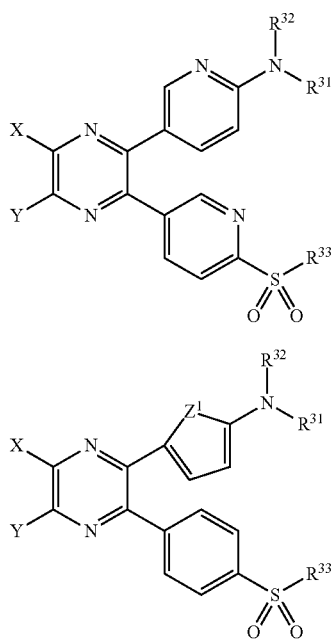

(FX6)

(FX7)

wherein in formula (FX7) $Z^1$ is O, S, or CH;

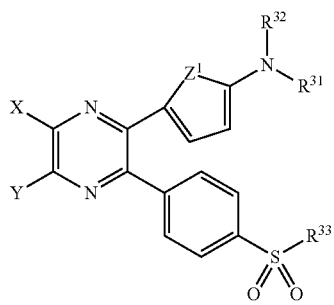

(FX8)

wherein in formula (FX8) $Z^2$ is O, S, or CH;

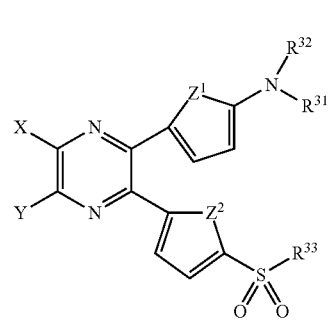

(FX9)

wherein in formula (FX9) each of $Z^1$ and $Z^2$ is independently O, S, or CH; wherein in each of (FX3); (FX4); (FX5); (FX6); (FX7); (FX8); and (FX9):
each of X and Y is independently hydrogen, $C_1$-$C_{10}$ alkyl, $C_3$-$C_{10}$ cycloalkyl, $C_5$-$C_{10}$ aryl, $C_1$-$C_{10}$ acyl, $C_2$-$C_{10}$ alkenyl, $C_2$-$C_{10}$ alkynyl, $C_5$-$C_{10}$ alkylaryl, halo, halomethyl, dihalomethyl, trihalomethyl, —CN, —$CO_2R^1$, —$CONR^2R^3$, —$COR^4$, —$NO_2$, —$SOR^5$, —$OSR^{36}$, —$SO_2R^6$, —$SO_2OR^7$, —$SO_2NR^8R^9$, —$PO_3R^{10}R^{11}$, —$OR^{12}$, —$SR^{13}$, —$NR^{14}R^{15}$, —$NR^{16}COR^{17}$, or

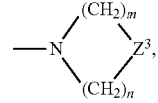

$Z^3$ is a single bond, —$CR^{18}R^{19}$—, —O—, —$NR^{20}$—, —$NCOR^{21}$—, —S—, —SO—, or —$SO_2$—;
each of $R^1$ to $R^{21}$ and $R^{36}$ is independently hydrogen or $C_1$-$C_{10}$) alkyl;
each of m and n is independently 1, 2, or 3, provided that m+n≥3 if $Z^3$ is a single bond;
each of $R^{31}$ and $R^{32}$ is independently H, $C_1$-$C_6$ alkyl, halo, halomethyl, dihalomethyl, or trihalomethyl;
$R^{33}$ is H, $NR^{34}R^{35}$, $C_1$-$C_6$ alkyl, halo, halomethyl, dihalomethyl, or trihalomethyl; and
each of $R^{34}$ and $R^{35}$ is independently hydrogen or $C_1$-$C_3$ alkyl.

4. The compound of claim 1, wherein:
one of X or Y is —CN, —$CO_2R^1$, —$CONR^2R^3$, —$COR^4$, —$NO_2$, —$SOR^5$, —$SO_2R^6$, —$SO_2OR^7$, —$SO_2NR^8R^9$, or —$PO_3R^{10}R^{11}$;
the other of X or Y is —$OR^{12}$, —$SR^{13}$, —$NR^{14}R^{15}$, —$NR^{16}COR^{17}$, or

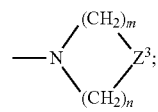

$Z^3$ is a single bond, —$CR^{18}R^{19}$—, —O—, —$NR^{20}$—, —$NCOR^{21}$—, —S—, —SO—, or —$SO_2$—;
each of $R^1$ to $R^{21}$ is independently hydrogen or $C_1$-$C_6$ alkyl; and
each of m and n is independently 1, 2, or 3, provided that m+n≥3 if $Z^3$ is a single bond.

5. The compound of claim 1, wherein:
one of X or Y is —CN, —$CO_2R^1$, —$CONR^2R^3$, —$COR^4$, —$NO_2$, —$SOR^5$, —$SO_2R^6$, —$SO_2OR^7$, —$SO_2NR^8R^9$, or —$PO_3R^{10}R^{11}$;
each of $R^1$-$R^{11}$ is independently hydrogen or $C_1$-$C_3$ alkyl;
the other of X or Y is —$NR^{14}R^{15}$; and
each of $R^{14}$-$R^{15}$ is independently hydrogen or $C_1$-$C_3$ alkyl.

6. The compound of claim 1, wherein one of X and Y is an electron withdrawing group, and the other of X and Y is an electron donating group.

7. The compound of claim 1, wherein one of X and Y is an electron withdrawing group, and the other of X and Y is hydrogen.

8. The compound of claim 1, wherein one of X and Y is an electron donating group, and the other of X and Y is hydrogen.

9. The compound of claim 1, wherein each of d and e is 0.

10. The compound of claim 1, wherein:
one of X and Y is —CN, —$CO_2R^1$, —$CONR^2R^3$, —$COR^4$, —$NO_2$, —$SOR^5$, —$SO_2R^6$, —$SO_2OR^7$, —$SO_2NR^8R^9$, or —$PO_3R^{10}R^{11}$;
each of $R^1$ to $R^{11}$ is independently hydrogen or $C_1$-$C_6$ alkyl; and
the other of X and Y is hydrogen.

11. The compound of claim 1, wherein:
one of X and Y is $OR^{12}$, —$SR^{13}$, —$NR^{14}R^{15}$, —$NR^{16}COR^{17}$, or

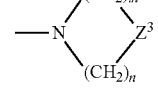

$Z^3$ is a single bond, $-CR^{18}R^{19}-$, $-O-$, $-NR^{20}-$, $-NCOR^{21}-$, $-S-$, $-SO-$, or $-SO_2-$;

each of $R^{12}$ to $R^{21}$ is independently hydrogen or $C_1$-$C_6$ alkyl;

each of m and n is independently 1, 2, or 3, provided that m+n≥3 if $Z^3$ is a single bond; and the other of X and Y is hydrogen.

12. The compound of claim 1, wherein:

X is $-CN$, $-CO_2R^1$, $-CONR^2R^3$, $-COR^4$, $-NO_2$, $-SOR^5$, $-SO_2R^6$, $-SO_2OR^7$, $-SO_2NR^8R^9$, or $-PO_3R^{10}R^{11}$;

Y is $OR^{12}$, $-SR^{13}$, $-NR^{14}R^{15}$, $-NR^{16}COR^{17}$, or

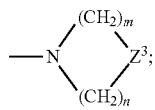

$Z^3$ is a single bond, $-CR^{18}R^{19}-$, $-O-$, $-NR^{20}-$, $-NCOR^{21}-$, $-S-$, $-SO-$, or $-SO_2-$;

each of $R^1$ to $R^{21}$ is independently hydrogen or $C_1$-$C_6$ alkyl;

each of m and n is independently 1, 2, or 3, provided that m+n≥3 if $Z^3$ is a single bond.

13. A pharmaceutical composition comprising:

a compound of formula (FX1)

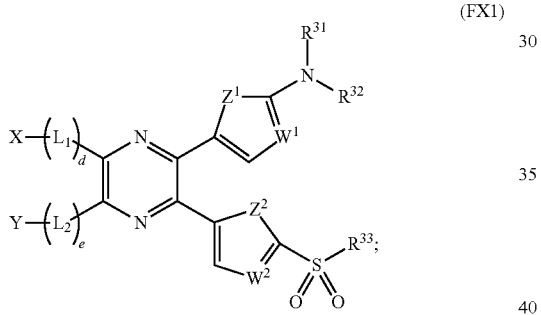

wherein:

each of $Z^1$ and $Z^2$ is independently O, S, $CH=CH$, $-NR^{37}$, or $CH_2$;

each of $W^1$ and $W^2$ is independently CH or N;

each of $L_1$ and $L_2$ is independently $-(CH_2)_c-$, $-(HCCH)_c-$, $-O-$, $-S-$, $-SO-$, $-SO_2-$, $-SO_3-$, $-OSO_2-$, $-NR^{22}-$, $-CO-$, $-COO-$, $-OCO-$, $-OCOO-$, $-CONR^{23}-$, $-NR^{24}CO-$, $-OCONR^{25}-$, $-NR^{26}COO-$, $-NR^{27}CONR^{28}-$, or $-NR^{29}CSNR^{30}-$;

each c is independently an integer from 1 to 10, and each of $R^{22}$-$R^{30}$ is independently hydrogen alkyl, $C_1$-$C_{10}$ cycloalkyl, or $C_5$-$C_{10}$ aryl;

each of X and Y is independently hydrogen, $C_1$-$C_{10}$ alkyl, $C_3$-$C_{10}$ cycloalkyl, $C_5$-$C_{10}$ aryl, $C_1$-$C_{10}$ acyl, $C_2$-$C_{10}$ alkenyl, $C_2$-$C_{10}$ alkynyl, $C_5$-$C_{10}$ alkylaryl, halo, halomethyl, dihalomethyl, trihalomethyl, $-CN$, $-CO_2R^1$, $-CONR^2R^3$, $-COR^4$, $-NO_2$, $-SOR^5$, $-OSR^{36}$, $-SO_2R^6$, $-SO_2OR^7$, $-SO_2NR^8R^9$, $-PO_3R^{10}R^{11}$, $-OR^{12}$, $-SR^{13}$, $NR^{14}R^{15}$, $-NR^{16}COR^{17}$, or

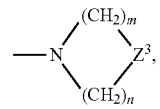

$Z^3$ is a single bond, $-CR^{18}R^{19}-$, $-O-$, $-NR^{20}-$, $-NCOR^{21}-$, $-S-$, $-SO-$, or $-SO_2$;

each of $R^1$ to $R^{21}$, $R^{36}$ and $R^{37}$ is independently hydrogen or $C_1$-$C_{10}$ alkyl;

each of m and n is independently 1, 2, or 3, provided that m+n≥3 if $Z^3$ is a single bond;

each of $R^{31}$ and $R^{32}$ is independently H, $C_1$-$C_6$ alkyl, halo, halomethyl, dihalomethyl or trihalomethyl;

$R^{33}$ is H, $NR^{34}R^{35}$, $C_1$-$C_6$ alkyl, halo, halomethyl, dihalomethyl, or trihalomethyl;

each of $R^{34}$ and $R^{35}$ is independently hydrogen or $C_1$-$C_3$ alkyl; and each of d and e is independently 0 or 1 and a pharmaceutically acceptable excipient.

* * * * *